(12) United States Patent
Lebert et al.

(10) Patent No.: US 11,630,111 B2
(45) Date of Patent: *Apr. 18, 2023

(54) METHOD FOR QUANTIFYING ANTI-TNF ANTIBODIES

(71) Applicant: Promise Advanced Proteomics, Grenoble (FR)

(72) Inventors: Dorothée Lebert, Le Gua (FR); Guillaume Picard, Mont-Saxonnex (FR)

(73) Assignee: PROMISE PROTEOMICS, Grenoble (FR)

(*) Notice: Subject to any disclaimer, the term of this patent is extended or adjusted under 35 U.S.C. 154(b) by 680 days.

This patent is subject to a terminal disclaimer.

(21) Appl. No.: 15/773,187

(22) PCT Filed: Nov. 4, 2016

(86) PCT No.: PCT/EP2016/076739
§ 371 (c)(1),
(2) Date: May 3, 2018

(87) PCT Pub. No.: WO2017/077080
PCT Pub. Date: May 11, 2017

(65) Prior Publication Data
US 2018/0321253 A1 Nov. 8, 2018

(30) Foreign Application Priority Data
Nov. 6, 2015 (EP) .................................... 15306759

(51) Int. Cl.
C07K 16/28 (2006.01)
G01N 33/68 (2006.01)
C07K 16/24 (2006.01)
G01N 33/573 (2006.01)

(52) U.S. Cl.
CPC ....... G01N 33/6848 (2013.01); C07K 16/241 (2013.01); G01N 33/573 (2013.01); G01N 2800/52 (2013.01); G01N 2800/56 (2013.01)

(58) Field of Classification Search
None
See application file for complete search history.

(56) References Cited

U.S. PATENT DOCUMENTS

2013/0064819 A1* 3/2013 Binks .................. C12Q 1/6883
424/134.1

FOREIGN PATENT DOCUMENTS

WO  WO 2006/131013  12/2006
WO  WO 2011/056590  5/2011

OTHER PUBLICATIONS

Allez, M., et al. The efficacy and safety of a third anti-TNF monoclonal antibody in Crohn's disease after faiIiure of two other anti-TNF antibodies. Alilment. Pharmacol. Ther., Jan. 2010, 31:92-101.*
Ahern, H. Biochemical, reagent kits offer scientists good return on investment, The Scientist, Jul. 24, 1995, 9(15):20, 5 pages.*
Heudi et al. 2008 Analytical Chemistry 80: 4200-4207. (Year: 2008).*
Bendtzen et al., Enzyme Immunoassays and Radioimmunoassays for Quantification of Anti-TNF Biopharmaceuticals and Anti-Drug Antibodies, Enzyme Immunoassays and Radioimmunoassays 83-101 (2011).
Duan et al., Nano-scale Liquid Chromatography/Mass Spectrometry and On-the-fly Orthogonal Array Optimization for Quantification of Therapeutic Monoclonal Antibodies and the Application in Preclinical Analysis, 1251 J. Chromatogr. A. 63-73 (Aug. 2012).
Dubois et al., Immunopurification and Mass Spectrometric Quantification of the Active Form of a Chimeric Therapeutic Antibody in Human Serum, 80 Anal. Chem. 1737-1745 1745 (2008).
Fernández Ocaña et al., Clinical Pharmacokinetic Assessment of an Anti-MAdCAM Monoclonal Antibody Therapeutic by LC-MS/MS, 84 Analytical Chemistry 5959-5967 (2012).
Heudi et al., Towards Absolute Quantification of Therapeutic Monoclonal Antibody in Serum by LC-MS/MS Using Isotope-Labeled Antibody Standard and Protein Cleavage Isotope Dilution Mass Spectrometry, 80(11) Anal. Chem. 4200-4207 (2008).
Kleinnijenhuis et al., A generic sample preparation approach for LC-MS/MS bioanalysis of therapeutic monoclonal antibodies in serum applied to Infliximab, 1(1) Journal of Applied Bioanalysis 26-34 (Jan. 2015).
Lebert et al., Absolute and multiplex quantification of antibodies in serum using PSAQ™ standards and LC-MS/MS, 7(10) Bioanalysis 1237-1251 (2015).
Lesur et al., Accelerated tryptic digestion for the analysis of biopharmaceutical monoclonal antibodies in plasma by liquid chromatography with tandem mass spectrometric detection, 1217 Journal of Chromatography A. 57-64 (2010).
Liu et al., Quantitation of a recombinant monoclonal antibody in monkey serum by liquid chromatograph-mass spectrometry, 414 Analytical Biochemistry 147-153 (2011).
Peng et al., Development and Validation of LC-MS/MS Method for the Quantitation of Infliximab in Human Serum, 78 Chromatographia 521-531 (2015).
Ungar et al., Significance of low level infliximab in the absence of anti-infliximab antibodies, 21(6) World J. Gastroenterol 1907-1914 (Feb. 14, 2015).
Vande Casteele et al., Detection of infliximab levels and anti-infliximab antibodies: a comparison of three different assays, 36 Aliment Pharmacol 765-771 (2012).
Wang et al., Development and validation of a homogeneous mobility shift assay for the measurement of infliximab and antibodies-to-infliximab levels in patent serum, 382 Journal of Immunological Methods 177-188 (2012).

(Continued)

Primary Examiner — Michael D Pak
(74) Attorney, Agent, or Firm — Buchanan Ingersool & Rooney PC

(57) ABSTRACT

The present invention relates to a method for quantifying an anti-TNF antibody in a sample of a human individual comprising a step of adding to a test sample which may contain therapeutic anti-TNF antibodies a known amount of two or more labeled forms of said anti-TNF antibodies.

3 Claims, 2 Drawing Sheets
Specification includes a Sequence Listing.

(56) References Cited

OTHER PUBLICATIONS

Willrich et al., *Quantification of infliximab using clonotypic peptides and selective reaction monitoring by LC-MS/MS*, 28 International Immunopharmacology 513-520 (2015).

Xu et al., *A multiplexed hybrid LC-MS/MS pharmacokinetic assay to measure two co-administered monoclonal antibodies in a clinical study*, 6(13) Bioanalysis 1781-1794 (2014).

Zhang et al., *Generic Automated Method for Liquid Chromatography—Multiple Reaction Monitoring Mass Spectrometry Based Monoclonal Antibody Quantification for Preclinical Pharmacokinetic Studies*, 86 Anal. Chem. 8776-8784 (2014).

* cited by examiner

METHOD FOR QUANTIFYING ANTI-TNF ANTIBODIES

CROSS-REFERENCE TO RELATED APPLICATIONS

This application is a U.S. National Stage Application pursuant to 35 U.S.C. § 371 of International Patent Application PCT/EP2016/076739, filed on Nov. 4, 2016, and published as WO 2017/077080 on May 11, 2017, which claims priority to European Patent Application 15306759, filed on Nov. 6, 2015, all of which are incorporated herein by reference in their entireties for all purposes.

FIELD OF THE INVENTION

This invention relates to the field of antibody quantification. It more precisely relates to the quantification of anti-TNF antibodies in a biological sample.

BACKGROUND OF THE INVENTION

Monoclonal antibodies (mAbs) constitute a therapeutic class which knows the strongest current rate of development in the field of pharmaceutical biotechnology. There are to date more than 50 mAbs marketed in various fields such as oncology, immunology, ophthalmology and cardiology.

Among them, anti-TNF antibodies blocking the action of TNF alpha revolutionized therapy of TNF-related diseases such as Inflammatory Bowel Disease, lupus, ulcerative colitis, ankylosing spondylitis, psoriatic arthritis and rheumatoid arthritis. By neutralizing TNF activity, anti-TNF antibodies promote mucosal healing and induce long-term remissions in patients. The main anti-TNF antibodies that are currently authorized encompass Infliximab, Etanercept, Adalimumab, Certolizumab and Golimumab.

However, some patients fail to respond to anti-TNF antibody therapy. In patients with a true primary non-response, drug levels are in the therapeutic range, but the response is poor. In contrast, secondary non-response occurs when a patient who initially responded to the anti-TNF therapy subsequently loses response, which may indicate the presence of anti-drug antibodies. For both situations, therapeutic drug monitoring provides an essential tool for evaluating subsequent treatment options.

Illustratively, regarding Infliximab anti-TNF therapy, a clinical study had shown that, despite all patients had received the same dose of this antibody, the serum drug concentration ranged from less than 21.3 µg/mL in the lowest quartile to greater than 47.9 µg/mL in the highest quartile at eight weeks (Reinish et al., 2012, Gastroenterology, Vol. 142(Suppl 1): S114). The proportion of patients achieving clinical remission, as assessed by the Mayo Score, increased with increasing quartiles of serum Infliximab concentration at weeks 8. A direct correlation with serum Infliximab concentration was also observed for clinical response and mucosal healing. A similar relationship was observed in open-label, multicentre, phase 3 study of pediatric patients with moderate-to-severe Ulcerative Colitis (Adedokun et al., 2013, Inflamm Bowel Dis, Vol. 19 (no 13) :2753-2762).

The clinical results reported above show that, in anti-TNF antibody therapy, drug monitoring shall be required in order to individualize dosing, which monitoring shall be most beneficial to patients who initially show a poor or absent response. In addition, individualized dose adjustments may be appropriate as the inflammatory burden changes. Because the relationship between drug dose and drug exposure varies from patient to patient, more frequent monitoring of serum drug levels and appropriate drug adjustments reveals necessary to maintain effective drug concentrations.

For monitoring serum concentration of anti-TNF antibodies, it has been reported the use of a mobility-shift assay based on high performance liquid chromatography (Wang et al., J Immunol Methods, 2012, Vol. 382(no 1-2): 177-188). It has also been reported the use of various ELISA methods (World J Gastroenterol 2015 Feb. 14; 21(6): 1907-1914).

As it can be readily understood, methods for monitoring serum concentration of anti-TNF antibodies shall be highly specific, sensitive, accurate and reproducible, so as to define the appropriate dosing adjustments that should be beneficial to a patient. Given the polypeptide nature of therapeutic mAbs, their high degree of homology with the endogenous human IgGs and the low concentrations at which they are expected in the plasma environment, the determination of plasma concentrations of therapeutic monoclonal antibodies is difficult. To date, reference techniques to identify and quantify mAbs rely on enzyme-linked immunosorbent assay methods (ELISA) due to their high sensitivity and availability. However ELISA methods present important limits especially in terms of reliability. (Vande Casteele N, Aliment Pharmacol Ther 2012; 36:765-771; Ungar B, World Journal of Gastroenterology 2015 Feb. 14; 21(6):1907-1914

Liquid chromatography coupled with tandem mass spectrometry (LC-MS/MS) was then viewed as an ideal candidate given its high specificity, sensitivity and accuracy of the measurement. LC-MS/MS allows more reliability than immunoassay techniques while maintaining a sufficient sensitivity for antibody quantification in human plasma. LC-MS/MS which is already widely used for the quantification of small molecules is a growing analytical tool for analysis of therapeutic proteins and proteomic biomarkers. The specificity and sensitivity of LC-MS/MS detection is achieved through the analysis in multiple reaction monitoring (MRM) mode of intact protein or of a surrogate peptide of the protein of interest obtained after enzymatic proteolysis of samples (Duan, X., et al., J Chromatogr A, 2012. 1251: p. 63-73; Dubois, M., et al., Anal Chem, 2008. 80(5): p. 1737-45; Fernandez Ocana, M., et al., Anal Chem, 2012. 84(14): p. 5959-67; Heudi, O., et al., Anal Chem, 2008. 80(11): p. 4200-7; Lesur, A., E. Varesio, and G. Hopfgartner, J Chromatogr A, 2010. 1217(1): p. 57-64; Liu, H., et al., Anal Biochem, 2011. 414(1): p. 147-53).

Quantification of an anti-TNF antibody with a LC-MS/MS method has already been performed in the art. Illustratively, Kleinnijenhuis et al. (2015, J Appl Bioanal, Vol. 1 (no 1): 26-34) have described a method for quantifying Infliximab by LC-MS/MS using SIL surrogate peptides derived from Infliximab as internal standards. The method described by Kleinnijenhuis et al. (2015) has been conceived for preclinical studies performed in rats by using surrogate peptides that are not found in rat antibodies. Quantification of Infliximab by a LC-MS/MS method has also been described by Willrich et al. (2015, International Immunopharmacology, Vol. 28: 513-520). The method described by Willrich et al. (2015) made use of SIL peptides derived from Infliximab as well as horse IgG as a surrogate internal standard. According to this method, Infliximab peptide peak areas were normalized to horse IgG peptide peak areas and SIL peptide internal standards were used to verify HPLC retention time. For the purpose of validating the specificity of this method to the exclusive quantification of Infliximab, the absence of any interference with other drugs, including anti-TNF antibodies such as Adalimumab, was ensured.

The present inventors have now identified that there is a need in the art for anti-TNF antibodies quantification methods that would allow an accurate quantification of a therapeutic anti-TNF antibody in samples collected from patients subjected to anti-TNF antibody treatments, which quantification methods shall be useful irrespective of the kind of therapeutic anti-TNF antibody that has been administered to those patients and moreover, non-sensitive to potential presence of other anti-TNF antibodies previously administered. Notably, the present inventors have identified that there is a need for all-in-one simple methods allowing to quantify anti-TNF antibodies in samples of anti-TNF-treated patients that would not require that the patricians to select a specific kit or method according to the anti-TNF therapeutic antibody that is expected to be contained in the patients samples.

SUMMARY OF THE INVENTION

The present invention relates to a method for quantifying an anti-TNF antibody in a sample of a human individual comprising the steps of:
- a) adding to a test sample which may contain therapeutic anti-TNF antibodies a known amount of two or more labeled forms of said anti-TNF antibodies selected in a group comprising Infliximab, Etanercept, Adalimumab, Certolizumab and Golimumab, whereby a pre-proteolysis sample is provided,
- b) subjecting the pre-proteolysis sample to an enzyme proteolysis, so as to provide a proteolysis sample comprising (i) proteolysis labeled peptides derived from the labeled anti-TNF antibodies and (ii) proteolysis peptides derived from the anti-TNF antibody contained in the test sample,
- c) determining by mass spectrometric analysis the ratio between (i) one or more selected proteolysis labeled peptides and (ii) one or more corresponding proteolysis peptides derived from the said anti-TNF antibody,
- d) calculating from the ratio determined at step c) the amount of the said anti-TNF antibody in the test sample.

In some embodiments of the method, step b) comprises the following steps:
- b1) a step of enzyme proteolysis in denaturing conditions, and
- b2) a step of enzyme proteolysis in non-denaturing conditions.

In some embodiments of the method, enzyme proteolysis is performed at step b) by using trypsin.

According to some aspects of these embodiments of the method, the one or more selected proteolysis peptides are selected in a group comprising:
- for Infliximab, peptides of the amino acid sequences of SEQ ID NO. 1 to 8,
- for Etanercept, peptides of the amino acid sequences of SEQ ID NO. 9 to 15,
- for Adalimumab, peptides of the amino acid sequences of SEQ ID NO. 16 to 23,
- for Certolizumab, peptides of the amino acid sequences of SEQ ID NO. 24 to 30, and
- for Golimumab, peptides of the amino acid sequences of SEQ ID NO. 31 to 37.

In some other embodiments of the method, enzyme proteolysis is performed at step b) by incubating the pre-proteolysis sample with a hinge-targeting protease, such as an Immunoglobulin-degrading enzyme from *Streptococcus* (ideS).

According to some aspects of these other embodiments of the method, the one or more selected proteolysis peptides are selected in a group comprising:
- for Infliximab, peptides of the amino acid sequences of SEQ ID NO. 38 and 39,
- for Etanercept, a peptide of the amino acid sequence of SEQ ID NO. 40,
- for Adalimumab, the peptides of the amino acid sequences of SEQ ID NO. 41 and 42,
- for Certolizumab, the peptides of the amino acid sequences of SEQ ID NO. 43 and 44, and
- for Golimumab, the peptides of the amino acid sequences of SEQ ID NO. 45 and 46.

According to some embodiments of the method, step a) comprises the following steps:
- a1) adding to a test sample which may contain therapeutic anti-TNF antibodies a known amount of two or more labeled forms of said anti-TNF antibodies selected in a group comprising Infliximab, Etanercept, Adalimumab, Certolizumab and Golimumab, whereby a non-concentrated pre-proteolysis sample is provided, and
- a2) enriching the non-concentrated pre-proteolysis sample in antibodies, whereby a pre-proteolysis sample is provided.

In preferred embodiments of the method, the test sample is a human sample from an individual who has been administered with an anti-TNF antibody selected in a group comprising Infliximab, Etanercept, Adalimumab, Certolizumab and Golimumab.

The present invention also relates to kits that are useful for performing the anti-TNF antibodies quantification method that is described herein.

DETAILED DESCRIPTION OF THE INVENTION

Figure 1:
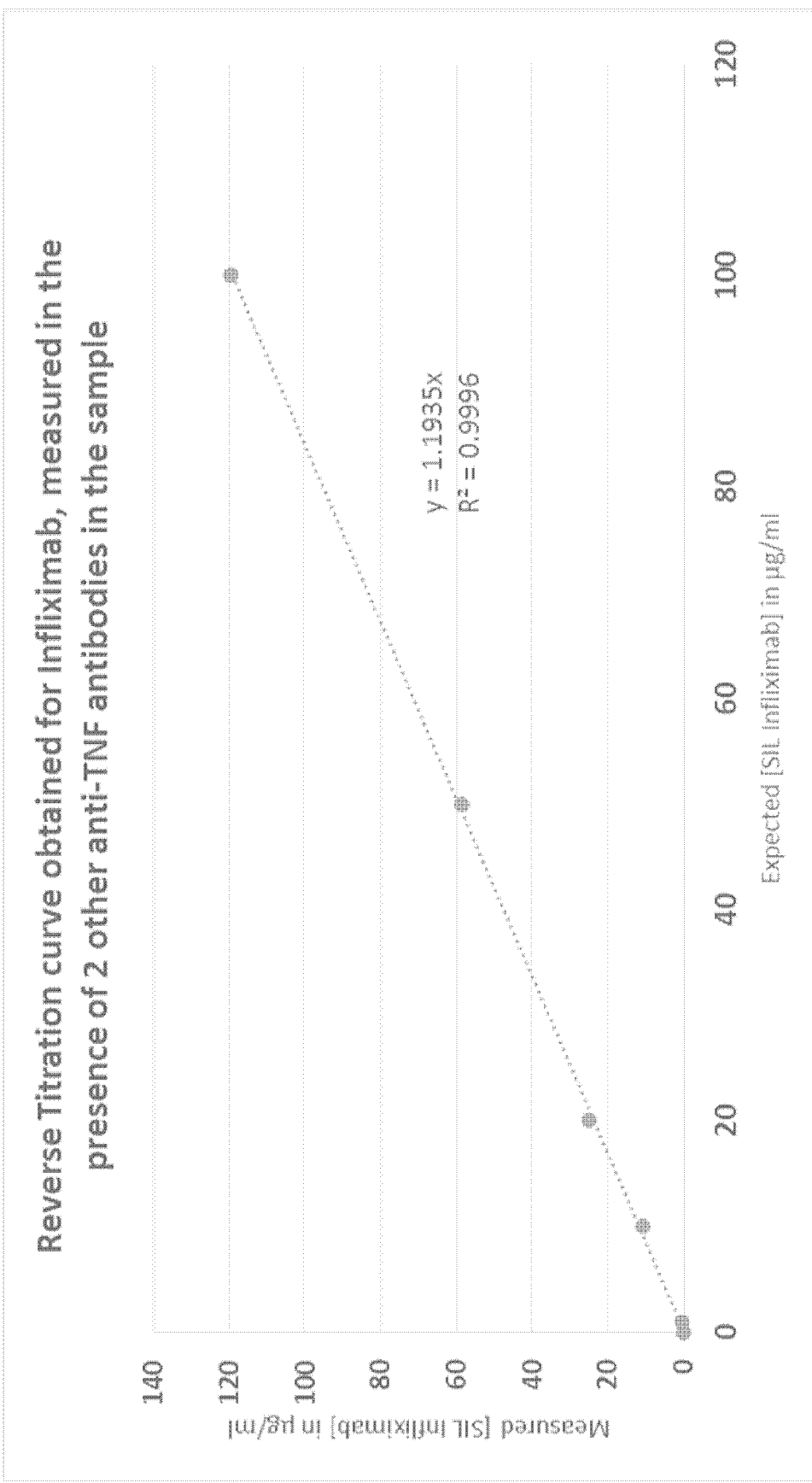
FIG. 1: Reverse titration curve obtained for Infliximab, measured in the presence of two other anti-TNF antibodies in a test sample.
Ordinate: Measured concentration of Infliximab as expressed in µg/mL. Abscissa: expected concentration of Infliximab as expressed in µg/mL.

This invention provides a method for quantifying an anti-TNF antibody in samples of human individuals that are treated with therapeutic anti-TNF antibodies, which method allows a precise quantification of anti-TNF antibodies, irrespective of the identity of the therapeutic anti-TNF antibody that is contained in the said sample to be tested.

The availability of the anti-TNF antibody quantification method that is described herein now provides the practitioners with a single method that may be used generally with samples of any human individual who receives a therapeutic treatment with anti-TNF antibodies, without taking care of the kind of anti-TNF antibody that has been administered to the said human individual.

Notably, in medical care units where some patients receive a treatment with a first anti-TNF antibody (e.g.

Infliximab) and where some other patients receive a treatment with a second anti-TNF antibody (e.g. Etanercept), the use of the anti-TNF quantification method described herein no more requires a selection of an antibody-specific quantification method as it is the case according to the present usual practice.

Further, in situations wherein a patient's treatment is erroneously documented, e.g. in situations wherein the said patient is deemed having received a first anti-TNF antibody (e.g. Infliximab) but has actually received a second antibody (e.g. Golimumab), the anti-TNF quantification method described herein nevertheless allows (i) determining which anti-TNF antibody the said patient has actually received and (ii) quantifying the anti-TNF antibody that has been administered to the said patient, despite the erroneous information provided to the test laboratory relating to the therapeutic anti-TNF antibody actually used.

Still further, in situations wherein the patient is subjected to a combination therapy by being administered with more than one anti-TNF antibody, the determination of the global circulating amount of anti-TNF antibodies, irrespective of the identity and of the number of anti-TNF antibodies that are used, may be performed globally by using the anti-TNF antibody quantification method that is described herein.

Yet further, in situations wherein the patient received a first treatment based on a first therapeutic anti-TNF antibody and then a second treatment based on a second therapeutic antibody, it follows that during a period of time subsequent to the said switch of treatment, both anti-TNF therapeutic antibodies will be present in the patient's body fluids, mainly in the patient's plasma. In these situations, the anti-TNF antibody quantification method described herein allows quantification of the whole anti-TNF antibodies in the said patient and also allows quantifying the respective amounts (e.g. plasma concentration) of each of the therapeutic anti-TNF antibodies.

The present invention provides a method for quantifying one or more anti-TNF antibodies in human samples, the said method allowing the quantification of said anti-TNF antibodies, even when the identity of the anti-TNF antibodies that were administered to the tested patients is not precisely known. This invention relates to a method for quantifying an anti-TNF antibody in a sample of a human individual that has received a therapeutic treatment with an anti-TNF antibody which may be selected in a group comprising Infliximab, Etanercept, Adalimumab, Certolizumab and Golimumab.

For performing the quantification method described herein, the two or more labeled form of therapeutic antibodies, i.e. the two labeled therapeutic antibodies, are labeled forms of therapeutic antibodies that are susceptible to be present in the human sample to be tested.

Illustratively, for quantifying therapeutic antibodies susceptible to be contained in human samples originating form medical care units hosting patients treated with anti-TNF antibodies and wherein a plurality of therapeutic anti-TNF antibodies are currently used for various treatments, then two or more of the labeled forms of the said therapeutic anti-TNF antibodies are added at step a) of the quantification method. Illustratively, for quantifying therapeutic anti-TNF antibodies in human samples originating from medical care units that make use of either Infliximab, Etanercept and Adalimumab, then the labeled forms of Infliximab, Etanercept and Adalimumab are added at step a) of the quantification method. Indeed, a higher number of labeled therapeutic antibodies, e.g. a higher number of labeled therapeutic anti-TNF antibodies, may be added at step a) of the method, e.g. the five therapeutic anti-TNF antibodies Infliximab, Etanercept, Adalimumab, Certolizumab and Golimumab. Such embodiments of the quantification method enable to perform the same embodiment of the quantification method described herein, e.g. with addition of five therapeutic anti-TNF antibodies, for quantifying anti-TNF antibodies in human samples provided by a plurality of medical care units making use of distinct anti-TNF antibodies, such as (i) a first medical care unit that performs treatments with Infliximab or Adalimumab, (ii) a second medical care unit that performs treatments with Etanercept, Adalimumab or Golimumab and (iii) a third medical care unit that performs treatments with Infliximab, Certolizumab and Golimumab. As it is illustrated, the therapeutic antibody quantification method described herein may be performed within the premises of a testing platform unit that centralizes the testing of human samples originating from a plurality of medical care units.

Thus, according to the therapeutic antibody quantification method described herein, a test sample "which may contain therapeutic antibodies" means a human sample which is expected to comprise at least one therapeutic antibody to be quantified by an embodiment of the quantification method wherein two or more labeled therapeutic antibodies are added at step a) and wherein at least a labeled form of the said at least one therapeutic antibody, included in the said two or more labeled therapeutic antibodies, are added at step a).

Thus, according to the therapeutic antibody quantification method described herein, a test sample "which may contain therapeutic antibodies" means a human sample which is expected to comprise at least one therapeutic antibody to be quantified by an embodiment of the quantification method wherein two or more labeled therapeutic antibodies are added at step a) and wherein at least a labeled form of the said at least one therapeutic antibody, included in the said two or more labeled therapeutic antibodies, are added at step a). Thus, step a) comprises adding a known amount of two or more labeled forms of therapeutic antibodies to a test sample which is suspected to contain one or more therapeutic antibodies and wherein one or more of the said labeled forms of therapeutic antibodies include a labeled form of the one or more therapeutic antibodies expected to be contained in the said test sample.

As used herein, "a" or "at least one" encompasses "one", or "more than one"; which encompasses a "plurality of therapeutic antibodies", such as two, or more than two, which may encompass, three, four, five, or even more than five therapeutic antibodies.

Accordingly, the therapeutic antibody quantification methods described herein are suitable for quantifying a therapeutic antibody in a sample of a human individual, which encompasses the quantification of at least one therapeutic antibody in a sample of a human individual; which encompasses the quantification of two or more (a plurality) of therapeutic antibodies in a sample of a human individual.

Thus, the invention relates to a method for quantifying two or more therapeutic antibodies in a sample of a human individual, as defined above, in which the test sample may contain two or more of said therapeutic antibodies to be quantified.

As used herein, the expression "comprises" or "comprising" encompasses also "consists of" or "consisting of".

As used herein, a "therapeutic antibody" refers to an antibody that is suitable for use as a medicament, and which may consist either of a whole antibody or a fragment thereof; which includes any fragment selected from a group comprising: human antibodies, humanized antibodies, synthetic antibodies, and chimeric antibodies. Most therapeutic antibodies are monoclonal antibodies, in particular of the IgG type. Fragments thereof may be selected from the group consisting of: Fab, F(ab')$_2$, scFv, Fc, pFc, Heavy chain and Light chain.

The quantification method that is described herein allows the quantification of two or more anti-TNF antibodies, irrespective of the identity of the said anti-TNF antibodies. The anti-TNF antibodies to be quantified by the method described herein may be any anti-TNF antibodies of therapeutic interest, e.g. any anti-TNF antibody that is the subject of a marketing authorization, at the time of performing the said anti-TNF antibody quantification method.

In some embodiments, the therapeutic antibody quantification method described herein may be performed for two or more antibodies selected in a group comprising Infliximab, Etanercept, Adalimumab, Certolizumab and Golimumab.

Infliximab Etanercept, Adalimumab, Certolizumab and Golimumab are polypeptides, the respective sequences of which are described hereunder.

-For Infliximab:
(Heavy chain, SEQ ID NO. 47)
EVKLEESGGGLVQPGGSMKLSCVASGFIFSNHWMNWVRQSPEKGLEWVAE
IRSKSINSATHYAESVKGRFTISRDDSKSAVYLQMTDLRTEDTGVYYCSR
NYYGSTYDYWGQGTTLTVSSASTKGPSVFPLAPSSKSTSGGTAALGCLVK
DYFPEPVTVSWNSGALTSGVHTFPAVLQSSGLYSLSSVVTVPSSSLGTQT
YICNVNHKPSNTKVDKKVEPKSCDKTHTCPPCPAPELLGGPSVFLFPPKP
KDTLMISRTPEVTCVVVDVSHEDPEVKFNWYVDGVEVHNAKTKPREEQYN
STYRVVSVLTVLHQDWLNGKEYKCKVSNKALPAPIEKTISKAKGQPREPQ
VYTLPPSRDELTKNQVSLTCLVKGFYPSDIAVEWESNGQPENNYKTTPPV
LDSDGSFFLYSKLTVDKSRWQQGNVFSCSVMHEALHNHYTQKSLSLSPGK (Light chain, SEQ ID NO. 48)
DILLTQSPAILSVSPGERVSFSCRASQFVGSSIHWYQQRTNGSPRLLIKY
ASESMSGIPSRFSGSGSGTDFTLSINTVESEDIADYYCQQSHSWPFTFGS
GTNLEVKRTVAAPSVFIFPPSDEQLKSGTASVVCLLNNFYPREAKVQWKV
DNALQSGNSQESVTEQDSKDSTYSLSSTLTLSKADYEKHKVYACEVTHQG
LSSPVTKSFNRGEC -For Adalimumab:
(Heavy chain, SEQ ID NO. 49)
EVQLVESGGGLVQPGRSLRLSCAASGFTFDDYAMHWVRQAPGKGLEWVSA
ITWNSGHIDYADSVEGRFTISRDNAKNSLYLQMNSLRAEDTAVYYCAKVS
YLSTASSLDYWGQGTLVTVSSASTKGPSVFPLAPSSKSTSGGTAALGCLV
KDYFPEPVTVSWNSGALTSGVHTFPAVLQSSGLYSLSSVVTVPSSSLGTQ
TYICNVNHKPSNTKVDKKVEPKSCDKTHTCPPCPAPELLGGPSVFLFPPK
PKDTLMISRTPEVTCVVVDVSHEDPEVKFNWYVDGVEVHNAKTKPREEQY
NSTYRVVSVLTVLHQDWLNGKEYKCKVSNKALPAPIEKTISKAKGQPREP
QVYTLPPSRDELTKNQVSLTCLVKGFYPSDIAVEWESNGQPENNYKTTPP
VLDSDGSFFLYSKLTVDKSRWQQGNVFSCSVMHEALHNHYTQKSLSLSPG
K (Light chain, SEQ ID NO. 50)
DIQMTQSPSSLSASVGDRVTITCRASQGIRNYLAWYQQKPGKAPKLLIYA
ASTLQSGVPSRFSGSGSGTDFTLTISSLQPEDVATYYCQRYNRAPYTFGQ
GTKVEIKRTVAAPSVFIFPPSDEQLKSGTASVVCLLNNFYPREAKVQWKV
DNALQSGNSQESVTEQDSKDSTYSLSSTLTLSKADYEKHKVYACEVTHQG
LSSPVTKSFNRGEC -For Etanercept:
(SEQ ID NO. 51)
LPAQVAFTPYAPEPGSTCRLREYYDQTAQMCCSKCSPGQHAKVFCTKTSD
TVCDSCEDSTYTQLWNWVPECLSCGSRCSSDQVETQACTREQNRICTCRP
GWYCALSKQEGCRLCAPLRKCRPGFGVARPGTETSDVVCKPCAPGTFSNT
TSSTDICRPHQICNVVAIPGNASMDAVCTSTSPTRSMAPGAVHLPQPVST
RSQHTQPTPEPSTAPSTSFLLPMGPSPPAEGSTGDEPKSCDKTHTCPPCP
APELLGGPSVFLFPPKPKDTLMISRTPEVTCVVVDVSHEDPEVKFNWYVD
GVEVHNAKTKPREEQYNSTYRVVSVLTVLHQDWLNGKEYKCKVSNKALPA
PIEKTISKAKGQPREPQVYTLPPSREEMTKNQVSLTCLVKGFYPSDIAVE
WESNGQPENNYKTTPPVLDSDGSFFLYSKLTVDKSRWQQGNVFSCSVMHE
ALHNHYTQKSLSLSPGK -For Certolizumab:
(Heavy chain, SEQ ID NO. 52)
EVQLVESGGGLVQPGGSLRLSCAASGYVFTDYGMNWVRQAPGKGLEWMGW
INTYIGEPIYADSVKGRFTFSLDTSKSTAYLQMNSLRAEDTAVYYCARGY
RSYAMDYWGQGTLVTVSSASTKGPSVFPLAPSSKSTSGGTAALGCLVKDY
FPEPVTVSWNSGALTSGVHTFPAVLQSSGLYSLSSVVTVPSSSLGTQTYI
CNVNHKPSNTKVDKKVEPKSCDKTHTCAA (Light chain, SEQ ID NO. 53)
DIQMTQSPSSLSASVGDRVTITCKASQNVGTNVAWYQQKPGKAPKALIYS
ASFLYSGVPYRFSGSGSGTDFTLTISSLQPEDFATYYCQQYNIYPLTFGQ
GTKVEIKRTVAAPSVFIFPPSDEQLKSGTASVVCLLNNFYPREAKVQWKV
DNALQSGNSQESVTEQDSKDSTYSLSSTLTLSKADYEKHKVYACEVTHQG
LSSPVTKSFNRGEC -For Golimumab:
(Heavy chain, SEQ ID NO. 54)
QVQLVESGGGVVQPGRSLRLSCAASGFIFSSYAMHWVRQAPGNGLEWVAF
MSYDGSNKKYADSVKGRFTISRDNSKNTLYLQMNSLRAEDTAVYYCARDR
GIAAGGNYYYYGMDVISSQGTTVTVSSASTKGPSVFPLAPSSKSTSGGTA
ALGCLVKDYFPEPVTVSWNSGALTSGVHTFPAVLQSSGLYSLSSVVTVPS
SSLGTQTYICNVNHKPSNTKVDKKVEPKSCDKTHTCPPCPAPELLGGPSV
FLFPPKPKDTLMISRTPEVTCVVVDVSHEDPEVKFNWYVDGVEVHNAKTK
PREEQYNSTYRVVSVLTVLHQDWLNGKEYKCKVSNKALPAPIEKTISKAK
GQPREPQVYTLPPSRDELTKNQVSLTCLVKGFYPSDIAVEWESNGQPENN
YKTTPPVLDSDGSFFLYSKLTVDKSRWQQGNVFSCSVMHEALHNHYTQKS
LSLSPGK -continued (Light chain, SEQ ID NO. 55)
EIVLTQSPATLSLSPGERATLSCRASQSVYSYLAWYQQKPGQAPRLLIYD

ASNRATGIPARFSGSGSGTDFTLTISSLEPEDFAVYYCQQRSNWPPFTFG

PGTKVDIKRTVAAPSVFIFPPSDEQLKSGTASVVCLLNNFYPREAKVQWK

VDNALQSGNSQESVTEQDSKDSTYSLSSTLTLSKADYEKHKVYACEVTHQ

GLSSPVTKSFNRGEC

More precisely, this invention pertains to such an anti-TNF antibody quantification method, which method makes use of a LC-MS/MS quantification technique.

Generally, for performing the anti-TNF antibody quantification method described herein, two or more reference anti-TNF antibodies (also termed "Internal Standard compounds" herein) are added to a test sample, before subjecting the resulting sample (also termed a "pre-proteolysis sample" to enzyme proteolysis, so as to provide a "proteolysis sample" comprising (i) proteolysis peptides derived from the reference anti-TNF antibodies and (ii) proteolysis peptides derived from the anti-TNF antibody contained in the test sample. At a further step of the method, the amount of the anti-TNF antibodies that were initially contained in the test sample is determined by a mass spectrometry method, which includes the calculation of a ratio between (i) one or more selected proteolysis peptides derived from the reference anti-TNF antibodies and (ii) one or more corresponding proteolysis peptides derived from the said anti-TNF antibodies susceptible to be initially contained in the test sample.

Indeed, for performing the anti-TNF antibody quantification method described herein, it is essential that (i) a given proteolysis peptide derived from a reference anti-TNF antibody (Internal Standard compound) and (ii) the corresponding proteolysis peptide derived from the anti-TNF antibody initially contained in the test sample be distinguished by the respective spectrometry signals that are generated by these peptides, so as to enable the calculation of a ratio between (i) the said proteolysis peptide derived from the said reference anti-TNF antibody and (ii) the said corresponding proteolysis peptide derived from the anti-TNF antibody initially contained in the test sample.

In preferred embodiments of the anti-TNF antibody quantification method described herein, these proteolysis peptides may be distinguished by mass spectrometry by using a Internal Standard compound consisting of a labeled anti-TNF antibody, and most preferably a Stable Isotopically Labeled (SIL) anti-TNF antibody.

Indeed, the anti-TNF antibody quantification method described herein is specifically designed for quantifying the amount (e.g. the concentration) of anti-TNF antibodies contained in body fluids from a patient treated with such anti-TNF antibodies, i.e. non-labeled therapeutic anti-TNF antibodies, so that the reference anti-TNF antibodies are most preferably labeled anti-TNF antibodies, and most preferably Stable Isotopically Labeled (SIL) anti-TNF antibodies, as it is fully illustrated throughout the entire present specification.

The present invention concerns a method for quantifying an anti-TNF antibody in a sample of a human individual comprising the steps of:
a) adding to a test sample which may contain therapeutic anti-TNF antibodies a known amount of two or more labeled forms of said anti-TNF antibodies selected in a group comprising Infliximab, Etanercept, Adalimumab, Certolizumab and Golimumab, whereby a pre-proteolysis sample is provided,
b) subjecting the pre-proteolysis sample to an enzyme proteolysis, so as to provide a proteolysis sample comprising (i) proteolysis labeled peptides derived from the labeled anti-TNF antibodies and (ii) proteolysis peptides derived from the anti-TNF antibody contained in the test sample,
c) determining by mass spectrometric analysis the ratio between (i) one or more selected proteolysis labeled peptides and (ii) one or more corresponding proteolysis peptides derived from the said anti-TNF antibody,
d) calculating from the ratio determined at step c) the amount of the said anti-TNF antibody in the test sample.

The inventors have shown that a precise quantification of anti-TNF antibodies in a human sample, which may be also termed "test sample" herein, may be allowed through the design of a method wherein the amount of anti-TNF antibodies, if present in the said sample, is determined by a mass spectrometry analysis making use of two or more labeled forms of said anti-TNF antibodies as Internal Standards of a LC-MS/MS quantification method.

The inventors have shown herein that the method that they have conceived allows a sensitive, specific and reproducible quantification of therapeutic antibodies in human samples, which encompasses human plasma samples and human serum samples. These advantages of the quantification method described herein are highly noticeable since most of the therapeutic anti-TNF antibodies to be quantified consist of humanized antibodies or "full human" antibodies which share most of their amino acid sequences with the antibodies which are naturally found in the human body fluids, including the antibodies which are found in the human serum or the human plasma. This situation represented a high technical challenge for selecting relevant specific and unique antibody-derived peptides to be monitored by spectrometry, which are not otherwise found naturally in human body fluids, including human serum or human plasma.

Illustratively, Infliximab is a murine-human chimeric anti-TNF antibody and thus contains mostly human amino acid sequences which are found in human antibodies. Infliximab is a genetically engineered chimeric murine/human monoclonal antibody directed against the TNF-alpha antigen. The antibody is an IgG1 kappa immunoglobulin containing murine light- and heavy-chain variable region sequences and human constant region sequences. It means that the amino acid sequences found in the constant regions are common to human IgG, amino acid sequences of the variable regions.

Etanercept is a recombinant dimeric fusion protein consisting of the extracellular ligand-binding portion of the human 75 kilodalton (p75) tumor necrosis factor receptor (TNFR) linked to the Fc portion of human IgG1. The Fc component of etanercept contains the CH2 domain, the CH3 domain and hinge region, but not the CH1 domain of IgG1. The only amino acid sequences that differ from human protein sequences are found in the linker region.

Adalimumab is a human monoclonal antibody against TNF-alpha, produced by recombinant DNA technology using a mammalian cell expression system. Tiny amino acid differences are found in the variable region compared to sequences of human IgG. Certolizumab pegol is a recombinant Fab' antibody fragment against tumor necrosis factor alpha which is conjugated to an approximately 40 kDa polyethylene glycol. Tiny amino acid differences are found in the variable region of the Fab' compared to sequences of human IgG.

Golimumab is a human IgG1κ monoclonal antibody derived from immunizing genetically engineered mice with human TNFα. Tiny amino acid differences are found in the variable region compared to sequences of human IgG.

As it is readily understood from the present specification, the quantification method described herein is useful both (i) in situations wherein a tested patient has received a therapeutic treatment by administration of a unique therapeutic anti-TNF antibody and (ii) in situations wherein a tested patient has received, simultaneously or sequentially, more than one therapeutic anti-TNF antibody.

As shown in the examples herein, the inventors have shown that a precise quantification of anti-TNF antibodies in a human sample may be performed through the design of a method wherein the amount of anti-TNF antibodies, if present in the said sample, is determined by a mass spectrometry method making use of (i) proteolysis peptide(s) derived from two or more therapeutic anti-TNF antibodies contained in the said human sample and (ii) proteolysis peptide(s) derived from a labeled form of the said two or more anti-TNF antibodies after:
  (A) calculating a ratio between:
    (i) the spectrometry signal generated by one or more selected anti-TNF antibody-derived proteolysis peptide from each of two or more anti-TNF antibodies and
    (ii) the spectrometry signal generated by one or more selected labeled anti-TNF antibody-derived proteolysis peptides from each of the two or more labeled form of the said two or more anti-TNF antibodies used as an Internal Standard compound(s), and
  (B) determining the amount of anti-TNF antibodies, if present, in the said human sample by reporting the ratio value calculated at step (A) for each of the one or more proteolysis peptide to a calibration curve of ratio values.

The kind of the Internal Standard compound(s) that is (are) used, namely whole labeled anti-TNF antibodies, strongly contributes to the accuracy and precision of the anti-TNF antibodies quantification method that is described herein as it is explained elsewhere in the present specification.

Internal Standard Compounds for Quantifying Anti-TNF Antibodies

As shown in the examples herein, (1) the high specificity of the proteolysis peptides derived from these Internal Standard compounds and of the therapeutic anti-TNF antibodies against endogenous human plasmatic proteins, as well as (2) the high physico-chemical homology of (i) the proteolysis peptides derived from these Internal Standard compounds, and of (ii) the proteolysis derived from the therapeutic anti-TNF antibodies, allows a highly precise quantification of the said anti-TNF antibodies in a sample.

For performing the anti-TNF antibody quantification method described herein, two or more distinct labeled anti-TNF antibodies are added to the test sample. Specific labeled proteolysis peptides (also termed "labeled surrogate peptides") are generated at step b), along with the corresponding non-labeled proteolysis peptides (also termed "surrogate peptides" or "non-labeled surrogate peptides") of the corresponding non-labeled TNF antibodies to be quantified that were initially present in the said test sample.

Then, as it is described in detail further in the present specification, the one or more anti-TNF antibodies present in the test sample are quantified by a mass spectrometric method wherein the signals generated by the labeled and non-labeled pairs of surrogate peptides are measured for determining a ratio between the two generated signals (i.e. the signal generated by a specific labeled surrogate peptide and the signal generated by the specific non-labeled surrogate peptide counterpart). Then, the ratio values are used for determining the concentration of the anti-TNF antibody(ies) initially contained in the test sample. Most preferably, the said ratio values are used for determining the concentration of the TNF antibody(ies) initially contained in the test sample by reporting these ratio values to a calibration curve of ratio values. Accordingly, the said "values" consist of the spectrometry signals generated by the monitored proteolysis peptides.

Then, the ratio value(s) are reported to a calibration curve so as to determine the amount (e.g. the concentration) of one or more anti-TNF antibodies in the test sample.

In some embodiments, a calibration curve represents (i) the measured amount of an anti-TNF antibody of interest (e.g. in ordinate) against (ii) the expected amount of the said anti-TNF antibody (e.g. in abscissa).

In some other embodiments, a calibration curve represents (i) the ratio values between the spectrometry signal area of an anti-TNF antibody of interest and the spectrometry signal area of the corresponding labeled anti-TNF antibody (Internal Standard compound) (e.g. in ordinate) against (ii) the expected amount of the said anti-TNF antibody (e.g. in abscissa).

The higher the number of distinct labeled anti-TNF antibodies are added in the test sample at step a) of the method, the higher the number of distinct anti-TNF antibodies may be quantified in a test sample by using the anti-TNF antibody quantification method described herein.

In some embodiments of the anti-TNF antibody quantification method of the invention, these one or more labeled anti-TNF antibodies correspond to (i) the labeled form(s) of one or more anti-TNF antibodies which have been administered to said individual, and/or of (ii) the labeled form(s) of one or more therapeutic antibodies which may be present within said test sample.

In some embodiments, these labeled anti-TNF antibodies may consist of one or more anti-TNF antibodies comprising one or more signature peptides present within the anti-TNF antibodies which (i) have been administered to said individual, and/or which (ii) may be present within said test sample, and which have to be quantified.

In some embodiments, these anti-TNF antibodies and labeled anti-TNF antibodies may consist of one or more humanized IgG antibodies, and fragments thereof.

In some embodiments of the anti-TNF antibodies quantification method of the invention, the number of labeled anti-TNF antibodies that are used as Internal Standard compounds ranges from two to five distinct labeled antibodies, which encompasses two, three, four and five distinct labeled antibodies. These labeled antibodies may be selected in a group comprising labeled Infliximab, labeled Etanercept, labeled Adalimumab, labeled Certolizumab and labeled Golimumab.

In some embodiments of the anti-TNF antibodies quantification method of the invention, the labeled anti-TNF antibodies that are used as Internal Standard compounds comprise labeled Infliximab and labeled Etanercept.

In some embodiments of the anti-TNF antibodies quantification method of the invention, the labeled anti-TNF antibodies that are used as Internal Standard compounds comprise labeled Infliximab and labeled Adalimumab.

In some embodiments of the anti-TNF antibodies quantification method of the invention, the labeled anti-TNF antibodies that are used as Internal Standard compounds comprise labeled Infliximab and labeled Certolizumab.

In some embodiments of the anti-TNF antibodies quantification method of the invention, the labeled anti-TNF antibodies that are used as Internal Standard compounds comprise labeled Infliximab and labeled Golimumab.

In some embodiments of the anti-TNF antibodies quantification method of the invention, the labeled anti-TNF antibodies that are used as Internal Standard compounds comprise labeled Etanercept and labeled Adalimumab.

In some embodiments of the anti-TNF antibodies quantification method of the invention, the labeled anti-TNF antibodies that are used as Internal Standard compounds comprise labeled Etanercept and labeled Certolizumab.

In some embodiments of the anti-TNF antibodies quantification method of the invention, the labeled anti-TNF antibodies that are used as Internal Standard compounds comprise labeled Etanercept and labeled Golimumab.

In some embodiments of the anti-TNF antibodies quantification method of the invention, the labeled anti-TNF antibodies that are used as Internal Standard compounds comprise labeled Adalimumab and labeled Certolizumab.

In some embodiments of the anti-TNF antibodies quantification method of the invention, the labeled anti-TNF antibodies that are used as Internal Standard compounds comprise labeled Adalimumab and labeled Golimumab.

In some embodiments of the anti-TNF antibodies quantification method of the invention, the labeled anti-TNF antibodies that are used as Internal Standard compounds comprise labeled Certolizumab and labeled Golimumab.

In some embodiments of the anti-TNF antibodies quantification method of the invention, the labeled anti-TNF antibodies that are used as Internal Standard compounds comprise labeled Infliximab, labeled Etanercept and labeled Adalimumab.

In some embodiments of the anti-TNF antibodies quantification method of the invention, the labeled anti-TNF antibodies that are used as Internal Standard compounds comprise labeled Infliximab, labeled Etanercept and labeled Certolizumab.

In some embodiments of the anti-TNF antibodies quantification method of the invention, the labeled anti-TNF antibodies that are used as Internal Standard compounds comprise labeled Infliximab, labeled Etanercept and labeled Golimumab.

In some embodiments of the anti-TNF antibodies quantification method of the invention, the labeled anti-TNF antibodies that are used as Internal Standard compounds comprise labeled Etanercept, labeled Adalimumab and labeled Certolizumab.

In some embodiments of the anti-TNF antibodies quantification method of the invention, the labeled anti-TNF antibodies that are used as Internal Standard compounds comprise labeled Etanercept, labeled Adalimumab and labeled Golimumab.

In some embodiments of the anti-TNF antibodies quantification method of the invention, the labeled anti-TNF antibodies that are used as Internal Standard compounds comprise labeled Certolizumab, labeled Adalimumab and labeled Golimumab.

In some embodiments of the anti-TNF antibodies quantification method of the invention, the labeled anti-TNF antibodies that are used as Internal Standard compounds comprise labeled Adalimumab, labeled Infliximab and labeled Certolizumab.

In some embodiments of the anti-TNF antibodies quantification method of the invention, the labeled anti-TNF antibodies that are used as Internal Standard compounds comprise labeled Adalimumab, labeled Infliximab and labeled Golimumab.

In some embodiments of the anti-TNF antibodies quantification method of the invention, the labeled anti-TNF antibodies that are used as Internal Standard compounds comprise labeled Certolizumab, labeled Infliximab and labeled Adalimumab.

In some embodiments of the anti-TNF antibodies quantification method of the invention, the labeled anti-TNF antibodies that are used as Internal Standard compounds comprise labeled Certolizumab, labeled Infliximab and labeled Golimumab.

In some embodiments of the anti-TNF antibodies quantification method of the invention, the labeled anti-TNF antibodies that are used as Internal Standard compounds comprise labeled Infliximab, labeled Etanercept, labeled Adalimumab and labeled Certolizumab.

In some embodiments of the anti-TNF antibodies quantification method of the invention, the labeled anti-TNF antibodies that are used as Internal Standard compounds comprise labeled Infliximab, labeled Etanercept, labeled Adalimumab and labeled Golimumab.

In some embodiments of the anti-TNF antibodies quantification method of the invention, the labeled anti-TNF antibodies that are used as Internal Standard compounds comprise labeled Infliximab, labeled Adalimumab, labeled Certolizumab and labeled Golimumab.

In some embodiments of the anti-TNF antibodies quantification method of the invention, the labeled anti-TNF antibodies that are used as Internal Standard compounds comprise labeled Infliximab, labeled Etanercept, labeled Certolizumab and labeled Golimumab.

In some embodiments of the anti-TNF antibodies quantification method of the invention, the labeled anti-TNF antibodies that are used as Internal Standard compounds comprise labeled Etanercept, labeled Adalimumab, labeled Certolizumab and labeled Golimumab.

In some embodiments of the anti-TNF antibodies quantification method of the invention, the labeled anti-TNF antibodies that are used as Internal Standard compounds comprise labeled Infliximab, labeled Etanercept, labeled Adalimumab, labeled Certolizumab and labeled Golimumab.

As used herein, a "labeled" anti-TNF antibody, also referred herein as a "labeled form of an anti-TNF antibody", selected in a group comprising labeled Infliximab, labeled Etanercept, labeled Adalimumab, labeled Certolizumab and labeled Golimumab consists of an antibody having the same amino acid sequence as a therapeutic anti-TNF antibody selected in a group comprising Infliximab, Etanercept, Adalimumab, Certolizumab and Golimumab and which has been obtained by a method according to which one or more labeled amino acids have been incorporated in the polypeptide chain(s). Methods for labeling the anti-TNF antibodies that are used as Internal Standard compounds in the anti-TNF antibody quantification method described herein are disclosed elsewhere in the present specification.

For performing the anti-TNF antibody quantification method of the invention wherein the proteolysis step b) makes use of trypsin as the sole protease or of trypsin as a protease contained in a protease mixture, the one or more selected proteolysis peptides are selected in a group comprising:

-for Infliximab:
(SEQ ID NO. 1)
LEESGGGLVQPGGSMK, (SEQ ID NO. 2)
GLEWVAEIR, (SEQ ID NO. 3)
SINSATHYAESVK, (SEQ ID NO. 4)
SAVYLQMTDLR, (SEQ ID NO. 5)
TEDTGVYYCSR, (SEQ ID NO. 6)
DILLTQSPAILSVSPGER, (SEQ ID NO. 7)
ASQFVGSSIHWYQQR, (SEQ ID NO. 8)
YASESMSGIPSR, -for Etanercept:
(SEQ ID NO. 9)
LPAQVAFTPYAPEPGSTCR, (SEQ ID NO. 10)
EYYDQTAQMCCSK, (SEQ ID NO. 11)
CSSDQVETQACTR, (SEQ ID NO. 12)
ICTCRPGWYCALSK, (SEQ ID NO. 13)
LCAPLR, (SEQ ID NO. 14)
SMAPGAVHLPQPVSTR, (SEQ ID NO. 15)
SQHTQPTPEPSTAPSTSFLLPMGPSPPAEGSTGDEPK, -or Adalimumab:
(SEQ ID NO. 16)
GLEWVSAITWNSGHIDYADSVEGR, (SEQ ID NO. 17)
VSYLSTASSLDYWGQGTLVTVSSASTK, (SEQ ID NO. 18)
QAPGKGLEWVSAITWNSGHIDYADSVEGR, (SEQ ID NO. 19)
ASQGIR, (SEQ ID NO. 20)
NYLAWYQQKPGK, (SEQ ID NO. 21)
LLIYAASTLQSGVPSR v, (SEQ ID NO. 22)
FSGSGSGTDFTLTISSLQPEDVATYYCQR, (SEQ ID NO. 23)
APYTFGQGTK, -for Certolizumab:
(SEQ ID NO. 24)
LSCAASGYVFTDYGMNWVR, (SEQ ID NO. 25)
GLEWMGWINTYIGEPIYADSVK, (SEQ ID NO. 26)
FTFSLDTSK, (SEQ ID NO. 27)
STAYLQMNSLR, (SEQ ID NO. 28)
ASQNVGTNVAWYQQKPGK, (SEQ ID NO. 29)
ALIYSASFLYSGVPYR (SEQ ID NO. 30)
FSGSGSGTDFTLTISSLQPEDFATYYCQQYNIYPLTFGQGTK, -or Golimumab:
(SEQ ID NO. 31)
LSCAASGFIFSSYAMHWVR, (SEQ ID NO. 32)
QAPGNGLEWVAFMSYDGSNK, (SEQ ID NO. 33)
GIAAGGNYYYYGMDVISSQGTTVTVSSASTK, (SEQ ID NO. 34)
ASQSVYSYLAWYQQK, (SEQ ID NO. 35)
LLIYDASNR, (SEQ ID NO. 36)
FSGSGSGTDFTLTISSLEPEDFAVYYCQQR, (SEQ NO. 37)
SNWPPFTFGPGTK, For performing the anti-TNF antibodies quantification method of the invention wherein the proteolysis step b) makes use of a hinge-targeting protease, the one or more selected proteolysis peptides are selected in a group comprising:

-for Infliximab:
(SEQ ID NO. 38)
EVKLEESGGGLVQPGGSMKLSCVASGFIFSNHWMNWVRQSPEKGLEWVAE
IRSKSINSATHYAESVKGRFTISRDDSKSAVYLQMTDLRTEDTGVYYCSR
NYYGSTYDYWGQGTTLTVSSASTKGPSVFPLAPSSKSTSGGTAALGCLVK
DYFPEPVTVSWNSGALTSGVHTFPAVLQSSGLYSLSSVVTVPSSSLGTQT
YICNVNHKPSNTKVDKKVEPKSCDKTHTCPPCPAPELLG[VH + CH1],
and (SEQ ID NO. 39)
DILLTQSPAILSVSPGERVSFSCRASQFVGSSIHWYQQRTNGSPRLLIKY
ASESMSGIPSRFSGSGSGTDFTLSINTVESEDIADYYCQQSHSWPFTFGS
GTNLEVKRTVAAPSVFIFPPSDEQLKSGTASVVCLLNNFYPREAKVQWKV
DNALQSGNSQESVTEQDSKDSTYSLSSTLTLSKADYEKHKVYACEVTHQG
LSSPVTKSFNRGEC[VL + CL], -for Etanercept:
(SEQ ID NO. 40)
LPAQVAFTPYAPEPGSTCRLREYYDQTAQMCCSKCSPGQHAKVFCTKTSD
TVCDSCEDSTYTQLWNWVPECLSCGSRCSSDQVETQACTREQNRICTCRP
GWYCALSKQEGCRLCAPLRKCRPGFGVARPGTETSDVVCKPCAPGTFSNT
TSSTDICRPHQICNVVAIPGNASMDAVCTSTSPTRSMAPGAVHLPQPVST -continued
RSQHTQPTPEPSTAPSTSFLLPMGPSPPAEGSTGDEPKSCDKTHTCPPCP APELLG[Fraction P75 du recepteur soluble du TNF alpha], -or Adalimumab:
(SEQ ID NO. 41)
EVQLVESGGGLVQPGRSLRLSCAASGFTFDDYAMHWVRQAPGKGLEWVSA

ITWNSGHIDYADSVEGRFTISRDNAKNSLYLQMNSLRAEDTAVYYCAKVS

YLSTASSLDYWGQGTLVTVSSASTKGPSVFPLAPSSKSTSGGTAALGCLV

KDYFPEPVTVSWNSGALTSGVHTFPAVLQSSGLYSLSSVVTVPSSSLGTQ

TYICNVNHKPSNTKVDKKVEPKSCDKTHTCPPCPAPELLG

[VH + CH1], (SEQ ID NO.42)
DIQMTQSPSSLSASVGDRVTITCRASQGIRNYLAWYQQKPGKAPKLLIYA

ASTLQSGVPSRFSGSGSGTDFTLTISSLQPEDVATYYCQRYNRAPYTFGQ

GTKVEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC[VL + CL]

-for Certolizumab:
(SEQ ID NO. 43)
EVQLVESGGGLVQPGGSLRLSCAASGYVFTDYGMNWVRQAPGKGLEWMGW

INTYIGEPIYADSVKGRFTFSLDTSKSTAYLQMNSLRAEDTAVYYCARGY

RSYAMDYWGQGTLVTVSSASTKGPSVFPLAPSSKSTSGGTAALGCLVKDY

FPEPVTVSWNSGALTSGVHTFPAVLQSSGLYSLSSVVTVPSSSLGTQTYI

CNVNHKPSNTKVDKKVEPKSCDKTHTCAA[VH + CH1], (SEQ ID NO. 44)
DIQMTQSPSSLSASVGDRVTITCKASQNVGTNVAWYQQKPGKAPKALIYS

ASFLYSGVPYRFSGSGSGTDFTLTISSLQPEDFATYYCQQYNIYPLTFGQ

GTKVEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC[VL + CL],

-or Golimumab:
(SEQ ID NO. 45)
QVQLVESGGGVVQPGRSLRLSCAASGFIFSSYAMHWVRQAPGNGLEWVAF

MSYDGSNKKYADSVKGRFTISRDNSKNTLYLQMNSLRAEDTAVYYCARDR

GIAAGGNYYYYGMDVISSQGTTVTVSSASTKGPSVFPLAPSSKSTSGGTA

ALGCLVKDYFPEPVTVSWNSGALTSGVHTFPAVLQSSGLYSLSSVVTVPS

SSLGTQTYICNVNHKPSNTKVDKKVEPKSCDKTHTCPPCPAPELLG

[VH + CH1], (SEQ ID NO. 46)
EIVLTQSPATLSLSPGERATLSCRASQSVYSYLAWYQQKPGQAPRLLIYD

ASNRATGIPARFSGSGSGTDFTLTISSLEPEDFAVYYCQORSNWPPFTFG

PGTKVDIKRTVAAPSVFIFPPSDEQLKSGTASVVCLLNNFYPREAKVQWK

VDNALQSGNSQESVTEQDSKDSTYSLSSTLTLSKADYEKHKVYACEVTHQ

GLSSPVTKSFNRGEC[VL + CL]

The anti-TNF antibodies that are used as Internal Standard compounds are labelled with one or more stable isotopes. Stable isotopes may be selected in a group comprising $^2H$, $^{13}C$, $^{15}N$ and $^{18}O$. Preferably, stable isotopes are selected in a group comprising $^{13}C$ and $^{15}N$.

In some embodiments, isotopic labeling is only restricted to specific amino acids, which are preferably Arginine, Lysine and/or Leucine.

A Stable Isotope Labelled (SIL) peptide generated by proteolysis of a labeled anti-TNF antibody (SIL anti-TNF antibody) used as an Internal Standard compound, due to a sufficient mass increment relative to the same but unlabeled peptide (i.e. an unlabeled peptide generated by proteolysis of the corresponding unlabeled anti-TNF antibody initially present in the test sample), is thus discriminated from the said unlabeled proteolysis peptide by mass spectrometry analysis.

Thus, a Stable Isotope Labelled peptide selected in a group comprising the surrogate peptides of SEQ ID NO 1-8 (for Infliximab), 9-15 (for Etanercept), 16-23 (for Adalimumab), 24-30 (for Certolizumab) or 31-35 (for Golimumab) is discriminated by mass spectrometry analysis, from the non-labelled surrogate peptides of the same respective amino acid sequences that are generated upon trypsin treatment of Infliximab, Etanercept, Adalimumab, Certolizumab or Golimumab, respectively.

Also, a Stable Isotope Labelled peptide selected in a group comprising the surrogate peptides of SEQ ID NO 38-39 (for Infliximab), 40 (for Etanercept), 41-42 (for Adalimumab), 43-44 (for Certolizumab) or 45-46 (for Golimumab) is discriminated by mass spectrometry analysis, from the non-labelled surrogate peptides of the same respective amino acid sequences that are generated upon IdeS treatment of Infliximab, Etanercept, Adalimumab, Certolizumab or Golimumab, respectively.

Stable Isotope Labelled (SIL) anti-TNF antibodies are, notably, commercially available.

Illustratively, the SIL peptides may be obtained from JPT Peptide Technologies GmbH (Berlin, Germany) or from Sigma-Aldrich (Saint Quentin Fallavier, France) under the name Aqua™ peptides.

In particular, Stable Isotope Labelled (SIL) therapeutic antibodies are available from the French Company Promise Advanced Proteomics (Grenoble, France).

Generating a Calibration Curve

The precise quantification of anti-TNF antibodies by mass spectrometric analysis is allowed by the use of at least an Internal Standard compound for each anti-TNF antibody of interest, the presence of which in combination with the said antibody of interest in a human sample permits the calculation of ratio values between (i) the spectrometry signal generated by a selected proteolysis surrogate peptide derived from a specific therapeutic anti-TNF antibody and (ii) the spectrometry signal generated by a corresponding selected labeled surrogate peptide generated by enzyme proteolysis treatment of a labeled form of the said anti-TNF antibody.

As it will be further detailed in the present specification, the quantification of anti-TNF antibodies is performed by reporting the ratio value calculated for each proteolysis peptide considered in the human sample tested, or test sample, to a calibration curve of ratio values generated, for each therapeutic anti-TNF antibody of interest, with known amounts of the said therapeutic anti-TNF antibody of interest and fixed and known amounts of a labeled form of the said anti-TNF antibody that is used as an Internal Standard compound.

For generating a calibration curve, a serial or set of calibration samples (CS) are prepared, wherein:
each calibration sample contains a known amount of the selected anti-TNF antibody, most preferably a known amount of an anti-TNF antibody selected in a group comprising Infliximab, Etanercept, Adalimumab, Certolizumab and Golimumab, each calibration sample contains a fixed and known amount of a labeled form of the said anti-TNF antibody used as an Internal Standard compound, most preferably a fixed and known amount of a labeled form of the said selected anti-TNF antibody used as an Internal Standard Compound selected in a group comprising Infliximab, Etanercept, Adalimumab, Certolizumab and Golimumab, and the serial or set of calibration samples are prepared so as to cover an amount range of the anti-TNF antibodies encompassing at least the amount range of the anti-TNF antibody(ies) which is(are) expected to be contained in a test sample.

For the sake of clarity, each calibration sample comprises the same fixed and known amount of the selected Internal Standard compound.

Illustratively, the amount range of the selected anti-TNF antibody which is covered by the serial or set of calibration samples, when expressed as a final concentration in the calibration samples, may range from 0.1 µg/mL to 100 µg/mL. For example, a serial or set of calibration samples may comprise eight calibration samples comprising an anti-TNF antibody of interest at respective final concentrations of 0.1 µg/mL, 0.5 µg/mL, 1 µg/mL, 5 µg/mL, 10 µg/mL, 20 µg/mL, 25 µg/mL, 50 µg/mL, 75 µg/mL and 100 µg/mL.

Thus, according to the anti-TNF antibody quantification method described herein, a calibration curve may be generated for each of the anti-TNF antibody of interest, and more precisely for each anti-TNF antibody selected in a group comprising Infliximab, Etanercept, Adalimumab, Certolizumab and Golimumab.

In other embodiments, a calibration curve may be generated simultaneously for a plurality of anti-TNF antibodies, especially for a plurality of anti-TNF antibodies selected in a group comprising Infliximab, Etanercept, Adalimumab, Certolizumab and Golimumab. According to these embodiments, a serial of calibration samples, each calibration sample containing (i) a plurality of non-labeled anti-TNF antibodies, especially for a plurality of anti-TNF antibodies selected in a group comprising Infliximab, Etanercept, Adalimumab, Certolizumab and Golimumab, each anti-TNF antibody being at a given concentration, and (ii) the corresponding labeled form (most preferably SIL antibodies) of each of the said anti-TNF antibody at a fixed concentration, and wherein, the serial of calibration samples covers a range of concentrations (e.g. 0;1 µg/mL to 100 µg/mL) of the said non-labeled anti-TNF antibodies, and wherein the same fixed concentration of the corresponding labeled anti-TNF antibodies is present in each of the calibration sample (e.g. a fixed concentration of 20 µg/mL of each of the labeled anti-TNF antibody).

Illustratively, the given amount of the selected labeled anti-TNF antibody used as an Internal Standard compound, especially the given amount of labeled antibody selected in a group comprising Infliximab, Etanercept, Adalimumab, Certolizumab and Golimumab, is preferably an amount which generates a mass spectrometry signal of the same order of magnitude as a mid-range calibration standard of the corresponding therapeutic anti-TNF antibody in order to limit the difference in mass spectrometry signal intensity generated by the respective amounts (i) of labeled surrogate peptides derived from enzyme proteolysis of the said labeled anti-TNF antibody used as the Internal Standard compound and (ii) of the corresponding proteolysis peptides derived from the said therapeutic anti-TNF antibody. Illustratively, the amount ratios (e.g. as expressed as weight amount or as weight/volume amounts) between a non-labeled anti-TNF antibody and the corresponding labeled anti-TNF antibody may range from 1:10 to 10:1, which encompasses amount ratios ranging from 1:5 to 5:1.

Indeed, the amount of anti-TNF antibodies that may be found in a test sample, especially in a test sample consisting of a human serum sample originating from a patient treated by anti-TNF antibodies, may vary, depending of (i) the amount of anti-TNF antibody(ies) which has(have) been administered to the said patient, (ii) the time period when the serum sample has been collected since the starting time period of the treatment, (ii) the time period of collection of the serum sample since the last administration of anti-TNF antibodies, and (iv) physiological parameters which may be specific to the said patient, such as the rate of clearance of the said antibodies from the blood.

In some embodiments, the serial or set of calibration samples may further comprise one or more control calibration samples which do not contain the selected anti-TNF antibody, or alternatively which do not contain any anti-TNF antibody.

Most preferably, a calibration sample is prepared starting from a body fluid sample initially exempt of the selected anti-TNF antibody or of the selected Internal Standard compound, and preferably serum or plasma from a non-human mammal or from a human individual, and most preferably human serum or human plasma.

Then, each of the calibration sample is subjected to the same method steps as that which is described for the test samples elsewhere in the present specification, so as to provide a serial or a set of calibration assay samples (CAS).

Then, each calibration assay sample is subjected to spectrometric analysis, and most preferably to a LC-MS/MS analysis, in the same conditions as those described for the test samples elsewhere in the present specification and the values of the spectrometry signals generated by (i) a selected surrogate peptide generated by enzyme proteolysis of the selected anti-TNF antibody and (ii) by the corresponding selected labeled peptide (also termed "labeled surrogate peptide") generated by enzyme proteolysis of the selected labeled anti-TNF antibody, especially by the corresponding selected peptide (also termed "labeled surrogate peptide") generated by enzyme proteolysis of the selected labeled anti-TNF antibody selected in a group comprising Infliximab, Etanercept, Adalimumab, Certolizumab and Golimumab, used as the Internal Standard compound, are then measured.

Then, for each of the calibration assay sample (CAS), a ratio of (i) the spectrometry signal value generated by the selected anti-TNF antibody surrogate peptide to (ii) the spectrometry signal value generated by the selected Internal Standard-derived labeled surrogate peptide is calculated.

As it will be further detailed in the present specification, a spectrometric signal value may consist of the peak area of specific SRM (Selected Reaction Monitoring) transitions, or more precisely of the mean of the peak areas of specific SRM, generated by a selected peptide of interest, typically by a selected surrogate tryptic peptide derived from the selected labeled anti-TNF antibody used as an Internal Standard described herein.

Thus, it is provided a serial or a set of ratio values, each ratio value being calculated from a calibration assay sample obtained from a starting calibration sample comprising known amounts, e.g. known final concentrations, of the selected anti-TNF antibody and a fixed and known amount of the Internal Standard compound.

A calibration curve may then be generated by plotting the serial or set of calculated ratio values versus the corresponding theoretical amounts of the selected anti-TNF antibody, e.g. versus the corresponding known final concentrations of the selected anti-TNF antibody.

As used herein, a "final" concentration of a selected anti-TNF antibody is the concentration of the said anti-TNF antibody in an initial Calibration Sample (CS), which CS comprises a known added amount of the said anti-TNF antibody.

Sample Preparation

In some embodiments, the sample which is used in the quantification method originates from a whole human blood sample that has been previously collected from an individual. In preferred embodiments, the blood cells, and especially erythrocytes, are removed by centrifugation so as to obtain a plasma sample. In other preferred embodiments, coagulation of the whole blood sample is allowed to occur and a serum sample is obtained.

In further embodiments, the sample which is used in the quantification method may consist of other extracellular fluids such as lymphatic fluid (endolymph or perilymph) and interstitial fluid.

Most preferably, at least for determining the pharmacokinetic profile of anti-TNF antibodies in an individual, the said sample is a blood plasma sample or a blood serum sample, or a sample derived from blood plasma or blood serum.

In some embodiments, the initial sample may be subjected to dilution, e.g. in an aqueous medium such as in a saline solution or in a buffer solution, before being used as the assay sample in the anti-TNF antibodies quantification method according to the invention.

However, in the most preferred embodiments, the initial sample, such as a plasma sample or a serum sample, is used without any pre-treatment and in particular is used as such undiluted.

As it will be described further in the present specification, according to the anti-TNF antibody quantification method described herein, the sample to be tested is added with a known amount of each of the two or more of the selected labeled anti-TNF antibodies used as Internal Standard compounds at step a).

In these embodiments, there is thus provided a sample containing a known amount of each of the two or more of the selected labeled anti-TNF antibodies used as Internal Standard compounds and an unknown amount of anti-TNF antibodies.

In some embodiments, the said sample comprises only two Internal Standard compounds, which are selected among anti-TNF antibodies of interest, and most preferably only two Internal Standard compounds, which are selected in a group comprising labeled Infliximab, labeled Etanercept, labeled Adalimumab, labeled Certolizumab and labeled Golimumab.

In other embodiments, the said sample comprises more than two Internal Standard compounds, which are selected among anti-TNF antibodies of interest and most preferably more than two Internal Standard compounds, which are selected in a group comprising labeled Infliximab, labeled Etanercept, labeled Adalimumab, labeled Certolizumab and labeled Golimumab. These other embodiments encompass those wherein the said sample comprises 3, 4 or 5 Internal Standard compounds, which are selected among anti-TNF antibodies of interest and most preferably 3, 4 or 5 Internal Standard compounds, which are selected in a group comprising labeled Infliximab, labeled Etanercept, labeled Adalimumab, labeled Certolizumab and labeled Golimumab. The various combinations of Internal Standard compounds that are added (or "spiked") are described elsewhere in the present specification.

The Internal Standard compounds are subjected to each of the further steps of the anti-TNF quantification method described herein.

In some embodiments of the anti-TNF quantification method described herein, step a) comprises the following steps:

a1) adding to a test sample a known amount of two or more labeled anti-TNF antibodies selected in a group comprising Infliximab, Etanercept, Adalimumab, Certolizumab and Golimumab, whereby a non-concentrated pre-proteolysis sample is provided, and a2) enriching the non-concentrated pre-proteolysis sample in antibodies, whereby a pre-proteolysis sample is provided.

Pre-Proteolysis Mixture Preparation

At step a), or alternatively at step a2), there is thus provided a pre-proteolysis mixture containing a known amount of Internal Standard compounds and an unknown amount of anti-TNF antibodies.

In some most preferred embodiments, the said pre-proteolysis mixture comprises two or more labeled anti-TNF antibodies selected in a group comprising Infliximab, Etanercept, Adalimumab, Certolizumab and Golimumab, as Internal Standard compounds.

Enriching the Sample in Anti-TNF Antibodies

In some embodiments of the anti-TNF antibodies quantification method described herein, step a), or alternatively step a2), may consist of a step wherein the enrichment in anti-TNF antibodies is performed by immunocapture, that is by complexing the anti-TNF antibodies possibly present in the test sample with TNF alpha molecules, and wherein reversible complexes formed between the anti-TNF antibodies and the TNF alpha molecules may be purified and the complexed anti-TNF antibodies may be dissociated and harvested.

These embodiments of step a), or step a2), of the quantification method may be performed by any method known in the art, which includes affinity chromatography and immunocapture. Affinity chromatography and immunocapture are both based on the same technical principle of binding and eluate the anti-TNF antibodies by using a substrate wherein anti-TNF antibodies ligands are immobilized, preferably a substrate wherein TNF alpha molecules are immobilized.

Enriching the Sample in Anti-TNF Antibodies by Immunocapture

In some embodiments illustrated in the examples herein, the test sample is enriched in anti-TNF antibodies by using a method of immunocapture. According to these embodiments, enriching in anti-TNF antibodies by depletion in non-antibody proteins is performed by using an affinity chromatography support onto which TNF alpha molecules are immobilized. More precisely, according to this method, biotinylated TNF alpha is immobilized on a support and the resulting support is brought into contact with to the previously spiked test sample so as to capture the TNF binding molecules that are present in the spiked test sample, which includes (i) the two or more Stable Isotope Labeled (SIL) anti-TNF antibodies used as Internal Standards and (ii) the other anti-TNF antibodies that are possibly present in the test sample before spiking with the SIL anti-TNF antibodies.

Then, the anti-TNF antibodies are eluted from the chromatographic support and collected for further processing.

In some preferred embodiments, it is made use of a Reverse Mass Spectrometry Immuno-Assay (MSIA) method such as that which is termed D.A.R.T.s which employs reagents, including streptavidin-coated substrate that is commercialized by the Company Thermo Scientific (San Diego, USA).

In some other preferred embodiments, immunocapture may be performed by using the streptavidin-coated beads commercialized under the name of Dynabeads™, such as Dynabeads™ M-280 Streptavidin commercialized by the Company InVitrogen (Cergy-Pontoise, France).

Enriching in Anti-TNF Antibodies by Depletion in Non-Antibody Protein

In some embodiments, of the anti-TNF antibodies quantification method described herein, step a), or alternatively step a2), may consist of a step wherein the enrichment in anti-TNF antibodies is performed by depletion of a substantial part of the proteins, except the antibody proteins, that are initially contained in the test sample.

The step of depletion of said substantial part of the proteins may consist of a protein depletion step, such as a protein differential depletion step, and preferably of an albumin depletion step.

In some embodiments of the therapeutic antibody quantification method described herein, the non-concentrated proteolysis sample is subjected to a protein depletion step.

In some embodiments of the therapeutic antibody quantification method described herein, the non-concentrated proteolysis sample is subjected to a protein differential depletion step.

A differential depletion step may refer, preferably, to a differential precipitation of proteins distinct from albumin, according to their structural and biochemical characteristics. For instance, a differential depletion step may consist in precipitating only antibodies of a certain isotope, such as IgG antibodies; or may consist in precipitating only proteins of a certain size (or range of size), such as proteins of a size lower than 80 kDa, or alternatively higher than 80 kDa.

A differential depletion step may provide a final sample which contains essentially the protein(s) of interest (i.e. antibodies), and to discard protein(s) not of interest in order to obtain a higher sensitivity than by depleting albumin only.

However, general enrichment in IgG antibodies by using a method of precipitation of plasma proteins possesses several drawbacks. Such a method for general precipitation of plasma proteins, although it is simple, fast, inexpensive and allows access to the measurement of total protein fraction, the resulting plasma proteins-enriched mixture is not sufficiently enriched in IgG, which is detrimental to the repeatability of the subsequent step of trypsin proteolysis, and finally be detrimental to the accuracy of the anti-TNF antibody quantification method. Consequently, although such a precipitation method may be used for performing the anti-TNF antibodies quantification method described herein, such an embodiment of sample preparation is not the most preferred.

According to some aspects of these embodiments, depletion in non-antibody proteins may be performed by using specific resins having affinity for proteins that are known in the art, such as the Cibacron-blue resin, which includes the Cibacron-blue™ 3 GA agarose commercialized notably by the Company Sigma-Aldrich (MI, USA).

According to some other aspects of these embodiments, depletion in non-antibody proteins may be performed by precipitation of a substantial part of the proteins initially contained in the test sample, except the antibody proteins.

In some embodiments of the quantification method described herein, the sample, optionally comprising the Internal Standard compound, is enriched in IgG antibodies.

Various methods for enriching a sample in IgG antibodies are known in the art.

In some embodiments, enrichment in IgG antibodies may be performed by ammonium sulfate precipitation, by using methods well known in the art, so as to obtain an IgG-enriched composition.

According to further aspects of these embodiments, depletion in non-antibody proteins may be performed by precipitation of the antibody proteins initially contained in the test sample, such as by performing antibody precipitation with ammonium sulfate, e.g. by using a saturated ammonium sulfate solution (30% v/v).

Protein A Chromatography

In some embodiments of the quantification method described herein, the sample, optionally comprising the Internal Standard compound, is enriched in IgG antibodies.

In some embodiments, enrichment in IgG antibodies may be performed by affinity chromatography, which includes the use of chromatography substrates onto which have been immobilized relevant ligands such as protein A, protein G or alternatively antibodies binding to the Fc portion of IgG antibodies, as well as nucleic acid or peptide aptamers that bind to the Fc portion of IgG antibodies.

The step of enrichment in IgG antibodies allows separating antibodies from other abundant plasma proteins and thus contributes to improve sensitivity and reproducibility of the anti-TNF antibody quantification method.

Preferably herein, enrichment in IgG antibodies by using protein A or protein G chromatography is preferred.

IgG enrichment by subjecting the sample to protein A or protein G chromatography allows depletion of almost the whole plasma proteins while retaining the whole IgG antibodies initially contained therein, which includes the whole anti-TNF antibodies initially contained therein.

Most preferably, enrichment in IgG antibodies is performed by protein A chromatography.

In the embodiments wherein protein A chromatography is used, elution of the retained IgG antibodies is conventionally performed at an acidic pH, generally at a pH in the range of 2-3, preferably at a pH of 2.8. Then, the fraction containing the most part of the IgG antibodies may be collected by elution using a formic acid solution (0.5%-1% v/v) at a pH ranging from 1 to 3. After evaporation of the formic acid, the dry sample may be resuspended in a liquid medium containing ammonium bicarbonate at a pH ranging from 7 to 8, for further processing.

In these embodiments, there is thus provided an IgG-enriched composition containing a known amount of the Internal Standard compounds and an unknown amount of anti-TNF antibodies.

Concentrating the IgG-Enriched Composition

In some embodiments, and especially in embodiments wherein the IgG-enriched composition is obtained by a step of chromatography wherein sample dilution is susceptible to occur, the said composition is then subjected to a concentration step, so as to provide a concentrated IgG-enriched composition.

In these embodiments, the concentration step may be performed by any method known in the art, including dialysis and filtration, e.g. microfiltration or ultrafiltration.

In preferred embodiments, the concentration step is an ultrafiltration step wherein a filter membrane of a relevant cut-off value is used.

Illustratively, the ultrafiltration step may be performed by using an ultrafiltration membrane having a cut-off value of about 100 kDa.

In the embodiments wherein the concentration step is an ultrafiltration step, a buffer exchange is performed during the ultrafiltration step so as to optimize the conditions of the further steps of the method are conducted. Notably, the buffer exchange that may be performed during the ultrafiltration step allows obtaining a concentrated IgG-enriched composition in which the subsequent step of proteolysis by trypsin will be optimally realized.

Proteolysis Step

This step is step b) of the general anti-TNF antibodies quantification method described herein.

As it is described further herein, the proteolysis step consists of subjecting the pre-proteolysis mixture, containing the labeled anti-TNF antibodies (used as Internal Standard compounds) and possibly the non-labeled anti-TNF antibodies to be quantified, to an enzyme proteolysis so as to generate, notably, anti-TNF antibody-derived proteolysis peptides, namely (i) labeled anti-TNF antibody-derived proteolysis peptides generated from the tow or more Internal Standard compounds added at step a) and non-labeled anti-TNF antibody-derived proteolysis peptides generated from the non-labeled anti-TNF antibodies to be quantified, if these non-labeled anti-TNF antibodies are present initially in the test sample.

A plurality of embodiments of a proteolysis step may be performed. In particular, the proteolysis enzymes, which may also be termed proteases herein, may be selected in a vast group of proteases well known in the art. Since the cleavage site(s) of each known protease is part of the technical knowledge of the one skilled in the art, the selection of a specific protease at step b) is correlated to the subsequent monitoring of the expected resulting anti-TNF antibodies proteolysis peptides generated therefrom, by mass spectrometric analysis.

In some embodiments of the proteolysis step that are illustrated in the examples herein, the selected protease possesses trypsin activity.

In some other embodiments of the proteolysis step that are illustrated in the examples herein, the selected protease possesses a hinge-targeting activity.

One-Step Trypsin Proteolysis

According to these embodiments of the proteolysis step, trypsin is added to the pre-proteolysis mixture, so as to generate (i) tryptic peptides from the anti-TNF antibodies initially contained in the test sample and (ii) tryptic peptides generated by trypsin proteolysis of the labeled anti-TNF antibodies used as Internal Standard compounds. The specific tryptic peptides derived from the internal standard monoclonal antibody may also be termed "surrogate peptides" herein.

In some embodiments, the one-step trypsin proteolysis is performed by using trypsin as the sole added protease.

In some other embodiments that are illustrated in the examples herein, the one-step trypsin proteolysis is performed by using a combination of trypsin and endoproteinase Lys-C (also termed "EndolysC" herein) as the "protease". According to these embodiments, the combination or mixture of trypsin and endoproteinase Lys-C contains advantageously a weight amount ratio of trypsin to EndolysC ranging from 0.1:1 to 20:1, which encompasses a weight amount ratio from 0.5:1 to 15:1, preferably a weight amount ratio ranging from 1:10:1. As it is well known in the art, trypsin cleaves peptide chains mainly at the carboxyl side of the amino acids lysine and arginine, except when either is followed by proline.

As it is also well known in the art EndolysC cleaves peptide chains at the carboxyl side of lysine amino acid.

The proteolysis step is preferably performed in conditions that are optimal for:
(i) generating all the expected surrogate tryptic peptides, and
(ii) avoiding trypsin autolysis.

It may be used a purified trypsin having a low ability to autolysis. Illustratively, it may be used a trypsin termed Trypsin Gold® which is marketed by the company Promega (Madison, Wis., United States).

Optimal proteolysis conditions may be reached by using a trypsin/total protein molar ratio ranging from 1/100 to 1/1.

In most preferred embodiments, the proteolysis step is performed in non-denaturing conditions, i.e. in conditions which do not cause protein denaturation. Notably, the proteolysis step is performed in the absence of a protein denaturation agent such as urea or guanidium hydrochloride.

Proteolysis in the presence of trypsin is performed during a period of time that may be optimally adapted by the one skilled in the art.

Advantageously, proteolysis is performed at 37° C. during a period of time ranging from 0.5 hour to 15 hours, preferably from 1 hour to 10 hours, and most preferably ranging from 2 hours to 4 hours. In some embodiments, proteolysis is performed at 37° C. overnight.

The one-step proteolysis step is performed at a pH of 6 or more. Further, the one-step proteolysis step is advantageously performed at a pH of less than 8.5, preferably at a pH of 8 or less, which includes at a pH of 7.5 or less, e.g. at a pH of about 7.

In most preferred embodiments, the one-step proteolysis step is performed under non-denaturing conditions, that is under conditions wherein there is no denaturation of the proteins initially contained in the pre-proteolysis sample.

In some embodiments, proteolysis is stopped by acidification of the resulting mixture, for example by adding an appropriate acid such as formic acid, so as to decrease the pH of the said resulting mixture below pH 6.

Two-Step Trypsin Proteolysis

In some embodiments, step b) may be performed by a two-step trypsin proteolysis. In these embodiments, step b) comprises two enzyme proteolysis steps, namely step b1) of enzyme proteolysis under denaturing conditions and step b2) of enzyme proteolysis in non-denaturing conditions, as it is illustrated in the examples herein.

The enzyme(s) which is used at steps b1) and b2) may be the same as those disclosed for performing the "one-step trypsin proteolysis" specified above.

In some embodiments, the enzyme(s) which is(are) used at step b1) is(are) the same as that(those) which is(are) used at step b2). In some other embodiments, the enzyme(s) which is(are) used at step b1) is(are) distinct from that (those) which is(are) used ate step b2).

According to the two-step proteolysis method, step b1) consists of a pre-digestion step wherein aimed at increasing the sensitivity of the proteins contained in the pre-proteolysis sample, and mainly the trypsin sensitivity of the antibodies (including the anti-TNF antibodies) contained in the pre-proteolysis sample.

Step b1) is performed in denaturing conditions, such that in the presence of urea, advantageously at a final concentration ranging from 4 M to 0.1 M, preferably at a final concentration of about 4 M.

In some embodiments, step b1) is performed by using a protease mixture of EndolysC and trypsin in an amount as described of the "one-step trypsin proteolysis" embodiment above.

In some other embodiments, step b1) is performed by using Endolys C as the sole protease. According to these other embodiments, EndolysC is present in the resulting sample at a final concentration ranging from 0.01 µg/mL to 10 µg/mL.

At step b1) proteolysis is performed during a time period of 0.5 h to 6 h; advantageously from 0.75 h to 4 h, preferably from 1 h to 3 h, and may be performed during a time period of about 2 h.

At step b1) proteolysis is preferably performed at 37° C.

At step b1) proteolysis is performed at a pH of 6 or more. Further, the one-step proteolysis step is advantageously performed at a pH of less than 8.5, preferably at a pH of 8 or less, which includes at a pH of 7.5 or less, e.g. at a pH of about 7.

Further, step b2) is performed by using a protease mixture comprising trypsin.

In some embodiments, step b2) is performed by using a protease mixture of EndolysC and trypsin in an amount as described of the "one-step trypsin proteolysis" embodiment above. In some aspects of these embodiments, the protease mixture of EndolysC and trypsin is added at step b1) and there is preferably no addition of further protease or protease mixture at step b2) since the said protease or protease mixture is already present at the appropriate final concentration in the pre-digestion sample obtained at the end of step b1). According to these embodiments, step b1) may performed in conditions wherein EndolysC is active and trypsin is inactive, and wherein trypsin is rendered active at step b2) by bringing changes in the sample physico-chemical conditions such that by adding an appropriate buffer composition at the beginning of step b2). Illustratively, ammonium bicarbonate buffer solution at an appropriate final concentration may be added at the beginning of step b2).

In some other aspects of these embodiments wherein step b1) is performed by using EndolysC, an appropriate amount of trypsin is added at the beginning of step b2), so that the sample used at the beginning of step b2) comprises a protease mixture of EndolysC and trypsin, at the desired ratio and final concentration.

In some other embodiments, step b1) is performed by using trypsin as the sole added protease. According to these other embodiments, there is preferably no further addition of trypsin at step b2).

Advantageously, proteolysis at step b2) is performed at 37° C. during a period of time ranging from 0.5 hour to 15 hours, preferably from 1 hour to 10 hours, and most preferably ranging from 2 hours to 4 hours. In some embodiments, proteolysis is performed at 37° C. overnight.

The one-step proteolysis at step b2) is performed at a pH of 6 or more. Further, the one-step proteolysis step is advantageously performed at a pH of less than 8.5, preferably at a pH of 8 or less, which includes at a pH of 7.5 or less, e.g. at a pH of about 7.

Proteolysis with a Hinge-Targeting Protease

In some embodiments of step b), proteolysis is performed by using a hinge-targeting protease. Hinge-targeting proteases are known proteases effecting a cleavage in an antibody protein in the hinge region so as to generate (i) two Fc regions of the heavy chains and (ii) an F(ab')$_2$ moiety, respectively. Fab moieties may then be obtained from the F(ab')$_2$ moiety, by methods well known form the one skilled in the art, such as by using a reducing agent such as dithiothreitol (DTT).

At step b), the hinge-targeting protease is preferably selected in a group comprising Gelatinase A (MMP-2) (Tamerius et al., 1975, Int J Cancer, Vol. 16: 456-464), Stromyelysin (MMP-3) (Tamerius et al., 1975, Int J Cancer, Vol. 16: 456-464; Tamerius et al., 1976, J Immunol, Vol. 116: 724-730; Reichert et al., 2010, Mabs, Vol. 2: 84-100), Matrilysin (MMP-7) (Tamerius et al., 1975, Int J Cancer, Vol. 16: 456-464; Tamerius et al., 1976, J Immunol, Vol. 116: 724-730; Reichert et al., 2010, Mabs, Vol. 2: 84-100), Gelatinase B (MMP-9) (Reichert et al., 2010, Mabs, Vol. 2: 84-100), Macrophage metalloelastase (MMP-12) (Tamerius et al., 1976, J Immunol, Vol. 116: 724-730; Reichert et al., 2010, Mabs, Vol. 2: 84-100), Collagenase-3 (MMP-13) (Tamerius et al., 1976, J Immunol, Vol. 116: 724-730), Cathepsin G (Reichert et al., 2010, Mabs, Vol. 2: 84-100), Pseudolysin (Strohl et al., 2009, Curr Opinion Biotechnol, Vol. 20: 685-691), Mirabilysin, Glutamyl endopeptidase I (GluV8) (Tamerius et al., 1976, J Immunol, Vol. 116: 724-730; Reichert et al., 2010, Mabs, Vol. 2: 84-100), Streptopain (SpeB) (Brezski et al., 2010, mAbs, Vol. 2:3: 212-220), Trepolisin (Brerski et al., 2010, mAbs, Vol. 2:3: 212-220) and Immunoglobulin-degrading enzyme from *Streptococcus* (ideS) (Tamerius et al., 1976, J Immunol, Vol. 116: 724-730; Reichert et al., 2010, Mabs, Vol. 2: 84-100).

Most preferably, these embodiments of step b) are performed by using Immunoglobulin-degrading enzyme from *Streptococcus* (ideS) as the hinge-targeting protease. In these embodiments, it may be used ideS which is immobilized on an appropriate solid support, e.g. an agarose support, such as in the FragIT™ kit commercialized by the Company Genovis (Luna, Sweden) or the Company Sigma-Aldrich (Saint Louis, Mo., United States).

At step b) the pre-proteolysis sample is subjected to proteolysis with an ideS protease at room temperature during a time period ranging from 5 mins to 96 hours, advantageously from 10 mins to 50 hours, which includes a time period ranging from 1 hour to 5 hours.

The resulting proteolysis mixture may be collected by centrifugation and/or protein precipitation, before-suspension, as it is illustrated in the examples herein.

Quantification of Anti-TNF Antibodies by Mass Spectrometric Analysis

This step encompasses steps c) and d) of the general anti-TNF antibodies quantification method described herein.

Step c) is performed by mass spectrometry, according to techniques of protein quantification by mass spectrometry that are known in the art.

Preferably, step c) is performed according to the method of Liquid Chromatography coupled to tandem Mass Spectrometry (LC-MS/MS), as it is shown in the examples herein.

Preferably, it is used a triple quadrupole (QqQ) mass spectrometer equipped with an ESI source operating in positive ion mode and using multiple reaction monitoring (MRM) mode for quantification.

In some embodiments, Liquid Chromatography is performed with a reverse phase chromatography substrate.

Then, in some embodiments, the most abundant state of charge of (i) selected surrogate proteolytic peptides derived from the labeled anti-TNF antibodies used as Internal Standard compounds and of (ii) the proteolytic peptides derived from the anti-TNF antibodies initially present in the test sample are observed preferably between 200 m/z and 2000 m/z in ESI ionization source and are selected and fragmented.

At the quantification step by mass spectrometry, it is researched the Selected Reaction Monitoring (SRM) transitions specific of
(i) the selected surrogate proteolytic peptide(s) of an anti-TNF antibody and of
(ii) the corresponding labeled proteolytic peptide derived from the corresponding labeled anti-TNF antibody used as one of the Internal Standard compounds.

As already mentioned elsewhere in the present specification, performing the anti-TNF antibodies quantification method of the invention wherein the proteolysis step b) makes use of trypsin as the sole protease or as a protease contained in a protease mixture, the one or more selected proteolysis peptides are selected in a group comprising:
for Infliximab: peptides of SEQ ID NO. 1-8,
for Etanercept: peptides of SEQ ID NO. 9-15,
for Adalimumab: peptides of SEQ ID NO. 16-23,
for Certolizumab: peptides of SEQ ID NO. 24-30, and
for Golimumab: peptides of SEQ ID NO. 31-37.

In the embodiments wherein the proteolysis step is performed by using trypsin or a trypsin-containing protease composition and wherein a labeled counterpart of Infliximab is used as an Internal Standard compound, the number of selected proteolysis peptides for which a mass spectrometric signal ratio is determined at step c) may vary from 1 to 8, which encompasses 1, 2, 3, 4, 5, 6, 7 and 8 selected proteolysis peptides.

In the embodiments wherein two selected proteolysis peptides are monitored, these may be selected in a group comprising SEQ ID NO. 1 and 2; SEQ ID NO. 1 and 3; SEQ ID NO. 1 and 4; SEQ ID NO. 1 and 5; SEQ ID NO. 1 and 6; SEQ ID NO. 1 and 7; SEQ ID NO. 1 and 8; SEQ ID NO. 2 and 3; SEQ ID NO. 2 and 4; SEQ ID NO. 2 and 5; SEQ ID NO. 2 and 6; SEQ ID NO. 2 and 7; SEQ ID NO. 2 and 8; SEQ ID NO. 3 and 4; SEQ ID NO. 3 and 5; SEQ ID NO. 3 and 6; SEQ ID NO. 3 and 7; SEQ ID NO. 3 and 8; SEQ ID NO. 4 and 5; SEQ ID NO. 4 and 6; SEQ ID NO. 4 and 7; SEQ ID NO. 4 and 8; SEQ ID NO. 5 and 6; SEQ ID NO. 5 and 7; SEQ ID NO. 5 and 8; SEQ ID NO. 6 and 7; and SEQ ID NO. 7 and 8.

In the embodiments wherein three selected proteolysis peptides are monitored, these may be selected in a group comprising SEQ ID NO. 1, 2 and 3; SEQ ID NO. 1, 2 and 4; SEQ ID NO. 1, 2 and 5; SEQ ID NO. 1, 2 and 6; SEQ ID NO. 1, 2 and 7; SEQ ID NO. 1, 2 and 8; SEQ ID NO. 1, 3 and 4; SEQ ID NO. 1, 3 and 5; SEQ ID NO. 1, 3 and 6; SEQ ID NO. 1; 3 and 7; SEQ ID NO. 1, 3 and 8; SEQ ID NO. 1, 4 and 5; SEQ ID NO. 1, 4 and 6; SEQ ID NO. 1, 4 and 7; SEQ ID NO. 1; 4 and 8; SEQ ID NO. 1; 5 and 6; SEQ ID NO. 1, 5 and 7; SEQ ID NO. 1, 5 and 8; SEQ ID NO. 1; 6 and 7; SEQ ID NO. 1, 6 and 8; SEQ ID NO. 1, 7 and 8; SEQ ID NO. 2, 3 and 4; SEQ ID NO. 2, 3 and 5; SEQ ID NO. 2, 3 and 6; SEQ ID NO. 2, 3 and 7; SEQ ID NO. 2, 3 and 8; SEQ ID NO. 2, 4 and 5; SEQ ID NO. 2, 4 and 6; SEQ ID NO. 2, 4 and 7; SEQ ID NO. 2, 4 and 8; SEQ ID NO. 2, 5 and 6; SEQ ID NO. 2, 5 and 7; SEQ ID NO. 2, 5 and 8; SEQ ID NO. 2, 6 and 7; SEQ ID NO. 2, 6 and 8; SEQ ID NO. 2, 7 and 8; SEQ ID NO. 3, 4, and 5; SEQ ID NO. 3, 4 and 6; SEQ ID NO. 3, 4 and 7; SEQ ID NO. 3, 4 and 8; SEQ ID NO. 3, 5 and 6, SEQ ID NO. 3, 5 and 7; SEQ ID NO. 3, 5 and 8; SEQ ID NO. 3, 6 and 7; SEQ ID NO. 3, 6 and 8, SEQ ID NO. 3, 7 and 8; SEQ ID NO. 4, 5 and 6; SEQ ID NO. 4, 5 and 7; SEQ ID NO. 4, 5 and 8; SEQ ID NO. 4, 6 and 7; SEQ ID NO. 4, 6 and 8; SEQ ID NO. 4, 7 and 8; SEQ ID NO. 5, 6 and 7; SEQ ID NO. 5, 6 and 8; SEQ ID NO. 5, 7 and 8; SEQ ID NO. 6, 7 and 8.

In the embodiments wherein four selected proteolysis peptides are monitored, these may be selected in a group comprising SEQ ID NO. 1, 2, 3 and 4; SEQ ID NO. 1, 2 3 and 5; SEQ ID NO. 1, 2, 3, and 6; SEQ ID NO. 1, 2, 3 and 7; SEQ ID NO. 1, 2, 3 and 8; SEQ ID NO. 1, 3, 4 and 5; SEQ ID NO. 1, 3, 4 and 6; SEQ ID NO. 1, 3, 4 and 7; SEQ ID NO. 1, 3, 4 and 8; SEQ ID NO. 1, 4, 5 and 6; SEQ ID NO. 1, 4, 5 and 7; SEQ ID NO. 1, 4, 5 and 8; SEQ ID NO. 1, 5, 6 and 7; SEQ ID NO. 1, 5, 6 and 8; SEQ ID NO. 1, 5, 7 and 8; SEQ ID NO. 2, 3, 4 and 5; SEQ ID NO. 2, 3, 4 and 6; SEQ ID NO. 2, 3, 4 and 7; SEQ ID NO. 2, 3, 4 and 8; SEQ ID NO. 2, 4, 5 and 6; SEQ ID NO. 2, 4, 5 and 7; SEQ ID NO. 2, 4, 5 and 8; SEQ ID NO. 2, 5, 6 and 7; SEQ ID NO. 2, 5, 6 and 8; SEQ ID NO. 2, 6, 7 and 8; SEQ ID NO. 3, 4, 5 and 6; SEQ ID NO. 3, 4, 5 and 7; SEQ ID NO. 3, 4, 5 and 8; SEQ ID NO. 3, 5, 6 and 7; SEQ ID NO. 3, 5, 7 and 8; SEQ ID NO. 3, 6, 7 and 8; SEQ ID NO. 4, 5, 6 and 7; SEQ ID NO. 4, 5, 6 and 8; SEQ ID NO. 4, 6, 7 and 8; SEQ ID NO. 5, 6, 7 and 8.

In the embodiments wherein five selected proteolysis peptides are monitored, these may be selected in a group comprising SEQ ID NO. 1, 2, 3, 4 and 5; SEQ ID NO. 1, 2, 3, 4, and 6; SEQ ID NO. 1, 2, 3, 4 and 7; SEQ ID NO. 1, 2, 3, 4 and 8; SEQ ID NO. 1, 3, 4, 5 and 6; SEQ ID NO. 1, 3, 4, 5 and 7; SEQ ID NO. 1, 3, 4, 5 and 8; SEQ ID NO. 1, 4, 5, 6 and 7; SEQ ID NO. 1, 4, 5, 6 and 8; SEQ ID NO. 1, 5, 6, 7 and 8; SEQ ID NO. 2, 3, 4, 5 and 6; SEQ ID NO. 2, 3, 4, 5 and 7; SEQ ID NO. 2, 3, 4, 5 and 8; SEQ ID NO. 2, 4, 5, 6 and 7; SEQ ID NO. 2, 4, 5, 6 and 8; SEQ ID NO. 2, 5, 6, 7 and 8; SEQ ID NO. 3, 4, 5, 6 and 7; SEQ ID NO. 3, 4, 5, 6 and 8; SEQ ID NO. 3, 5, 6, 7 and 8; SEQ ID NO. 4, 5, 6, 7 and 8.

In the embodiments wherein six selected proteolysis peptides are monitored, these may be selected in a group comprising SEQ ID NO. 1, 2, 3, 4, 5 and 6; SEQ ID NO. 1, 2, 3, 4, 5 and 7, SEQ ID NO. 1, 2, 3, 4, 5 and 8; SEQ ID NO. 1, 3, 4, 5, 6 and 7; SEQ ID NO. 1, 3, 4, 5, 6 and 8; SEQ ID NO. 1, 4, 5, 6, 7 and 8; SEQ ID NO. 2, 3, 4, 5, 6 and 7; SEQ ID NO. 2, 3, 4, 5, 6 and 8; SEQ ID NO. 2, 4, 5, 6, 7 and 8; SEQ ID NO. 3, 4, 5, 6, 7 and 8;

In the embodiments wherein seven selected proteolysis peptides are monitored, these may be selected in a group comprising SEQ ID NO. 1, 2, 3, 4, 5, 6 and 7; SEQ ID NO. 1, 2, 3, 4, 5, 6 and 8; SEQ ID NO. 1, 3, 4, 5, 6, 7 and 8; SEQ ID NO. 2, 3, 4, 5, 6, 7 and 8.

In the embodiments wherein eight selected proteolysis peptides are monitored, these may be selected in a group comprising SEQ ID NO. 1, 2, 3, 4, 5, 6, 7 and 8.

In the embodiments wherein the proteolysis step is performed by using trypsin or a trypsin-containing protease composition and wherein a labeled counterpart of Etanercept is used as an Internal Standard compound, the number of selected proteolysis peptides for which a mass spectrometric signal ratio is determined at step c) may vary from 1 to 7, which encompasses 1, 2, 3, 4, 5, 6 and 7 selected proteolysis peptides.

In the embodiments wherein two selected proteolysis peptides are monitored, these may be selected in a group comprising SEQ ID NO. 9 and 10; SEQ ID NO. 9 and 11; SEQ ID NO. 9 and 12; SEQ ID NO. 9 and 13; SEQ ID NO. 9 and 14; SEQ ID NO. 9 and 15; SEQ ID NO. 10 and 11; SEQ ID NO. 10 and 12; SEQ ID NO. 10 and 13; SEQ ID NO. 10 and 14; SEQ ID NO. 10 and 15; SEQ ID NO. 11 and 12; SEQ ID NO. 11 and 13; SEQ ID NO. 11 and 14; SEQ ID NO. 11 and 15; SEQ ID NO. 12 and 13; SEQ ID NO. 12 and 14; SEQ ID NO. 12 and 15; SEQ ID NO. 13 and 14; SEQ ID NO. 13 and 15; SEQ ID NO. 14 and 15.

In the embodiments wherein three selected proteolysis peptides are monitored, these may be selected in a group comprising SEQ ID NO. 9, 10 and 11; SEQ ID NO. 9, 10 and 12; SEQ ID NO. 9, 10 and 13; SEQ ID NO. 9, 10 and 14; SEQ ID NO. 9, 10 and 15; SEQ ID NO. 9, 11 and 12; SEQ ID NO. 9, 11 and 13; SEQ ID NO. 9, 11 and 14; SEQ ID NO. 9, 11 and 15; SEQ ID NO. 9, 12 and 13; SEQ ID NO. 9, 12 and 14; SEQ ID NO. 9, 12 and 15; SEQ ID NO. 9; 13 and 14; SEQ ID NO. 9, 13 and 15; SEQ ID NO. 9; 14 and 15; SEQ ID NO. 10, 11 and 12; SEQ ID NO. 10, 11 and 13; SEQ ID NO. 10, 11 and 14; SEQ ID NO. 10, 11 and 15; SEQ ID NO. 10, 12 and 13; SEQ ID NO. 10, 12 and 14; SEQ ID NO. 10, 12 and 15; SEQ ID NO. 10, 13 and 14; SEQ ID NO. 10, 13 and 15; SEQ ID NO. 10, 14 and 15; SEQ ID NO. 11, 12, and 13; SEQ ID NO. 11, 12 and 14; SEQ ID NO. 11, 12 and 15; SEQ ID NO. 11, 13 and 14; SEQ ID NO. 11, 13 and 15; SEQ ID NO. 11, 14 and 15; SEQ ID NO. 12, 13 and 14; SEQ ID NO. 12, 13 and 15; SEQ ID NO. 13, 14 and 15.

In the embodiments wherein four selected proteolysis peptides are monitored, these may be selected in a group comprising SEQ ID NO. 9, 10, 11 and 12; SEQ ID NO. 9, 10 11 and 13; SEQ ID NO. 9, 10, 11, and 14; SEQ ID NO. 9, 10, 11 and 15; SEQ ID NO. 9, 11, 12 and 13; SEQ ID NO. 9, 11, 12 and 14; SEQ ID NO. 9, 11, 12 and 15; SEQ ID NO. 9, 12, 13 and 14; SEQ ID NO. 9, 12, 13 and 15; SEQ ID NO. 9, 13, 14 and 15; SEQ ID NO. 10, 11, 12 and 13; SEQ ID NO. 10, 11, 12 and 14; SEQ ID NO. 10, 11, 12 and 15; SEQ ID NO. 10, 12, 13 and 14; SEQ ID NO. 10, 12, 13 and 15; SEQ ID NO. 10, 13, 14 and 15; SEQ ID NO. 11, 12, 13 and 14; SEQ ID NO. 11, 12, 13 and 15; SEQ ID NO. 11, 13, 14 and 15; SEQ ID NO. 12, 13, 14 and 15.

In the embodiments wherein five selected proteolysis peptides are monitored, these may be selected in a group comprising SEQ ID NO. 9, 10, 11, 12 and 13; SEQ ID NO. 9, 10, 11, 12, and 14; SEQ ID NO. 9, 10, 11, 12 and 15; SEQ ID NO. 9, 11, 12, 13 and 14; SEQ ID NO. 9, 11, 12, 13 and 15; SEQ ID NO. 9, 12, 13, 14 and 15; SEQ ID NO. 10, 11, 12, 13 and 14; SEQ ID NO. 10, 11, 12, 13 and 15; SEQ ID NO. 10, 12, 13, 14 and 15; SEQ ID NO. 11, 12, 13, 14 and 15.

In the embodiments wherein six selected proteolysis peptides are monitored, these may be selected in a group comprising SEQ ID NO. 9, 10, 11, 12, 13 and 14; SEQ ID NO. 9, 10, 11, 12, 13 and 15, SEQ ID NO. 9, 11, 12, 13, 14 and 15; SEQ ID NO. 10, 11, 12, 13, 14 and 15.

In the embodiments wherein seven selected proteolysis peptides are monitored, these may be selected in a group comprising SEQ ID NO. 9, 10, 11, 12, 13, 14 and 15.

In the embodiments wherein the proteolysis step is performed by using trypsin or a trypsin-containing protease composition and wherein a labeled counterpart of Adalimumab is used as an Internal Standard compound, the number of selected proteolysis peptides for which a mass spectrometric signal ratio is determined at step c) may vary from 1 to 8, which encompasses 1, 2, 3, 4, 5, 6, 7 and 8 selected proteolysis peptides.

In the embodiments wherein two selected proteolysis peptides are monitored, these may be selected in a group comprising SEQ ID NO. 16 and 17; SEQ ID NO. 16 and 18; SEQ ID NO. 16 and 19; SEQ ID NO. 16 and 20; SEQ ID NO. 16 and 21; SEQ ID NO. 16 and 22; SEQ ID NO. 16 and 23; SEQ ID NO. 17 and 18; SEQ ID NO. 17 and 19; SEQ ID NO. 17 and 20; SEQ ID NO. 17 and 21; SEQ ID NO. 17 and 22; SEQ ID NO. 17 and 23; SEQ ID NO. 18 and 19; SEQ ID NO. 18 and 20; SEQ ID NO. 18 and 21; SEQ ID NO. 18 and 22; SEQ ID NO. 18 and 23; SEQ ID NO. 19 and 20; SEQ ID NO. 19 and 21; SEQ ID NO. 19 and 22; SEQ ID NO. 19 and 23; SEQ ID NO. 20 and 21; SEQ ID NO. 20 and 22; SEQ ID NO. 20 and 23; SEQ ID NO. 21 and 22; and SEQ ID NO. 22 and 23.

In the embodiments wherein three selected proteolysis peptides are monitored, these may be selected in a group comprising SEQ ID NO. 16, 17 and 18; SEQ ID NO. 16, 17 and 19; SEQ ID NO. 16, 17 and 20; SEQ ID NO. 16, 17 and 21; SEQ ID NO. 16, 17 and 22; SEQ ID NO. 16, 17 and 23; SEQ ID NO. 16, 18 and 19; SEQ ID NO. 16, 18 and 20; SEQ ID NO. 16, 18 and 21; SEQ ID NO. 16; 18 and 22; SEQ ID NO. 16, 18 and 23; SEQ ID NO. 16, 19 and 20; SEQ ID NO. 16, 19 and 21; SEQ ID NO. 16, 19 and 22; SEQ ID NO. 16; 19 and 23; SEQ ID NO. 16; 20 and 21; SEQ ID NO. 16, 20 and 22; SEQ ID NO. 16, 20 and 23; SEQ ID NO. 16; 21 and 22; SEQ ID NO. 16, 21 and 23; SEQ ID NO. 16, 22 and 23; SEQ ID NO. 17, 18 and 19; SEQ ID NO. 17, 18 and 20; SEQ ID NO. 17, 18 and 21; SEQ ID NO. 17, 18 and 22; SEQ ID NO. 17, 18 and 23; SEQ ID NO. 17, 19 and 20; SEQ ID NO. 17, 19 and 21; SEQ ID NO. 17, 19 and 22; SEQ ID NO. 17, 19 and 23; SEQ ID NO. 17, 20 and 21; SEQ ID NO. 17, 20 and 22; SEQ ID NO. 17, 20 and 23; SEQ ID NO. 17, 21 and 22; SEQ ID NO. 17, 21 and 23; SEQ ID NO. 17, 22 and 23; SEQ ID NO. 18, 19, and 20; SEQ ID NO. 18, 19 and 21; SEQ ID NO. 18, 19 and 22; SEQ ID NO. 18, 19 and 23; SEQ ID NO. 18, 20 and 21, SEQ ID NO. 18, 20 and 22; SEQ ID NO. 18, 20 and 23; SEQ ID NO. 18, 21 and 22; SEQ ID NO. 18, 21 and 23, SEQ ID NO. 18, 22 and 23; SEQ ID NO. 19, 20 and 21; SEQ ID NO. 19, 20 and 22; SEQ ID NO. 19, 20 and 23; SEQ ID NO. 19, 21 and 22; SEQ ID NO. 19, 21 and 23; SEQ ID NO. 19, 22 and 23; SEQ ID NO. 20, 21 and 22; SEQ ID NO. 20, 21 and 23; SEQ ID NO. 20, 22 and 23; SEQ ID NO. 21, 22 and 23.

In the embodiments wherein four selected proteolysis peptides are monitored, these may be selected in a group comprising SEQ ID NO. 16, 17, 18 and 19; SEQ ID NO. 16, 17 18 and 20; SEQ ID NO. 16, 17, 18, and 21; SEQ ID NO. 16, 17, 18 and 22; SEQ ID NO. 16, 17, 18 and 23; SEQ ID NO. 16, 18, 19 and 20; SEQ ID NO. 16, 18, 19 and 21; SEQ ID NO. 16, 18, 19 and 22; SEQ ID NO. 16, 18, 19 and 23; SEQ ID NO. 16, 19, 20 and 21; SEQ ID NO. 16, 19, 20 and 22; SEQ ID NO. 16, 19, 20 and 23; SEQ ID NO. 16, 20, 21 and 22; SEQ ID NO. 16, 20, 21 and 23; SEQ ID NO. 16, 20, 22 and 23; SEQ ID NO. 17, 18, 19 and 20; SEQ ID NO. 17, 18, 19 and 21; SEQ ID NO. 17, 18, 19 and 22; SEQ ID NO. 17, 18, 19 and 23; SEQ ID NO. 17, 19, 20 and 21; SEQ ID NO. 17, 19, 20 and 22; SEQ ID NO. 17, 19, 20 and 23; SEQ ID NO. 17, 20, 21 and 22; SEQ ID NO. 17, 20, 21 and 23; SEQ ID NO. 17, 21, 22 and 23; SEQ ID NO. 18, 19, 20 and 21; SEQ ID NO. 18, 19, 20 and 22; SEQ ID NO. 18, 19, 20 and 23; SEQ ID NO. 18, 20, 21 and 22; SEQ ID NO. 18, 20, 22 and 23; SEQ ID NO. 18, 21, 22 and 23; SEQ ID NO. 19, 20, 21 and 22; SEQ ID NO. 19, 20, 21 and 23; SEQ ID NO. 19, 21, 22 and 23; SEQ ID NO. 20, 21, 22 and 23.

In the embodiments wherein five selected proteolysis peptides are monitored, these may be selected in a group comprising SEQ ID NO. 16, 17, 18, 19 and 20; SEQ ID NO. 16, 17, 18, 19, and 21; SEQ ID NO. 16, 17, 18, 19 and 22; SEQ ID NO. 16, 17, 18, 19 and 23; SEQ ID NO. 16, 18, 19, 20 and 21; SEQ ID NO. 16, 18, 19, 20 and 22; SEQ ID NO. 16, 18, 19, 20 and 23; SEQ ID NO. 16, 19, 20, 21 and 22; SEQ ID NO. 16, 19, 20, 21 and 23; SEQ ID NO. 16, 20, 21, 22 and 23; SEQ ID NO. 17, 18, 19, 20 and 21; SEQ ID NO. 17, 18, 19, 20 and 22; SEQ ID NO. 17, 18, 19, 20 and 23; SEQ ID NO. 17, 19, 20, 21 and 22; SEQ ID NO. 17, 19, 20, 21 and 23; SEQ ID NO. 17, 20, 21, 22 and 23; SEQ ID NO.

18, 19, 20, 21 and 22; SEQ ID NO. 18, 19, 20, 21 and 23; SEQ ID NO. 18, 20, 21, 22 and 23; SEQ ID NO. 19, 20, 21, 22 and 23.

In the embodiments wherein six selected proteolysis peptides are monitored, these may be selected in a group comprising SEQ ID NO. 16, 17, 18, 19, 20 and 21; SEQ ID NO. 16, 17, 18, 19, 20 and 22, SEQ ID NO. 16, 17, 18, 19, 20 and 23; SEQ ID NO. 16, 18, 19, 20, 21 and 22; SEQ ID NO. 16, 18, 19, 20, 21 and 23; SEQ ID NO. 16, 19, 20, 21, 22 and 23; SEQ ID NO. 17, 18, 19, 20, 21 and 22; SEQ ID NO. 17, 18, 19, 20, 21 and 23; SEQ ID NO. 17, 19, 20, 21, 22 and 23; SEQ ID NO. 18, 19, 20, 21, 22 and 23;

In the embodiments wherein seven selected proteolysis peptides are monitored, these may be selected in a group comprising SEQ ID NO. 16, 17, 18, 19, 20, 21 and 22; SEQ ID NO. 16, 17, 18, 19, 20, 21 and 23; SEQ ID NO. 16, 18, 19, 20, 21, 22 and 23; SEQ ID NO. 17, 18, 19, 20, 21, 22 and 23.

In the embodiments wherein eight selected proteolysis peptides are monitored, these may be selected in a group comprising SEQ ID NO. 16, 17, 18, 19, 20, 21, 22 and 23.

In the embodiments wherein the proteolysis step is performed by using trypsin or a trypsin-containing protease composition and wherein a labeled counterpart of Certolizumab is used as an Internal Standard compound, the number of selected proteolysis peptides for which a mass spectrometric signal ratio is determined at step c) may vary from 1 to 7, which encompasses 1, 2, 3, 4, 5, 6 and 7 selected proteolysis peptides.

In the embodiments wherein two selected proteolysis peptides are monitored, these may be selected in a group comprising SEQ ID NO. 24 and 25; SEQ ID NO. 24 and 26; SEQ ID NO. 24 and 27; SEQ ID NO. 24 and 28; SEQ ID NO. 24 and 29; SEQ ID NO. 24 and 30; SEQ ID NO. 25 and 26; SEQ ID NO. 25 and 27; SEQ ID NO. 25 and 28; SEQ ID NO. 25 and 29; SEQ ID NO. 25 and 30; SEQ ID NO. 26 and 27; SEQ ID NO. 26 and 28; SEQ ID NO. 26 and 29; SEQ ID NO. 26 and 30; SEQ ID NO. 27 and 28; SEQ ID NO. 27 and 29; SEQ ID NO. 27 and 30; SEQ ID NO. 28 and 29; SEQ ID NO. 28 and 30; SEQ ID NO. 29 and 30.

In the embodiments wherein three selected proteolysis peptides are monitored, these may be selected in a group comprising SEQ ID NO. 24, 25 and 26; SEQ ID NO. 24, 25 and 27; SEQ ID NO. 24, 25 and 28; SEQ ID NO. 24, 25 and 29; SEQ ID NO. 24, 25 and 30; SEQ ID NO. 24, 26 and 27; SEQ ID NO. 24, 26 and 28; SEQ ID NO. 24, 26 and 29; SEQ ID NO. 24, 26 and 30; SEQ ID NO. 24, 27 and 28; SEQ ID NO. 24, 27 and 29; SEQ ID NO. 24, 27 and 30; SEQ ID NO. 24; 28 and 29; SEQ ID NO. 24, 28 and 30; SEQ ID NO. 24; 29 and 30; SEQ ID NO. 25, 26 and 27; SEQ ID NO. 25, 26 and 28; SEQ ID NO. 25, 26 and 29; SEQ ID NO. 25, 26 and 30; SEQ ID NO. 25, 27 and 28; SEQ ID NO. 25, 27 and 29; SEQ ID NO. 25, 27 and 30; SEQ ID NO. 25, 28 and 29; SEQ ID NO. 25, 28 and 30; SEQ ID NO. 25, 29 and 30; SEQ ID NO. 26, 27, and 28; SEQ ID NO. 26, 27 and 29; SEQ ID NO. 26, 27 and 30; SEQ ID NO. 26, 28 and 29; SEQ ID NO. 26, 28 and 30; SEQ ID NO. 26, 29 and 30; SEQ ID NO. 27, 28 and 29; SEQ ID NO. 27, 28 and 30; SEQ ID NO. 28, 29 and 30.

In the embodiments wherein four selected proteolysis peptides are monitored, these may be selected in a group comprising SEQ ID NO. 24, 25, 26 and 27; SEQ ID NO. 24, 25 26 and 28; SEQ ID NO. 24, 25, 26, and 29; SEQ ID NO. 24, 25, 26 and 30; SEQ ID NO. 24, 26, 27 and 28; SEQ ID NO. 24, 26, 27 and 29; SEQ ID NO. 24, 26, 27 and 30; SEQ ID NO. 24, 27, 28 and 29; SEQ ID NO. 24, 27, 28 and 30; SEQ ID NO. 24, 28, 29 and 30; SEQ ID NO. 25, 26, 27 and 28; SEQ ID NO. 25, 26, 27 and 29; SEQ ID NO. 25, 26, 27 and 30; SEQ ID NO. 25, 27, 28 and 29; SEQ ID NO. 25, 27, 28 and 30; SEQ ID NO. 25, 28, 29 and 30; SEQ ID NO. 26, 27, 28 and 29; SEQ ID NO. 26, 27, 28 and 30; SEQ ID NO. 26, 28, 29 and 30; SEQ ID NO. 27, 28, 29 and 30.

In the embodiments wherein five selected proteolysis peptides are monitored, these may be selected in a group comprising SEQ ID NO. 24, 25, 26, 27 and 28; SEQ ID NO. 24, 25, 26, 27, and 29; SEQ ID NO. 24, 25, 26, 27 and 30; SEQ ID NO. 24, 26, 27, 28 and 29; SEQ ID NO. 24, 26, 27, 28 and 30; SEQ ID NO. 24, 27, 28, 29 and 30; SEQ ID NO. 25, 26, 27, 28 and 29; SEQ ID NO. 25, 26, 27, 28 and 30; SEQ ID NO. 25, 27, 28, 29 and 30; SEQ ID NO. 26, 27, 28, 29 and 30.

In the embodiments wherein six selected proteolysis peptides are monitored, these may be selected in a group comprising SEQ ID NO. 24, 25, 26, 27, 28 and 29; SEQ ID NO. 24, 25, 26, 27, 28 and 30, SEQ ID NO. 24, 26, 27, 28, 29 and 30; SEQ ID NO. 25, 26, 27, 28, 29 and 30.

In the embodiments wherein seven selected proteolysis peptides are monitored, these may be selected in a group comprising SEQ ID NO. 24, 25, 26, 27, 28, 29 and 30.

In the embodiments wherein the proteolysis step is performed by using trypsin or a trypsin-containing protease composition and wherein a labeled counterpart of Golimumab is used as an Internal Standard compound, the number of selected proteolysis peptides for which a mass spectrometric signal ratio is determined at step c) may vary from 1 to 7, which encompasses 1, 2, 3, 4, 5, 6 and 7 selected proteolysis peptides.

In the embodiments wherein two selected proteolysis peptides are monitored, these may be selected in a group comprising SEQ ID NO. 31 and 32; SEQ ID NO. 31 and 33; SEQ ID NO. 31 and 34; SEQ ID NO. 31 and 35; SEQ ID NO. 31 and 36; SEQ ID NO. 31 and 37; SEQ ID NO. 32 and 33; SEQ ID NO. 32 and 34; SEQ ID NO. 32 and 35; SEQ ID NO. 32 and 36; SEQ ID NO. 32 and 37; SEQ ID NO. 33 and 34; SEQ ID NO. 33 and 35; SEQ ID NO. 33 and 36; SEQ ID NO. 33 and 37; SEQ ID NO. 34 and 35; SEQ ID NO. 34 and 36; SEQ ID NO. 34 and 37; SEQ ID NO. 35 and 36; SEQ ID NO. 35 and 37; SEQ ID NO. 36 and 37.

In the embodiments wherein three selected proteolysis peptides are monitored, these may be selected in a group comprising SEQ ID NO. 31, 32 and 33; SEQ ID NO. 31, 32 and 34; SEQ ID NO. 31, 32 and 35; SEQ ID NO. 31, 32 and 36; SEQ ID NO. 31, 32 and 37; SEQ ID NO. 31, 33 and 34; SEQ ID NO. 31, 33 and 35; SEQ ID NO. 31, 33 and 36; SEQ ID NO. 31, 33 and 37; SEQ ID NO. 31, 34 and 35; SEQ ID NO. 31, 34 and 36; SEQ ID NO. 31, 34 and 37; SEQ ID NO. 31; 35 and 36; SEQ ID NO. 31, 35 and 37; SEQ ID NO. 31; 36 and 37; SEQ ID NO. 32, 33 and 34; SEQ ID NO. 32, 33 and 35; SEQ ID NO. 32, 33 and 36; SEQ ID NO. 32, 33 and 37; SEQ ID NO. 32, 34 and 35; SEQ ID NO. 32, 34 and 36; SEQ ID NO. 32, 34 and 37; SEQ ID NO. 32, 35 and 36; SEQ ID NO. 32, 35 and 37; SEQ ID NO. 32, 36 and 37; SEQ ID NO. 33, 34, and 35; SEQ ID NO. 33, 34 and 36; SEQ ID NO. 33, 34 and 37; SEQ ID NO. 33, 35 and 36; SEQ ID NO. 33, 35 and 37; SEQ ID NO. 33, 36 and 37; SEQ ID NO. 34, 35 and 36; SEQ ID NO. 34, 35 and 37; SEQ ID NO. 35, 36 and 37.

In the embodiments wherein four selected proteolysis peptides are monitored, these may be selected in a group comprising SEQ ID NO. 31, 32, 33 and 34; SEQ ID NO. 31, 32 33 and 35; SEQ ID NO. 31, 32, 33, and 36; SEQ ID NO. 31, 32, 33 and 37; SEQ ID NO. 31, 33, 34 and 35; SEQ ID NO. 31, 33, 34 and 36; SEQ ID NO. 31, 33, 34 and 37; SEQ ID NO. 31, 34, 35 and 36; SEQ ID NO. 31, 34, 35 and 37;

SEQ ID NO. 31, 35, 36 and 37; SEQ ID NO. 32, 33, 34 and 35; SEQ ID NO. 32, 33, 34 and 36; SEQ ID NO. 32, 33, 34 and 37; SEQ ID NO. 32, 33, 35 and 36; SEQ ID NO. 32, 34, 35 and 37; SEQ ID NO. 32, 35, 36 and 37; SEQ ID NO. 33, 34, 35 and 36; SEQ ID NO. 33, 34, 35 and 37; SEQ ID NO. 33, 35, 36 and 37; SEQ ID NO. 34, 35, 36 and 37.

In the embodiments wherein five selected proteolysis peptides are monitored, these may be selected in a group comprising SEQ ID NO. 31, 32, 33, 34 and 35; SEQ ID NO. 31, 32, 33, 34, and 36; SEQ ID NO. 31, 32, 33, 34 and 37; SEQ ID NO. 31, 33, 34, 35 and 36; SEQ ID NO. 31, 33, 34, 35 and 37; SEQ ID NO. 31, 34, 35, 36 and 37; SEQ ID NO. 32, 33, 34, 35 and 36; SEQ ID NO. 32, 33, 34, 35 and 37; SEQ ID NO. 32, 34, 35, 36 and 37; SEQ ID NO. 33, 34, 35, 36 and 37.

In the embodiments wherein six selected proteolysis peptides are monitored, these may be selected in a group comprising SEQ ID NO. 31, 32, 33, 34, 35 and 36; SEQ ID NO. 31, 32, 33, 34, 35 and 37, SEQ ID NO. 31, 33, 34, 35, 36 and 37; SEQ ID NO. 32, 33, 34, 35, 36 and 37.

In the embodiments wherein seven selected proteolysis peptides are monitored, these may be selected in a group comprising SEQ ID NO. 31, 32, 33, 34, 35, 36 and 37.

For performing the anti-TNF antibodies quantification method of the invention wherein the proteolysis step b) makes use of a hinge-targeting protease, the one or more selected proteolysis peptides are selected in a group comprising:

for Infliximab: peptides of SEQ ID NO. 38-39,
for Etanercept: peptide of SEQ ID NO. 40,
for Adalimumab: peptides of SEQ ID NO. 41-42,
for Certolizumab: peptides of SEQ ID NO. 43-44, and
for Golimumab: peptides of SEQ ID NO. 45-46

In some embodiments, wherein the proteolysis step is performed by using a hinge-targeting protease and wherein a labeled counterpart of Infliximab is used as an Internal Standard compound, the spectrometric signals of one or both of the selected proteolysis peptides of SEQ ID NO. 38-39 are determined.

In some embodiments, wherein the proteolysis step is performed by using a hinge-targeting protease and wherein a labeled counterpart of Etanercept is used as an Internal Standard compound, the spectrometric signals of the selected proteolysis peptides of SEQ ID NO. 40 are determined.

In some embodiments, wherein the proteolysis step is performed by using a hinge-targeting protease and wherein a labeled counterpart of Adalimumab is used as an Internal Standard compound, the spectrometric signals of one or both of the selected proteolysis peptides of SEQ ID NO. 41-42 are determined.

In some embodiments, wherein the proteolysis step is performed by using a hinge-targeting protease and wherein a labeled counterpart of Certolizumab is used as an Internal Standard compound, the spectrometric signals of one or both of the selected proteolysis peptides of SEQ ID NO. 43-44 are determined.

In some embodiments, wherein the proteolysis step is performed by using a hinge-targeting protease and wherein a labeled counterpart of Golimumab is used as an Internal Standard compound, the spectrometric signals of one or both of the selected proteolysis peptides of SEQ ID NO. 45-46 are determined.

SRM transitions of selected proteolytic peptides from the anti-TNF antibodies tested, of proteolytic labeled peptides from the two or more anti-TNF antibodies used as Internal Standard compounds are preferably established after comparing the fragmentation spectra obtained from pure solutions of each of these peptides, with in silico fragmentation spectra generated with a relevant available software tool, such as the software commercialized under the name Skyline™ by MacCoss Lab Software (USA) and the bioinformatics tool ESP Predictor available from Genepattern (Vincent A. Fusaro, D. R. Mani, Jill P. Mesirov & Steven A. Carr, Nature Biotechnology (2009) 27:190-198), available notably from the Broad Institute (USA)

Preferably, at step d), quantification of anti-TNF antibodies is based on the ratio of the mean of the peak areas of specific SRM of a selected anti-TNF antibody and the mean of the peak areas of the Internal Standard selected surrogate labeled peptide.

More precisely, the amount of anti-TNF antibodies in the sample tested, e.g. the concentration of the said anti-TNF antibodies in the test sample, is determined by reporting the ratio value that is calculated at step d) for the said test sample to a calibration curve that was generated as previously described elsewhere in the present specification.

As shown in the examples, the quantification described herein allows linearity between the measured amount (e.g. concentration) of an anti-TNF antibody and the expected amount thereof.

Quantifying anti-TNF antibodies with the quantification method described herein allows a high quantification precision, a high quantification repeatability, as well as anti-TNF antibodies quantification over a wide range of amounts.

The anti-TNF antibodies quantification method according to the invention allows a linearity of the quantification measure from 1 µg/mL or less to 1000 µg/mL or more.

According to Food Drug Administration/European Medicines Agency (FDA/EMA) guidelines for bioanalytical method validation, it is thus shown herein that the anti-TNF antibodies quantification method according to the invention is at the same time sufficiently sensitive and reproducible to quantify anti-TNF antibodies in human plasma samples. It may be referred to the guidelines "Guidance for Industry—Bioanalytical Method validation" from the US department of Health and Human Services—Food and Drug Administration (2001); and corresponding EMA Quality guidelines.

The present invention also relates to kits for performing the anti-TNF antibody quantification method that is described throughout the present specification.

Thus, the present invention also relates to kits comprising two or more stable Isotopically Labeled anti-TNF antibodies; for quantifying anti-TNF antibodies in a human individual or a sample of a human individual.

The present invention also relates to kits comprising two or more stable Isotopically Labeled anti-TNF antibodies; for quantifying therapeutic anti-TNF antibodies in a human individual or a sample of a human individual.

In some embodiments, a kit according to the invention comprises two or more Stable Isotopically Labeled anti-TNF antibodies, especially two or more Stable Isotopically Labeled anti-TNF antibodies selected in a group comprising Infliximab, Etanercept, Adalimumab, Certolizumab and Golimumab. The SIL antibodies may be contained in a kit according to the invention in any combination, especially in any of the combinations that are described elsewhere in the present specification.

In some embodiments, the said kit comprises two SIL anti-TNF antibodies selected in a group comprising Infliximab, Etanercept, Adalimumab, Certolizumab and Golimumab. In some embodiments, the said kit comprises three SIL anti-TNF antibodies selected in a group comprising Infliximab, Etanercept, Adalimumab, Certolizumab and Golimumab. In some embodiments, the said kit comprises four SIL anti-TNF antibodies selected in a group comprising Infliximab, Etanercept, Adalimumab, Certolizumab and Golimumab. In some embodiments, the said kit comprises five SIL anti-TNF antibodies selected in a group comprising Infliximab, Etanercept, Adalimumab, Certolizumab and Golimumab.

In some embodiments, the SIL antibodies contained in a kit according to the invention may be under the form of a liquid suspension. In some other embodiments, the SIL antibodies contained in a kit according to the invention may be in a lyophilized form.

In some embodiments, the said kit further comprises reagents required for performing the anti-TNF antibody quantification method described herein, such as an appropriate protease, especially a protease selected in a group comprising (i) trypsin or a trypsin-containing composition and (ii) a hinge-targeting protease.

In some embodiments, the said kit also comprises information providing the calibration curves for each of the anti-TNF antibodies contained therein.

The present invention is further illustrated, without being limited thereto, by the examples below.

EXAMPLES

A. Materials end Methods
A.1. Test Sample Preparation

The test sample is a plasma sample or a serum sample that was previously collected from a patient to be tested.

Infliximab mAb PSAQ standard is spiked in the test sample at a final concentration which is preferably comprised between 5 µg/mL and 50 µg/ml, more preferably between 10 µg/mL and 25 µg/ml (ideally 20 µg/ml).

The sample volume used for the experiment is comprised between 5 µl and 1000 µl, more preferably between 10 µl and 100 µl, and ideally is 10 µl.

To 10 µl serum sample (up to 50 µl), add the labeled Infliximab standard at a concentration of 25 µg/ml (for example add 1 µl of a [250ng/µl] solution). Add PBS 1× to obtain a final sample volume of 100 µl.

A.2. Non-Antibody Protein Depletion by Affinity Chromatography

According to this embodiment, depletion in non-antibody proteins is performed by using an affinity chromatography support onto which TNF alpha was immobilized. More precisely, according to this method, biotinylated TNF alpha is added to the previously spiked test sample so as to capture the TNF binding molecules that are present in the spiked test sample, which includes (i) the Stable Isotope Labeled (SIL) anti-TNF antibodies used as Internal Standards and (ii) the other anti-TNF antibodies that are possibly present in the test sample before spiking with the SIL anti-TNF antibodies.

Then, the resulting mixture is brought into contact with a chromatographic support onto which streptavidin was immobilized, so as to capture the biotinylated TNF alpha that is possibly complexed with labeled and possibly non-labeled anti-TNF antibodies.

Then, the anti-TNF antibodies are eluted from the chromatographic support for further processing.

This method may be termed MSIA (for Mass Spectrometry ImmunoAffinity).

Reagents and Specific Instruments

Novus I Finnpipette 12 channel, 20-300 µl (Thermo), Streptavidin MSIA DARTs (Thermo), Biotinylated TNF-α (ACRO biosystems), Remicade (Janssen Biologics), Phosphate Buffered Saline (Gibco LifeSciences), Ammonium hydroxide solution (SIGMA-Aldrich), Acetonitrile LC-MS Chromasolv (Sigma-Aldrich), Formic Acid Aristar (VWR), Mix EndoLysC/Trypsine PROMEGA.

Preparation of the Biotinylated TNF-Alpha Solution

Dissolve 2.5 µg of biotinylated TNF-alpha in 100 µl PBS.

MSIA Experiment

Program the following step on the MSIA program:

Load Streptavidin MSIA tips on the pipette.

For the following step, it is very important to avoid air bubbles into the resin. To avoid bubbles, adjust the stand and the pipette in order that tips will always dip in solution along the experiment.

Select step WASH and wash the tips with PBS1× (volume of PBS required=200 µl).

Select the step CAPTURE 1 and aspirate the biotinylated TNF-alpha solution.

Select the step WASH and rinse the tips with PBS1× (volume of PBS required=200 µl).

Repeat this step twice.

Select the step CAPTURE 2 and aspirate the serum sample solution.

Select the step WASH and rinse the tips with Ammonium hydroxide solution (volume required=200 µl). Repeat this step and then WASH with 200 mM Ultrapure Water. Repeat this step twice.

Select the step ELUTE and elute with 30% Acetonitrile/ 0.05% formic acid solution (minimum volume required=100 µl).

Recover the eluate in a low-adsorption tube and dry the sample with a speed-vacuum.

A.3. Step of Enzyme Proteolysis

The step of enzyme proteolysis may be performed according to a plurality of embodiments. In some embodiments, enzyme proteolysis is performed through a method comprising two steps of trypsin digestion, (i) a step of trypsin digestion in denaturing conditions followed by (ii) a step of trypsin digestion in non-denaturing conditions, which method is referred as "Option 1" hereafter. In some other embodiments, enzyme proteolysis is performed through a method comprising a step of trypsin digestion in non-denaturing conditions, which method is referred as "option 2" hereafter. In still other embodiments, enzyme proteolysis is performed by using a hinge-targeting protease such as ideS (Immunoglobulin Degrading Enzyme form *Streptococcus*), which method is referred as "option 3" hereafter.

Option 1:Two-Step Trypsin Digestion

Trypsin Digestion in Denaturing Conditions

After complete dry, add 10 µl of 4M Urea solution in the tube and vortex. Check the pH of the sample that should be >6. If not, adjust the pH to 7-8 with 0.5M Tris Base solution.

Add 2 µg of EndolysC from the mix EndolysC/Trypsine (the amount of EndolysC added may vary between 0.2 and 4 µg)

Process to predigestion at 37° C. during 2H.

Trypsin Digestion in Non-Denaturing Conditions

Add 190 µl of a 25 mM ammonium bicarbonate solution in the tube, mix and add 2 µg of trypsine from the mix EndolysC/trypsine (again the amount of EndolysC added may vary between 0.2 and 4 µg). Process to digestion at 37° C. during 2-4 h or overnight if preferred.

Desalt and concentrate the sample with a C18-ziptip (Proteabio), eluate the ziptip, dry the eluate.

Prior to injection, resuspend the sample in 20 µl of a 2% Acetonitrile, 0.1% formic acid solution.

Inject the sample on the LC-MS instrument.

Option 2: One-Step Trypsin Digestion

After complete dry, add 10 μl of 25 mM ammonium bicarbonate solution in the tube and vortex. Check the pH of the sample that should be >6. If not, adjust the pH to 7-8 with 0.5M Tris Base solution. Add 2 μg of trypsine from the mix EndolysC/trypsine (again the amount of EndolysC added may vary between 0.2 and 4 μg). Process to digestion at 37° C. during 2-4 h or overnight if preferred.

Add formic acid in the sample to stop the digestion to obtain a final concentration of 0.1%.

Inject the sample on the LC-MS instrument.

Option 3: Protease Digestion with IdeS

After complete dry, resuspend the sample in 10 mM sodium phosphate, 150 mM NaCl, pH 7.4 or similar with pH ranging from 6.0-8.0 and check the pH (Adjust with Tris Base if necessary).

Break off the bottom seal of the FragIT™ column (save the cap) and slightly open the lid ~90° counter clockwise.

Place the column in a 1.5-2 ml collection tube and centrifuge the column at 200×g for 1 min to remove storage solution.

Equilibrate the column by adding 300 μl cleavage buffer and centrifuge the column at 200×g for 1 min.

Repeat steps 5 and 6 two times.

Put on the bottom cap on the column.

Immediately add the sample to be cleaved in a volume of 100 μl at a maximal concentration of 5 mg/ml IgG in cleavage buffer. Seal the column with the top lid. Take care to fully suspend the media manually and make sure it is flowing in the column. Incubate the column by end-over-end mixing for 15 min in room temperature. The incubation time can be increased without over digestion of the IgG.

Remove the top lid and the bottom cap. Place the column in a 1.5-2 ml collection tube. Centrifuge the column at 1000×g for 1 min to elute the sample. For maximum recovery of the sample, repeat twice this step using 100 μl cleavage buffer. Centrifuge the column at 1000×g for 1 min to elute the sample. Pool all the elution fractions.

If required, use a C4 ziptip to desalt the sample or precipitate with cold acetone, dry and resuspend in 2% ACN, 0.1% FA buffer.

A.4. LC-MS Analysis of Samples Treated with Option 1 or Option 2 (Trypsin Digestion)

The following peptides of sequences of SEQ ID NO. 1 to 37 should be monitored in the LC-SRM assay.

These peptides should be monitored in their labeled and non-labeled forms (mass increment will be calculated according to the stable-isotopically labeled amino acid present in the peptide sequence). Potential chemical modifications affecting amino acids should also be taken into account as these modifications will modify the m/z of peptide ions and corresponding fragments.

A.5. LC-MS Analysis of Samples Treated with Option 3 (IDES Digestion)

The following peptides of sequences SEQ ID NO. 39 to 46 should be monitored in the LC-SRM assay.

These peptides should be monitored in their labeled and non-labeled forms (mass increment will be calculated according to the stable-isotopically labeled amino acid present in the peptide sequence). Potential chemical modifications affecting amino acids should also be taken into account as these modifications will modify the m/z of peptide ions and corresponding fragments.

Example 1

Assessment of a Titration Curve for the Quantification in Human Serum Samples of the Therapeutic Antibody Infliximab in the Presence of Two Other Anti-TNF Antibodies, Using a Sample Preparation Based on Immunocapture (MSIA Technology The objective of this experiment was to perform a titration curve in order to assess the performances of the stable-isotopically labelled (SIL) antibody standards and of the LC-MS/MS method.

In Example 1, a titration curve was performed by using (i) non-labeled anti-TNF antibodies as Internal Standard Compounds and (ii) SIL Infliximab as the anti-TNF antibody to be quantified. Indeed, the same experiment may be performed by using (i) SIL anti-TNF antibodies as Internal Standard compounds and (ii) a non-labeled Infliximab as the anti-TNF antibody to be quantified.

A) Protocol

A titration curve was generated, according to the following protocol 1) adding to a serum sample defined amount of therapeutic anti-TNF antibodies, Infliximab, Adalimumab and Etanercept and 2) adding an increasing amount of SIL Infliximab. Thus, it is called a reverse titration curve because the SIL Infliximab is quantified using the therapeutic Infliximab.

Such an experiment mimics a situation where a patient would have been treated with Infliximab and whose serum will be analyzed using our LC-MS/MS method and three anti-TNF standards.

To perform this experiment, therapeutic antibodies Adalimumab, Etanercept and Infliximab were obtained from collaborators. The SIL Infliximab was produced and purified according to the method previously described (Lebert et al., Bioanalysis, 2015). Samples were treated using materials and methods described in Section A. Samples were treated following the option 1 described in the Section A. The peptides of sequences of SEQ ID NO. 1 to 23 were monitored in the LC-SRM assay, in their labelled and non-labelled forms.

TABLE 1

Samples constituted and analyzed to evaluate the accuracy and precision of our LC-MS/MS method in a context where multiple anti-TNF are present in the sample.

| Point | 1 | 2 | 3 | 4 | 5 | Zero |
|---|---|---|---|---|---|---|
| Human serum treated | 10 μl | 10 μl | 10 μl | 10 μl | 10 μl | 10 μl |
| Therapeutic Infliximab | 20 μg/ml | 20 μg/ml | 20 μg/ml | 20 μg/ml | 20 μg/ml | 20 μg/ml |

TABLE 1-continued

Samples constituted and analyzed to evaluate the accuracy and precision of our LC-MS/MS method in a context where multiple anti-TNF are present in the sample.

| Point | 1 | 2 | 3 | 4 | 5 | Zero |
|---|---|---|---|---|---|---|
| Therapeutic Adalimumab | 20 µg/ml | 20 µg/ml | 20 µg/ml | 20 µg/ml | 20 µg/ml | 20 µg/ml |
| Therapeutic Etanercept | 20 µg/ml | 20 µg/ml | 20 µg/ml | 20 µg/ml | 20 µg/ml | 20 µg/ml |
| SIL Infliximab | 1 µg/ml | 10 µg/ml | 20 µg/ml | 50 µg/ml | 100 µg/ml | 0 µg/ml |
| Final volume of the sample | 30 µl | 30 µl | 30 µl | 30 µl | 30 µl | 30 µl |

B) Experimental Results

The quantification performances provided by our approach combining the use of mAb SIL standards and LC-MS/MS were assessed in a multiplex manner, where three different anti-TNF antibodies were simultaneously present in the human serum samples. For these tests, we have produced a reverse titration curve covering a concentration range between 1 µg/ml and 100 µg/ml. In this experiment, the accuracy obtained for 10 µg/ml and 100 µg/ml were below 20%. The results are depicted in FIG. 1. The mean regression equation was Y=1.19x with a correlation coefficient $R^2$ of 0.999. For each concentration points, data obtained from the peptides monitored were consistent, indicating that our approach is robust. The accuracy was below 20% and fulfill the acceptance criteria. The high accuracy of the method demonstrates that it is possible to quantify with a high degree of precision a therapeutic anti-TNF antibody present in the blood of a patient using a generic and blinded approach, by combining the use of a SIL antibody standard and LC-MS.

Thus, the method can be applied for the personalized therapeutic follow-up of patients treated with anti-TNF therapeutic antibodies.

More interestingly, the experimental results show that the anti-TNF antibody quantification method described herein does not requires a selection of an antibody-specific quantification method as it is the case in the present usual practice. Moreover, the anti-TNF antibody quantification method allows correcting situations wherein a patient's treatment is erroneously documented, and also allows determining anti-TNF antibodies concentrations in test samples from patients which have undergone anti-TNF combination therapy treatments. Finally, the anti-TNF quantification method is not affected if the patient has received a first treatment with anti-TNF antibody and subsequently a second treatment with a second anti-TNF antibody distinct from the first antibody.

Example 2

Evaluation of the Maximum Concentration of Anti-TNF Antibodies which can be Present in the Sample Without Affecting the Antigen-Capture Using MSIA The objective of this experiment was to evaluate using a single anti-TNF antibody Infliximab the maximum concentration which can be measured with accuracy using our anti-TNF quantification approach.

A) Protocol

To perform this experiment, therapeutic antibody Infliximab was obtained from collaborators. The SIL Infliximab was produced and purified according to the method previously described (Lebert et al., Bioanalysis, 2015). Samples were treated using materials and methods described in Section A. Samples were treated following the option 1 described in the Section A. The peptides of sequences of SEQ ID NO. 1 to 8 were monitored in the LC-SRM assay, in their labelled and non-labelled forms.

TABLE 2

Samples constituted and analyzed to evaluate saturation of the TNF alpha antigen using a MSIA technology approach.

| Point | 1 | 2 | 3 | 4 |
|---|---|---|---|---|
| Human serum | 10 µl | 10 µl | 10 µl | 10 µl |
| Therapeutic Infliximab | 20 µg/ml | 50 µg/ml | 100 µg/ml | 200 µg/ml |
| SIL Infliximab | 40 µg/ml | 40 µg/ml | 40 µg/ml | 40 µg/ml |
| Final volume of the sample | 50 µl | 50 µl | 50 µl | 50 µl |

B) Experimental Results

Figure 2:
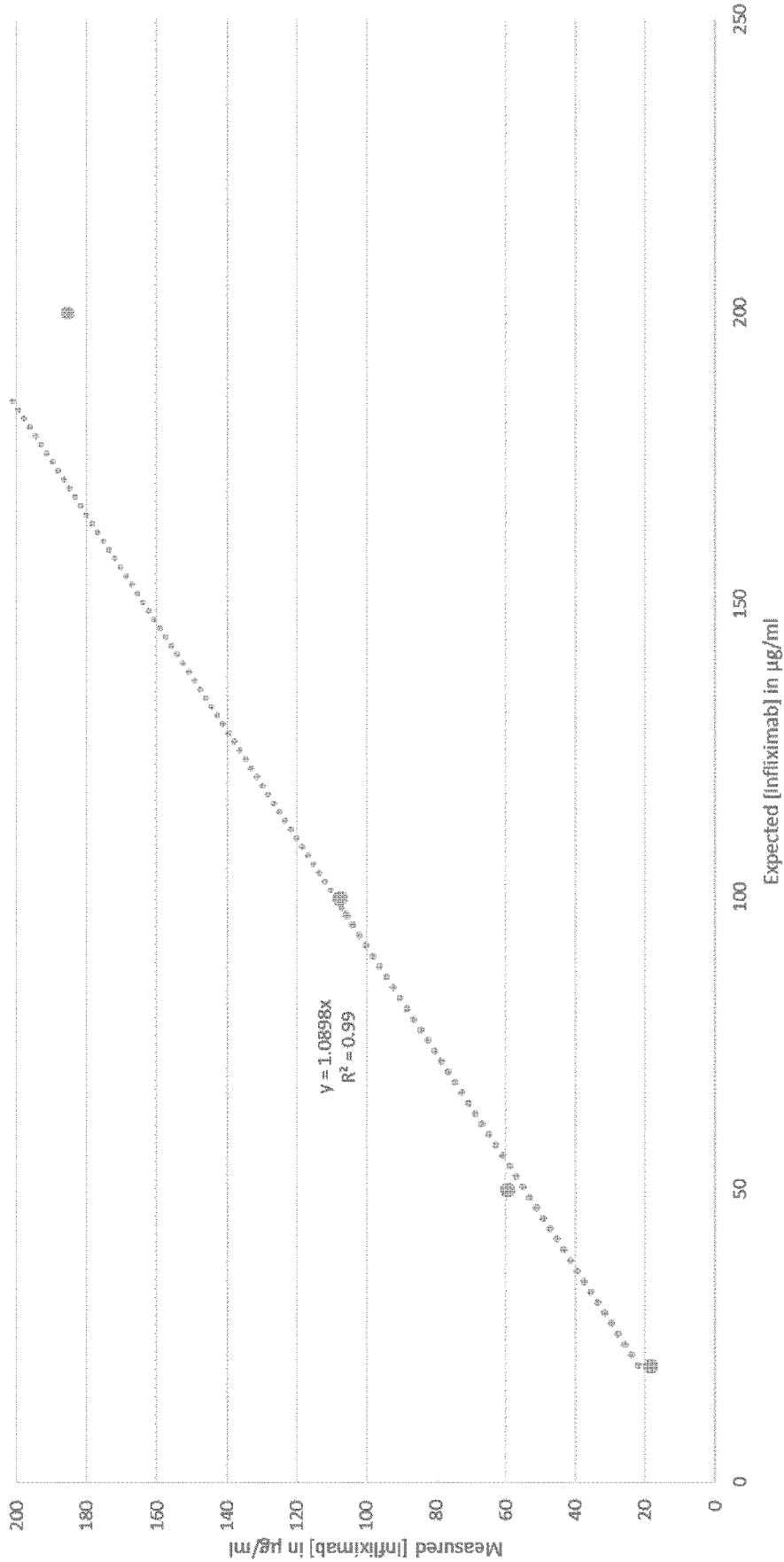
FIG. 2: Evaluation of the maximum concentration of anti-TNF antibodies which can be present in a test sample without affecting antigen-capture when using the MSIA method.
Ordinate: Measured concentration of Infliximab as expressed in µg/mL. Abscissa: expected concentration of Infliximab as expressed in µg/mL.

The experiment performed here aimed at evaluating the maximum concentration of anti-TNF which can be measured with accuracy using the anti-TNF antibody quantification method described herein. To limit the complexity, it was evaluated using a single anti-TNF antibody, Infliximab, which was spiked in human serum at different concentration covering a range between 20 µg/ml and 200 µg/ml, while the SIL Infliximab standard was spiked in the same sample at a relatively high concentration of 40 µg/ml. The results are depicted in FIG. 2. The results obtained show that the quantification of Infliximab in these conditions is accurate and remains linear when therapeutic Infliximab is present in the sample at a concentration of 100 µg/ml and when SIL Infliximab standard is spiked at a concentration of 40 µg/ml. With the linear curve obtained, we can even extrapolate that it would be linear and accurate when therapeutic Infliximab is present in the sample at a concentration of 150 µg/ml and when SIL Infliximab standard is spiked at a concentration of 40 µg/ml. However, a saturation phenomenon appears when therapeutic Infliximab is present in the sample at a concentration of 200 µg/ml and when SIL Infliximab standard is spiked at a concentration of 40 µg/ml. These results allows concluding that the MSIA protocol described for performing the anti-TNF antibody quantification method described herein with an MSIA technique allows measuring with accuracy an anti-TNF therapeutic antibody present in a human blood sample at a concentration equal or below 40 µg/ml using until 5 SIL anti-TNF antibodies, each one spiked at a concentration of 20 µg/ml (total=100 µg/ml) and even until 30 µg/ml (total=150 µg/ml). The results also show that the MSIA protocol, when used for performing the anti-TNF antibody quantification method described herein allows measuring with accuracy an anti-TNF therapeutic antibody present in a human blood sample at a concentration equal or below 150 µg/ml using until 2 SIL anti-TNF antibodies, each one spiked at a concentration of 20 µg/ml (total concentration of anti-TNF antibodies=40 µg/ml).

These results show that the mass spectrometry immuno-affinity protocol, which is an illustration of embodiments of anti-TNF antibody quantification method described herein, may be used for the quantification of an anti-TNF antibodies by using multiple SIL anti-TNF antibody standards.

TABLE 3

| SEQ ID NO. | Type | Description |
|---|---|---|
| 1 | Amino acid | Infliximab tryptic peptide |
| 2 | Amino acid | Infliximab tryptic peptide |
| 3 | Amino acid | Infliximab tryptic peptide |
| 4 | Amino acid | Infliximab tryptic peptide |
| 5 | Amino acid | Infliximab tryptic peptide |
| 6 | Amino acid | Infliximab tryptic peptide |
| 7 | Amino acid | Infliximab tryptic peptide |
| 8 | Amino acid | Infliximab tryptic peptide |
| 9 | Amino acid | Etanercept tryptic peptide |
| 10 | Amino acid | Etanercept tryptic peptide |
| 11 | Amino acid | Etanercept tryptic peptide |
| 12 | Amino acid | Etanercept tryptic peptide |

TABLE 3-continued

| SEQ ID NO. | Type | Description |
|---|---|---|
| 13 | Amino acid | Etanercept tryptic peptide |
| 14 | Amino acid | Etanercept tryptic peptide |
| 15 | Amino acid | Etanercept tryptic peptide |
| 16 | Amino acid | Adalimumab tryptic peptide |
| 18 | Amino acid | Adalimumab tryptic peptide |
| 19 | Amino acid | Adalimumab tryptic peptide |
| 20 | Amino acid | Adalimumab tryptic peptide |
| 21 | Amino acid | Adalimumab tryptic peptide |
| 22 | Amino acid | Adalimumab tryptic peptide |
| 23 | Amino acid | Adalimumab tryptic peptide |
| 24 | Amino acid | Certolizumab tryptic peptide |
| 25 | Amino acid | Certolizumab tryptic peptide |
| 26 | Amino acid | Certolizumab tryptic peptide |
| 27 | Amino acid | Certolizumab tryptic peptide |
| 28 | Amino acid | Certolizumab tryptic peptide |
| 29 | Amino acid | Certolizumab tryptic peptide |
| 30 | Amino acid | Certolizumab tryptic peptide |
| 31 | Amino acid | Golimumab tryptic peptide |
| 32 | Amino acid | Golimumab tryptic peptide |
| 33 | Amino acid | Golimumab tryptic peptide |
| 34 | Amino acid | Golimumab tryptic peptide |
| 35 | Amino acid | Golimumab tryptic peptide |
| 36 | Amino acid | Golimumab tryptic peptide |
| 37 | Amino acid | Golimumab tryptic peptide |
| 38 | Amino acid | Infliximab IdeS proteolytic peptide (VH + CH1) |
| 39 | Amino acid | Infliximab IdeS proteolytic peptide (VL + CL) |
| 40 | Amino acid | Etanercept IdeS proteolytic peptide |
| 41 | Amino acid | Adalimumab IdeS proteolytic peptide (VH + CH1) |
| 42 | Amino acid | Adalimumab IdeS proteolytic peptide (VL + CL) |
| 43 | Amino acid | Certolizumab IdeS proteolytic peptide (VH + CH1) |
| 44 | Amino acid | Certolizumab IdeS proteolytic peptide (VL + CL) |
| 45 | Amino acid | Golimumab IdeS proteolytic peptide (VH + CH1) |

TABLE 3-continued

Sequences

| SEQ ID NO. | Type | Description |
|---|---|---|
| 46 | Amino acid | Golimumab IdeS proteolytic peptide (VL + CL) |
| 47 | Amino acid | Infliximab, heavy chain |
| 48 | Amino acid | Infliximab, light chain |
| 49 | Amino acid | Adalimumab, heavy chain |
| 50 | Amino acid | Adalimumab, light chain |
| 51 | Amino acid | Etanercept |
| 52 | Amino acid | Certolizumab, heavy chain |
| 53 | Amino acid | Certolizumab, light chain |
| 54 | Amino acid | Golimumab, heavy chain |
| 55 | Amino acid | Golimumab, light chain |

The invention claimed is:

1. A kit for quantifying anti-TNF antibodies comprising two or more Stable Isotopically Labeled anti-TNF antibodies selected from a group consisting of Infliximab, Etanercept, Adalimumab, Certolizumab and Golimumab, wherein the two or more Stable Isotopically Labeled anti-TNF antibodies are whole antibodies.

2. The kit according to claim 1, further comprising a protease selected from a group consisting of (i) trypsin or a trypsin-containing composition and (ii) a hinge-targeting protease.

3. The kit according to claim 1, further comprising information providing the calibration curves for each of the anti-TNF antibodies contained therein.

* * * * *

SEQUENCE LISTING

```
<160> NUMBER OF SEQ ID NOS: 55

<210> SEQ ID NO 1
<211> LENGTH: 16
<212> TYPE: PRT
<213> ORGANISM: Artificial Sequence
<220> FEATURE:
<223> OTHER INFORMATION: Infliximab tryptic peptide
<220> FEATURE:
<223> OTHER INFORMATION: Infliximab tryptic peptide
<220> FEATURE:
<223> OTHER INFORMATION: Infliximab tryptic peptide

<400> SEQUENCE: 1

Leu Glu Glu Ser Gly Gly Gly Leu Val Gln Pro Gly Gly Ser Met Lys
1               5                   10                  15

<210> SEQ ID NO 2
<211> LENGTH: 9
<212> TYPE: PRT
<213> ORGANISM: Artificial Sequence
<220> FEATURE:
<223> OTHER INFORMATION: Infliximab tryptic peptide
<220> FEATURE:
<223> OTHER INFORMATION: Infliximab tryptic peptide
<220> FEATURE:
<223> OTHER INFORMATION: Infliximab tryptic peptide

<400> SEQUENCE: 2

Gly Leu Glu Trp Val Ala Glu Ile Arg
1               5

<210> SEQ ID NO 3
<211> LENGTH: 13
<212> TYPE: PRT
<213> ORGANISM: Artificial Sequence
<220> FEATURE:
<223> OTHER INFORMATION: Infliximab tryptic peptide
<220> FEATURE:
<223> OTHER INFORMATION: Infliximab tryptic peptide
<220> FEATURE:
<223> OTHER INFORMATION: Infliximab tryptic peptide

<400> SEQUENCE: 3

Ser Ile Asn Ser Ala Thr His Tyr Ala Glu Ser Val Lys
1               5                   10

<210> SEQ ID NO 4
<211> LENGTH: 11
<212> TYPE: PRT
```

```
<213> ORGANISM: Artificial Sequence
<220> FEATURE:
<223> OTHER INFORMATION: Infliximab trypric peptide
<220> FEATURE:
<223> OTHER INFORMATION: Infliximab trypric peptide
<220> FEATURE:
<223> OTHER INFORMATION: Infliximab trypric peptide

<400> SEQUENCE: 4

Ser Ala Val Tyr Leu Gln Met Thr Asp Leu Arg
1               5                   10

<210> SEQ ID NO 5
<211> LENGTH: 11
<212> TYPE: PRT
<213> ORGANISM: Artificial Sequence
<220> FEATURE:
<223> OTHER INFORMATION: Infliximab tryptic peptide
<220> FEATURE:
<223> OTHER INFORMATION: Infliximab tryptic peptide
<220> FEATURE:
<223> OTHER INFORMATION: Infliximab tryptic peptide

<400> SEQUENCE: 5

Thr Glu Asp Thr Gly Val Tyr Tyr Cys Ser Arg
1               5                   10

<210> SEQ ID NO 6
<211> LENGTH: 18
<212> TYPE: PRT
<213> ORGANISM: Artificial Sequence
<220> FEATURE:
<223> OTHER INFORMATION: Infliximab tryptic peptide
<220> FEATURE:
<223> OTHER INFORMATION: Infliximab tryptic peptide
<220> FEATURE:
<223> OTHER INFORMATION: Infliximab tryptic peptide

<400> SEQUENCE: 6

Asp Ile Leu Leu Thr Gln Ser Pro Ala Ile Leu Ser Val Ser Pro Gly
1               5                   10                  15

Glu Arg

<210> SEQ ID NO 7
<211> LENGTH: 15
<212> TYPE: PRT
<213> ORGANISM: Artificial Sequence
<220> FEATURE:
<223> OTHER INFORMATION: Infliximab tryptic peptide
<220> FEATURE:
<223> OTHER INFORMATION: Infliximab tryptic peptide
<220> FEATURE:
<223> OTHER INFORMATION: Infliximab tryptic peptide

<400> SEQUENCE: 7

Ala Ser Gln Phe Val Gly Ser Ser Ile His Trp Tyr Gln Gln Arg
1               5                   10                  15

<210> SEQ ID NO 8
<211> LENGTH: 12
<212> TYPE: PRT
<213> ORGANISM: Artificial Sequence
<220> FEATURE:
<223> OTHER INFORMATION: Infliximab tryptic peptide
<220> FEATURE:
<223> OTHER INFORMATION: Infliximab tryptic peptide
<220> FEATURE:
<223> OTHER INFORMATION: Infliximab tryptic peptide
```

```
<400> SEQUENCE: 8

Tyr Ala Ser Glu Ser Met Ser Gly Ile Pro Ser Arg
1               5                   10

<210> SEQ ID NO 9
<211> LENGTH: 19
<212> TYPE: PRT
<213> ORGANISM: Artificial Sequence
<220> FEATURE:
<223> OTHER INFORMATION: Etanercept tryptic peptide
<220> FEATURE:
<223> OTHER INFORMATION: Etanercept tryptic peptide
<220> FEATURE:
<223> OTHER INFORMATION: Etanercept tryptic peptide

<400> SEQUENCE: 9

Leu Pro Ala Gln Val Ala Phe Thr Pro Tyr Ala Pro Glu Pro Gly Ser
1               5                   10                  15

Thr Cys Arg

<210> SEQ ID NO 10
<211> LENGTH: 13
<212> TYPE: PRT
<213> ORGANISM: Artificial Sequence
<220> FEATURE:
<223> OTHER INFORMATION: Etanercept tryptic peptide
<220> FEATURE:
<223> OTHER INFORMATION: Etanercept tryptic peptide
<220> FEATURE:
<223> OTHER INFORMATION: Etanercept tryptic peptide

<400> SEQUENCE: 10

Glu Tyr Tyr Asp Gln Thr Ala Gln Met Cys Cys Ser Lys
1               5                   10

<210> SEQ ID NO 11
<211> LENGTH: 13
<212> TYPE: PRT
<213> ORGANISM: Artificial Sequence
<220> FEATURE:
<223> OTHER INFORMATION: Etanercept tryptic peptide
<220> FEATURE:
<223> OTHER INFORMATION: Etanercept tryptic peptide
<220> FEATURE:
<223> OTHER INFORMATION: Etanercept tryptic peptide

<400> SEQUENCE: 11

Cys Ser Ser Asp Gln Val Glu Thr Gln Ala Cys Thr Arg
1               5                   10

<210> SEQ ID NO 12
<211> LENGTH: 14
<212> TYPE: PRT
<213> ORGANISM: Artificial Sequence
<220> FEATURE:
<223> OTHER INFORMATION: Etanercept tryptic peptide
<220> FEATURE:
<223> OTHER INFORMATION: Etanercept tryptic peptide
<220> FEATURE:
<223> OTHER INFORMATION: Etanercept tryptic peptide

<400> SEQUENCE: 12

Ile Cys Thr Cys Arg Pro Gly Trp Tyr Cys Ala Leu Ser Lys
1               5                   10

<210> SEQ ID NO 13
<211> LENGTH: 6
```

```
<212> TYPE: PRT
<213> ORGANISM: Artificial Sequence
<220> FEATURE:
<223> OTHER INFORMATION: Etanercept tryptic peptide
<220> FEATURE:
<223> OTHER INFORMATION: Etanercept tryptic peptide
<220> FEATURE:
<223> OTHER INFORMATION: Etanercept tryptic peptide

<400> SEQUENCE: 13

Leu Cys Ala Pro Leu Arg
1               5

<210> SEQ ID NO 14
<211> LENGTH: 16
<212> TYPE: PRT
<213> ORGANISM: Artificial Sequence
<220> FEATURE:
<223> OTHER INFORMATION: Etanercept tryptic peptide
<220> FEATURE:
<223> OTHER INFORMATION: Etanercept tryptic peptide
<220> FEATURE:
<223> OTHER INFORMATION: Etanercept tryptic peptide

<400> SEQUENCE: 14

Ser Met Ala Pro Gly Ala Val His Leu Pro Gln Pro Val Ser Thr Arg
1               5                   10                  15

<210> SEQ ID NO 15
<211> LENGTH: 37
<212> TYPE: PRT
<213> ORGANISM: Artificial Sequence
<220> FEATURE:
<223> OTHER INFORMATION: Etanercept tryptic peptide
<220> FEATURE:
<223> OTHER INFORMATION: Etanercept tryptic peptide
<220> FEATURE:
<223> OTHER INFORMATION: Etanercept tryptic peptide

<400> SEQUENCE: 15

Ser Gln His Thr Gln Pro Thr Pro Glu Pro Ser Thr Ala Pro Ser Thr
1               5                   10                  15

Ser Phe Leu Leu Pro Met Gly Pro Ser Pro Pro Ala Glu Gly Ser Thr
                20                  25                  30

Gly Asp Glu Pro Lys
        35

<210> SEQ ID NO 16
<211> LENGTH: 24
<212> TYPE: PRT
<213> ORGANISM: Artificial Sequence
<220> FEATURE:
<223> OTHER INFORMATION: Adalimumab tryptic peptide
<220> FEATURE:
<223> OTHER INFORMATION: Adalimumab tryptic peptide
<220> FEATURE:
<223> OTHER INFORMATION: Adalimumab tryptic peptide

<400> SEQUENCE: 16

Gly Leu Glu Trp Val Ser Ala Ile Thr Trp Asn Ser Gly His Ile Asp
1               5                   10                  15

Tyr Ala Asp Ser Val Glu Gly Arg
            20

<210> SEQ ID NO 17
<211> LENGTH: 27
<212> TYPE: PRT
<213> ORGANISM: Artificial Sequence
```

```
<220> FEATURE:
<223> OTHER INFORMATION: Adalimumab tryptic peptide
<220> FEATURE:
<223> OTHER INFORMATION: Adalimumab tryptic peptide
<220> FEATURE:
<223> OTHER INFORMATION: Adalimumab tryptic peptide

<400> SEQUENCE: 17

Val Ser Tyr Leu Ser Thr Ala Ser Ser Leu Asp Tyr Trp Gly Gln Gly
1               5                   10                  15

Thr Leu Val Thr Val Ser Ser Ala Ser Thr Lys
            20                  25

<210> SEQ ID NO 18
<211> LENGTH: 29
<212> TYPE: PRT
<213> ORGANISM: Artificial Sequence
<220> FEATURE:
<223> OTHER INFORMATION: Adalimumab tryptic peptide
<220> FEATURE:
<223> OTHER INFORMATION: Adalimumab tryptic peptide
<220> FEATURE:
<223> OTHER INFORMATION: Adalimumab tryptic peptide

<400> SEQUENCE: 18

Gln Ala Pro Gly Lys Gly Leu Glu Trp Val Ser Ala Ile Thr Trp Asn
1               5                   10                  15

Ser Gly His Ile Asp Tyr Ala Asp Ser Val Glu Gly Arg
            20                  25

<210> SEQ ID NO 19
<211> LENGTH: 6
<212> TYPE: PRT
<213> ORGANISM: Artificial Sequence
<220> FEATURE:
<223> OTHER INFORMATION: Adalimumab tryptic peptide
<220> FEATURE:
<223> OTHER INFORMATION: Adalimumab tryptic peptide
<220> FEATURE:
<223> OTHER INFORMATION: Adalimumab tryptic peptide

<400> SEQUENCE: 19

Ala Ser Gln Gly Ile Arg
1               5

<210> SEQ ID NO 20
<211> LENGTH: 12
<212> TYPE: PRT
<213> ORGANISM: Artificial Sequence
<220> FEATURE:
<223> OTHER INFORMATION: Adalimumab tryptic peptide
<220> FEATURE:
<223> OTHER INFORMATION: Adalimumab tryptic peptide
<220> FEATURE:
<223> OTHER INFORMATION: Adalimumab tryptic peptide

<400> SEQUENCE: 20

Asn Tyr Leu Ala Trp Tyr Gln Gln Lys Pro Gly Lys
1               5                   10

<210> SEQ ID NO 21
<211> LENGTH: 16
<212> TYPE: PRT
<213> ORGANISM: Artificial Sequence
<220> FEATURE:
<223> OTHER INFORMATION: Adalimumab tryptic peptide
<220> FEATURE:
<223> OTHER INFORMATION: Adalimumab tryptic peptide
<220> FEATURE:
```

<223> OTHER INFORMATION: Adalimumab tryptic peptide

<400> SEQUENCE: 21

Leu Leu Ile Tyr Ala Ala Ser Thr Leu Gln Ser Gly Val Pro Ser Arg
1               5                   10                  15

<210> SEQ ID NO 22
<211> LENGTH: 29
<212> TYPE: PRT
<213> ORGANISM: Artificial Sequence
<220> FEATURE:
<223> OTHER INFORMATION: Adalimumab tryptic peptide
<220> FEATURE:
<223> OTHER INFORMATION: Adalimumab tryptic peptide
<220> FEATURE:
<223> OTHER INFORMATION: Adalimumab tryptic peptide

<400> SEQUENCE: 22

Phe Ser Gly Ser Gly Ser Gly Thr Asp Phe Thr Leu Thr Ile Ser Ser
1               5                   10                  15

Leu Gln Pro Glu Asp Val Ala Thr Tyr Tyr Cys Gln Arg
            20                  25

<210> SEQ ID NO 23
<211> LENGTH: 10
<212> TYPE: PRT
<213> ORGANISM: Artificial Sequence
<220> FEATURE:
<223> OTHER INFORMATION: Adalimumab tryptic peptide
<220> FEATURE:
<223> OTHER INFORMATION: Adalimumab tryptic peptide
<220> FEATURE:
<223> OTHER INFORMATION: Adalimumab tryptic peptide

<400> SEQUENCE: 23

Ala Pro Tyr Thr Phe Gly Gln Gly Thr Lys
1               5                   10

<210> SEQ ID NO 24
<211> LENGTH: 19
<212> TYPE: PRT
<213> ORGANISM: Artificial Sequence
<220> FEATURE:
<223> OTHER INFORMATION: Certolizumab tryptic peptide
<220> FEATURE:
<223> OTHER INFORMATION: Certolizumab tryptic peptide
<220> FEATURE:
<223> OTHER INFORMATION: Certolizumab tryptic peptide

<400> SEQUENCE: 24

Leu Ser Cys Ala Ala Ser Gly Tyr Val Phe Thr Asp Tyr Gly Met Asn
1               5                   10                  15

Trp Val Arg

<210> SEQ ID NO 25
<211> LENGTH: 22
<212> TYPE: PRT
<213> ORGANISM: Artificial Sequence
<220> FEATURE:
<223> OTHER INFORMATION: Certolizumab tryptic peptide
<220> FEATURE:
<223> OTHER INFORMATION: Certolizumab tryptic peptide
<220> FEATURE:
<223> OTHER INFORMATION: Certolizumab tryptic peptide

<400> SEQUENCE: 25

Gly Leu Glu Trp Met Gly Trp Ile Asn Thr Tyr Ile Gly Glu Pro Ile
1               5                   10                  15

Tyr Ala Asp Ser Val Lys
            20

<210> SEQ ID NO 26
<211> LENGTH: 9
<212> TYPE: PRT
<213> ORGANISM: Artificial Sequence
<220> FEATURE:
<223> OTHER INFORMATION: Certolizumab tryptic peptide
<220> FEATURE:
<223> OTHER INFORMATION: Certolizumab tryptic peptide
<220> FEATURE:
<223> OTHER INFORMATION: Certolizumab tryptic peptide

<400> SEQUENCE: 26

Phe Thr Phe Ser Leu Asp Thr Ser Lys
1               5

<210> SEQ ID NO 27
<211> LENGTH: 11
<212> TYPE: PRT
<213> ORGANISM: Artificial Sequence
<220> FEATURE:
<223> OTHER INFORMATION: Certolizumab tryptic peptide
<220> FEATURE:
<223> OTHER INFORMATION: Certolizumab tryptic peptide
<220> FEATURE:
<223> OTHER INFORMATION: Certolizumab tryptic peptide

<400> SEQUENCE: 27

Ser Thr Ala Tyr Leu Gln Met Asn Ser Leu Arg
1               5                   10

<210> SEQ ID NO 28
<211> LENGTH: 18
<212> TYPE: PRT
<213> ORGANISM: Artificial Sequence
<220> FEATURE:
<223> OTHER INFORMATION: Certolizumab tryptic peptide
<220> FEATURE:
<223> OTHER INFORMATION: Certolizumab tryptic peptide
<220> FEATURE:
<223> OTHER INFORMATION: Certolizumab tryptic peptide

<400> SEQUENCE: 28

Ala Ser Gln Asn Val Gly Thr Asn Val Ala Trp Tyr Gln Gln Lys Pro
1               5                   10                  15

Gly Lys

<210> SEQ ID NO 29
<211> LENGTH: 16
<212> TYPE: PRT
<213> ORGANISM: Artificial Sequence
<220> FEATURE:
<223> OTHER INFORMATION: Certolizumab tryptic peptide
<220> FEATURE:
<223> OTHER INFORMATION: Certolizumab tryptic peptide
<220> FEATURE:
<223> OTHER INFORMATION: Certolizumab tryptic peptide

<400> SEQUENCE: 29

Ala Leu Ile Tyr Ser Ala Ser Phe Leu Tyr Ser Gly Val Pro Tyr Arg
1               5                   10                  15

<210> SEQ ID NO 30
<211> LENGTH: 42
<212> TYPE: PRT
<213> ORGANISM: Artificial Sequence

```
<220> FEATURE:
<223> OTHER INFORMATION: Certolizumab tryptic peptide
<220> FEATURE:
<223> OTHER INFORMATION: Certolizumab tryptic peptide
<220> FEATURE:
<223> OTHER INFORMATION: Certolizumab tryptic peptide

<400> SEQUENCE: 30

Phe Ser Gly Ser Gly Ser Gly Thr Asp Phe Thr Leu Thr Ile Ser Ser
1               5                   10                  15

Leu Gln Pro Glu Asp Phe Ala Thr Tyr Tyr Cys Gln Gln Tyr Asn Ile
            20                  25                  30

Tyr Pro Leu Thr Phe Gly Gln Gly Thr Lys
        35                  40

<210> SEQ ID NO 31
<211> LENGTH: 19
<212> TYPE: PRT
<213> ORGANISM: Artificial Sequence
<220> FEATURE:
<223> OTHER INFORMATION: Golimumab tryptic peptide
<220> FEATURE:
<223> OTHER INFORMATION: Golimumab tryptic peptide
<220> FEATURE:
<223> OTHER INFORMATION: Golimumab tryptic peptide

<400> SEQUENCE: 31

Leu Ser Cys Ala Ala Ser Gly Phe Ile Phe Ser Ser Tyr Ala Met His
1               5                   10                  15

Trp Val Arg

<210> SEQ ID NO 32
<211> LENGTH: 20
<212> TYPE: PRT
<213> ORGANISM: Artificial Sequence
<220> FEATURE:
<223> OTHER INFORMATION: Golimumab tryptic peptide
<220> FEATURE:
<223> OTHER INFORMATION: Golimumab tryptic peptide
<220> FEATURE:
<223> OTHER INFORMATION: Golimumab tryptic peptide

<400> SEQUENCE: 32

Gln Ala Pro Gly Asn Gly Leu Glu Trp Val Ala Phe Met Ser Tyr Asp
1               5                   10                  15

Gly Ser Asn Lys
            20

<210> SEQ ID NO 33
<211> LENGTH: 31
<212> TYPE: PRT
<213> ORGANISM: Artificial Sequence
<220> FEATURE:
<223> OTHER INFORMATION: Golimumab tryptic peptide
<220> FEATURE:
<223> OTHER INFORMATION: Golimumab tryptic peptide
<220> FEATURE:
<223> OTHER INFORMATION: Golimumab tryptic peptide

<400> SEQUENCE: 33

Gly Ile Ala Ala Gly Gly Asn Tyr Tyr Tyr Tyr Gly Met Asp Val Ile
1               5                   10                  15

Ser Ser Gln Gly Thr Thr Val Thr Val Ser Ser Ala Ser Thr Lys
            20                  25                  30

<210> SEQ ID NO 34
```

```
<211> LENGTH: 15
<212> TYPE: PRT
<213> ORGANISM: Artificial Sequence
<220> FEATURE:
<223> OTHER INFORMATION: Golimumab tryptic peptide
<220> FEATURE:
<223> OTHER INFORMATION: Golimumab tryptic peptide
<220> FEATURE:
<223> OTHER INFORMATION: Golimumab tryptic peptide

<400> SEQUENCE: 34

Ala Ser Gln Ser Val Tyr Ser Tyr Leu Ala Trp Tyr Gln Gln Lys
1               5                   10                  15

<210> SEQ ID NO 35
<211> LENGTH: 9
<212> TYPE: PRT
<213> ORGANISM: Artificial Sequence
<220> FEATURE:
<223> OTHER INFORMATION: Golimumab tryptic peptide
<220> FEATURE:
<223> OTHER INFORMATION: Golimumab tryptic peptide
<220> FEATURE:
<223> OTHER INFORMATION: Golimumab tryptic peptide

<400> SEQUENCE: 35

Leu Leu Ile Tyr Asp Ala Ser Asn Arg
1               5

<210> SEQ ID NO 36
<211> LENGTH: 30
<212> TYPE: PRT
<213> ORGANISM: Artificial Sequence
<220> FEATURE:
<223> OTHER INFORMATION: Golimumab tryptic peptide
<220> FEATURE:
<223> OTHER INFORMATION: Golimumab tryptic peptide
<220> FEATURE:
<223> OTHER INFORMATION: Golimumab tryptic peptide

<400> SEQUENCE: 36

Phe Ser Gly Ser Gly Ser Gly Thr Asp Phe Thr Leu Thr Ile Ser Ser
1               5                   10                  15

Leu Glu Pro Glu Asp Phe Ala Val Tyr Tyr Cys Gln Gln Arg
            20                  25                  30

<210> SEQ ID NO 37
<211> LENGTH: 13
<212> TYPE: PRT
<213> ORGANISM: Artificial Sequence
<220> FEATURE:
<223> OTHER INFORMATION: Golimumab tryptic peptide
<220> FEATURE:
<223> OTHER INFORMATION: Golimumab tryptic peptide
<220> FEATURE:
<223> OTHER INFORMATION: Golimumab tryptic peptide

<400> SEQUENCE: 37

Ser Asn Trp Pro Pro Phe Thr Phe Gly Pro Gly Thr Lys
1               5                   10

<210> SEQ ID NO 38
<211> LENGTH: 239
<212> TYPE: PRT
<213> ORGANISM: Artificial Sequence
<220> FEATURE:
<223> OTHER INFORMATION: Infliximab IdeS proteolytic peptide (VH+CH1)
<220> FEATURE:
<223> OTHER INFORMATION: Infliximab IdeS proteolytic peptide (VH+CH1)
<220> FEATURE:
```

<223> OTHER INFORMATION: Infliximab IdeS proteolytic peptide (VH+CH1)

<400> SEQUENCE: 38

Glu Val Lys Leu Glu Glu Ser Gly Gly Gly Leu Val Gln Pro Gly Gly
1               5                   10                  15

Ser Met Lys Leu Ser Cys Val Ala Ser Gly Phe Ile Phe Ser Asn His
            20                  25                  30

Trp Met Asn Trp Val Arg Gln Ser Pro Glu Lys Gly Leu Glu Trp Val
        35                  40                  45

Ala Glu Ile Arg Ser Lys Ser Ile Asn Ser Ala Thr His Tyr Ala Glu
    50                  55                  60

Ser Val Lys Gly Arg Phe Thr Ile Ser Arg Asp Asp Ser Lys Ser Ala
65                  70                  75                  80

Val Tyr Leu Gln Met Thr Asp Leu Arg Thr Glu Asp Thr Gly Val Tyr
                85                  90                  95

Tyr Cys Ser Arg Asn Tyr Tyr Gly Ser Thr Tyr Asp Tyr Trp Gly Gln
            100                 105                 110

Gly Thr Thr Leu Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly
225                 230                 235

<210> SEQ ID NO 39
<211> LENGTH: 214
<212> TYPE: PRT
<213> ORGANISM: Artificial Sequence
<220> FEATURE:
<223> OTHER INFORMATION: Infliximab IdeS proteolytic peptide (VL+CL)
<220> FEATURE:
<223> OTHER INFORMATION: Infliximab IdeS proteolytic peptide (VL+CL)
<220> FEATURE:
<223> OTHER INFORMATION: Infliximab IdeS proteolytic peptide (VL+CL)

<400> SEQUENCE: 39

Asp Ile Leu Leu Thr Gln Ser Pro Ala Ile Leu Ser Val Ser Pro Gly
1               5                   10                  15

Glu Arg Val Ser Phe Ser Cys Arg Ala Ser Gln Phe Val Gly Ser Ser
            20                  25                  30

Ile His Trp Tyr Gln Gln Arg Thr Asn Gly Ser Pro Arg Leu Leu Ile
        35                  40                  45

Lys Tyr Ala Ser Glu Ser Met Ser Gly Ile Pro Ser Arg Phe Ser Gly
    50                  55                  60

Ser Gly Ser Gly Thr Asp Phe Thr Leu Ser Ile Asn Thr Val Glu Ser
65                  70                  75                  80

```
Glu Asp Ile Ala Asp Tyr Tyr Cys Gln Gln Ser His Ser Trp Pro Phe
                85                  90                  95

Thr Phe Gly Ser Gly Thr Asn Leu Glu Val Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

```
<210> SEQ ID NO 40
<211> LENGTH: 256
<212> TYPE: PRT
<213> ORGANISM: Artificial Sequence
<220> FEATURE:
<223> OTHER INFORMATION: Etanercept IdeS proteolytic peptide
<220> FEATURE:
<223> OTHER INFORMATION: Etanercept IdeS proteolytic peptide
<220> FEATURE:
<223> OTHER INFORMATION: Etanercept IdeS proteolytic peptide

<400> SEQUENCE: 40

Leu Pro Ala Gln Val Ala Phe Thr Pro Tyr Ala Pro Glu Pro Gly Ser
1               5                   10                  15

Thr Cys Arg Leu Arg Glu Tyr Tyr Asp Gln Thr Ala Gln Met Cys Cys
                20                  25                  30

Ser Lys Cys Ser Pro Gly Gln His Ala Lys Val Phe Cys Thr Lys Thr
            35                  40                  45

Ser Asp Thr Val Cys Asp Ser Cys Glu Asp Ser Thr Tyr Thr Gln Leu
    50                  55                  60

Trp Asn Trp Val Pro Glu Cys Leu Ser Cys Gly Ser Arg Cys Ser Ser
65                  70                  75                  80

Asp Gln Val Glu Thr Gln Ala Cys Thr Arg Glu Gln Asn Arg Ile Cys
                85                  90                  95

Thr Cys Arg Pro Gly Trp Tyr Cys Ala Leu Ser Lys Gln Glu Gly Cys
            100                 105                 110

Arg Leu Cys Ala Pro Leu Arg Lys Cys Arg Pro Gly Phe Gly Val Ala
        115                 120                 125

Arg Pro Gly Thr Glu Thr Ser Asp Val Val Cys Lys Pro Cys Ala Pro
    130                 135                 140

Gly Thr Phe Ser Asn Thr Thr Ser Ser Thr Asp Ile Cys Arg Pro His
145                 150                 155                 160

Gln Ile Cys Asn Val Val Ala Ile Pro Gly Asn Ala Ser Met Asp Ala
                165                 170                 175

Val Cys Thr Ser Thr Ser Pro Thr Arg Ser Met Ala Pro Gly Ala Val
            180                 185                 190
```

His Leu Pro Gln Pro Val Ser Thr Arg Ser Gln His Thr Gln Pro Thr
        195                 200                 205

Pro Glu Pro Ser Thr Ala Pro Ser Thr Ser Phe Leu Leu Pro Met Gly
    210                 215                 220

Pro Ser Pro Pro Ala Glu Gly Ser Thr Gly Asp Glu Pro Lys Ser Cys
225                 230                 235                 240

Asp Lys Thr His Thr Cys Pro Pro Cys Pro Ala Pro Glu Leu Leu Gly
            245                 250                 255

<210> SEQ ID NO 41
<211> LENGTH: 240
<212> TYPE: PRT
<213> ORGANISM: Artificial Sequence
<220> FEATURE:
<223> OTHER INFORMATION: Adalimumab IdeS proteolytic peptide (VH+CH1)
<220> FEATURE:
<223> OTHER INFORMATION: Adalimumab IdeS proteolytic peptide (VH+CH1)
<220> FEATURE:
<223> OTHER INFORMATION: Adalimumab IdeS proteolytic peptide (VH+CH1)

<400> SEQUENCE: 41

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Ala Ile Thr Trp Asn Ser Gly His Ile Asp Tyr Ala Asp Ser Val
    50                  55                  60

Glu Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Val Ser Tyr Leu Ser Thr Ala Ser Ser Leu Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

<210> SEQ ID NO 42
<211> LENGTH: 214
<212> TYPE: PRT
<213> ORGANISM: Artificial Sequence
<220> FEATURE:
<223> OTHER INFORMATION: Adalimumab IdeS proteolytic peptide(VL+CL)

<220> FEATURE:
<223> OTHER INFORMATION: Adalimumab IdeS proteolytic peptide(VL+CL)
<220> FEATURE:
<223> OTHER INFORMATION: Adalimumab IdeS proteolytic peptide(VL+CL)

<400> SEQUENCE: 42

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Arg Tyr Asn Arg Ala Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 43
<211> LENGTH: 229
<212> TYPE: PRT
<213> ORGANISM: Artificial Sequence
<220> FEATURE:
<223> OTHER INFORMATION: Certolizumab IdeS proteolytic peptide (VH+CH1)
<220> FEATURE:
<223> OTHER INFORMATION: Certolizumab IdeS proteolytic peptide (VH+CH1)
<220> FEATURE:
<223> OTHER INFORMATION: Certolizumab IdeS proteolytic peptide (VH+CH1)

<400> SEQUENCE: 43

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Val Phe Thr Asp Tyr
            20                  25                  30

Gly Met Asn Trp Val Arg Gln Ala Pro Gly Lys Gly Leu Glu Trp Met
        35                  40                  45

Gly Trp Ile Asn Thr Tyr Ile Gly Glu Pro Ile Tyr Ala Asp Ser Val
50                  55                  60

Lys Gly Arg Phe Thr Phe Ser Leu Asp Thr Ser Lys Ser Thr Ala Tyr
65                  70                  75                  80

```
Leu Gln Met Asn Ser Leu Arg Ala Glu Asp Thr Ala Val Tyr Tyr Cys
                85                  90                  95

Ala Arg Gly Tyr Arg Ser Tyr Ala Met Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Ala Ala
225

<210> SEQ ID NO 44
<211> LENGTH: 214
<212> TYPE: PRT
<213> ORGANISM: Artificial Sequence
<220> FEATURE:
<223> OTHER INFORMATION: Certolizumab IdeS proteolytic peptide (VL+CL)
<220> FEATURE:
<223> OTHER INFORMATION: Certolizumab IdeS proteolytic peptide (VL+CL)
<220> FEATURE:
<223> OTHER INFORMATION: Certolizumab IdeS proteolytic peptide (VL+CL)

<400> SEQUENCE: 44

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Gly Thr Asn
            20                  25                  30

Val Ala Trp Tyr Gln Gln Lys Pro Gly Lys Ala Pro Lys Ala Leu Ile
        35                  40                  45

Tyr Ser Ala Ser Phe Leu Tyr Ser Gly Val Pro Tyr Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ile Tyr Pro Leu
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175
```

```
Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 45
<211> LENGTH: 246
<212> TYPE: PRT
<213> ORGANISM: Artificial Sequence
<220> FEATURE:
<223> OTHER INFORMATION: Golimumab IdeS proteolytic peptide (VH+CH1)
<220> FEATURE:
<223> OTHER INFORMATION: Golimumab IdeS proteolytic peptide (VH+CH1)
<220> FEATURE:
<223> OTHER INFORMATION: Golimumab IdeS proteolytic peptide (VH+CH1)

<400> SEQUENCE: 45

Gln Val Gln Leu Val Glu Ser Gly Gly Val Val Gln Pro Gly Arg
1               5                   10                  15

Ser Leu Arg Leu Ser Cys Ala Ala Ser Gly Phe Ile Phe Ser Ser Tyr
            20                  25                  30

Ala Met His Trp Val Arg Gln Ala Pro Gly Asn Gly Leu Glu Trp Val
        35                  40                  45

Ala Phe Met Ser Tyr Asp Gly Ser Asn Lys Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Gly Ile Ala Ala Gly Gly Asn Tyr Tyr Tyr Tyr Gly
            100                 105                 110

Met Asp Val Ile Ser Ser Gln Gly Thr Thr Val Thr Val Ser Ser Ala
        115                 120                 125

Ser Thr Lys Gly Pro Ser Val Phe Pro Leu Ala Pro Ser Ser Lys Ser
    130                 135                 140

Thr Ser Gly Gly Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
                165                 170                 175

Val His Thr Phe Pro Ala Val Leu Gln Ser Ser Gly Leu Tyr Ser Leu
            180                 185                 190

Ser Ser Val Val Thr Val Pro Ser Ser Ser Leu Gly Thr Gln Thr Tyr
        195                 200                 205

Ile Cys Asn Val Asn His Lys Pro Ser Asn Thr Lys Val Asp Lys Lys
    210                 215                 220

Val Glu Pro Lys Ser Cys Asp Lys Thr His Thr Cys Pro Pro Cys Pro
225                 230                 235                 240

Ala Pro Glu Leu Leu Gly
                245

<210> SEQ ID NO 46
<211> LENGTH: 215
<212> TYPE: PRT
<213> ORGANISM: Artificial Sequence
<220> FEATURE:
<223> OTHER INFORMATION: Golimumab IdeS proteolytic peptide (VL+CL)
```

<220> FEATURE:
<223> OTHER INFORMATION: Golimumab IdeS proteolytic peptide (VL+CL)
<220> FEATURE:
<223> OTHER INFORMATION: Golimumab IdeS proteolytic peptide (VL+CL)

<400> SEQUENCE: 46

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Tyr Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Phe Thr Phe Gly Pro Gly Thr Lys Val Asp Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
210                 215

<210> SEQ ID NO 47
<211> LENGTH: 450
<212> TYPE: PRT
<213> ORGANISM: Artificial Sequence
<220> FEATURE:
<223> OTHER INFORMATION: Infliximab, heavy chain
<220> FEATURE:
<223> OTHER INFORMATION: Infliximab, heavy chain

<400> SEQUENCE: 47

Glu Val Lys Leu Glu Glu Ser Gly Gly Gly Leu Val Gln Pro Gly Gly
1               5                   10                  15

Ser Met Lys Leu Ser Cys Val Ala Ser Gly Phe Ile Phe Ser Asn His
            20                  25                  30

Trp Met Asn Trp Val Arg Gln Ser Pro Glu Lys Gly Leu Glu Trp Val
        35                  40                  45

Ala Glu Ile Arg Ser Lys Ser Ile Asn Ser Ala Thr His Tyr Ala Glu
50                  55                  60

Ser Val Lys Gly Arg Phe Thr Ile Ser Arg Asp Asp Ser Lys Ser Ala
65                  70                  75                  80

Val Tyr Leu Gln Met Thr Asp Leu Arg Thr Glu Asp Thr Gly Val Tyr
                85                  90                  95

```
Tyr Cys Ser Arg Asn Tyr Gly Ser Thr Tyr Asp Tyr Trp Gly Gln
            100                 105                 110
Gly Thr Thr Leu Thr Val Ser Ser Ala Ser Thr Lys Gly Pro Ser Val
        115                 120                 125
Phe Pro Leu Ala Pro Ser Ser Lys Ser Thr Ser Gly Gly Thr Ala Ala
    130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
                165                 170                 175
Leu Gln Ser Ser Gly Leu Tyr Ser Leu Ser Ser Val Val Thr Val Pro
            180                 185                 190
Ser Ser Ser Leu Gly Thr Gln Thr Tyr Ile Cys Asn Val Asn His Lys
        195                 200                 205
Pro Ser Asn Thr Lys Val Asp Lys Lys Val Glu Pro Lys Ser Cys Asp
    210                 215                 220
Lys Thr His Thr Cys Pro Pro Cys Pro Ala Pro Glu Leu Leu Gly Gly
225                 230                 235                 240
Pro Ser Val Phe Leu Phe Pro Pro Lys Pro Lys Asp Thr Leu Met Ile
                245                 250                 255
Ser Arg Thr Pro Glu Val Thr Cys Val Val Val Asp Val Ser His Glu
            260                 265                 270
Asp Pro Glu Val Lys Phe Asn Trp Tyr Val Asp Gly Val Glu Val His
        275                 280                 285
Asn Ala Lys Thr Lys Pro Arg Glu Glu Gln Tyr Asn Ser Thr Tyr Arg
    290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Ala Leu Pro Ala Pro Ile Glu
                325                 330                 335
Lys Thr Ile Ser Lys Ala Lys Gly Gln Pro Arg Glu Pro Gln Val Tyr
            340                 345                 350
Thr Leu Pro Pro Ser Arg Asp Glu Leu Thr Lys Asn Gln Val Ser Leu
        355                 360                 365
Thr Cys Leu Val Lys Gly Phe Tyr Pro Ser Asp Ile Ala Val Glu Trp
    370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
                405                 410                 415
Lys Ser Arg Trp Gln Gln Gly Asn Val Phe Ser Cys Ser Val Met His
            420                 425                 430
Glu Ala Leu His Asn His Tyr Thr Gln Lys Ser Leu Ser Leu Ser Pro
        435                 440                 445
Gly Lys
    450

<210> SEQ ID NO 48
<211> LENGTH: 214
<212> TYPE: PRT
<213> ORGANISM: Artificial Sequence
<220> FEATURE:
<223> OTHER INFORMATION: Infliximab, light chain
<220> FEATURE:
<223> OTHER INFORMATION: Infliximab, light chain
```

<400> SEQUENCE: 48

```
Asp Ile Leu Leu Thr Gln Ser Pro Ala Ile Leu Ser Val Ser Pro Gly
1               5                   10                  15

Glu Arg Val Ser Phe Ser Cys Arg Ala Ser Gln Phe Val Gly Ser Ser
            20                  25                  30

Ile His Trp Tyr Gln Gln Arg Thr Asn Gly Ser Pro Arg Leu Leu Ile
        35                  40                  45

Lys Tyr Ala Ser Glu Ser Met Ser Gly Ile Pro Ser Arg Phe Ser Gly
    50                  55                  60

Ser Gly Ser Gly Thr Asp Phe Thr Leu Ser Ile Asn Thr Val Glu Ser
65                  70                  75                  80

Glu Asp Ile Ala Asp Tyr Tyr Cys Gln Gln Ser His Ser Trp Pro Phe
                85                  90                  95

Thr Phe Gly Ser Gly Thr Asn Leu Glu Val Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 49
<211> LENGTH: 451
<212> TYPE: PRT
<213> ORGANISM: Artificial Sequence
<220> FEATURE:
<223> OTHER INFORMATION: Adalimumab, heavy chain
<220> FEATURE:
<223> OTHER INFORMATION: Adalimumab, heavy chain

<400> SEQUENCE: 49

```
Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Ala Ile Thr Trp Asn Ser Gly His Ile Asp Tyr Ala Asp Ser Val
    50                  55                  60

Glu Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Val Ser Tyr Leu Ser Thr Ala Ser Ser Leu Asp Tyr Trp Gly
            100                 105                 110

Gln Gly Thr Leu Val Thr Val Ser Ser Ala Ser Thr Lys Gly Pro Ser
        115                 120                 125
```

Val Phe Pro Leu Ala Pro Ser Ser Lys Ser Thr Ser Gly Gly Thr Ala
        130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Val Glu Pro Lys Ser Cys
210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 50
<211> LENGTH: 214
<212> TYPE: PRT
<213> ORGANISM: Artificial Sequence
<220> FEATURE:
<223> OTHER INFORMATION: Adalimumab, light chain
<220> FEATURE:
<223> OTHER INFORMATION: Adalimumab, light chain

<400> SEQUENCE: 50

Asp Ile Gln Met Thr Gln Ser Pro Ser Ser Leu Ser Ala Ser Val Gly
1               5                   10                  15

```
Asp Arg Val Thr Ile Thr Cys Arg Ala Ser Gln Gly Ile Arg Asn Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Arg Tyr Asn Arg Ala Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 51
<211> LENGTH: 467
<212> TYPE: PRT
<213> ORGANISM: Artificial Sequence
<220> FEATURE:
<223> OTHER INFORMATION: Etanercept
<220> FEATURE:
<223> OTHER INFORMATION: Etanercept

<400> SEQUENCE: 51

Leu Pro Ala Gln Val Ala Phe Thr Pro Tyr Ala Pro Glu Pro Gly Ser
1               5                   10                  15

Thr Cys Arg Leu Arg Glu Tyr Tyr Asp Gln Thr Ala Gln Met Cys Cys
            20                  25                  30

Ser Lys Cys Ser Pro Gly Gln His Ala Lys Val Phe Cys Thr Lys Thr
        35                  40                  45

Ser Asp Thr Val Cys Asp Ser Cys Glu Asp Ser Thr Tyr Thr Gln Leu
    50                  55                  60

Trp Asn Trp Val Pro Glu Cys Leu Ser Cys Gly Ser Arg Cys Ser Ser
65                  70                  75                  80

Asp Gln Val Glu Thr Gln Ala Cys Thr Arg Glu Gln Asn Arg Ile Cys
                85                  90                  95

Thr Cys Arg Pro Gly Trp Tyr Cys Ala Leu Ser Lys Gln Glu Gly Cys
            100                 105                 110

Arg Leu Cys Ala Pro Leu Arg Lys Cys Arg Pro Gly Phe Gly Val Ala
        115                 120                 125

Arg Pro Gly Thr Glu Thr Ser Asp Val Val Cys Lys Pro Cys Ala Pro
    130                 135                 140
```

-continued

```
Gly Thr Phe Ser Asn Thr Thr Ser Thr Asp Ile Cys Arg Pro His
145                 150                 155                 160

Gln Ile Cys Asn Val Val Ala Ile Pro Gly Asn Ala Ser Met Asp Ala
            165                 170                 175

Val Cys Thr Ser Thr Ser Pro Thr Arg Ser Met Ala Pro Gly Ala Val
            180                 185                 190

His Leu Pro Gln Pro Val Ser Thr Arg Ser Gln His Thr Gln Pro Thr
            195                 200                 205

Pro Glu Pro Ser Thr Ala Pro Ser Thr Ser Phe Leu Leu Pro Met Gly
        210                 215                 220

Pro Ser Pro Pro Ala Glu Gly Ser Thr Gly Asp Glu Pro Lys Ser Cys
225                 230                 235                 240

Asp Lys Thr His Thr Cys Pro Pro Cys Pro Ala Pro Glu Leu Leu Gly
            245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
        275                 280                 285

Glu Asp Pro Glu Val Lys Phe Asn Trp Tyr Val Asp Gly Val Glu Val
        290                 295                 300

His Asn Ala Lys Thr Lys Pro Arg Glu Glu Gln Tyr Asn Ser Thr Tyr
305                 310                 315                 320

Arg Val Val Ser Val Leu Thr Val Leu His Gln Asp Trp Leu Asn Gly
            325                 330                 335

Lys Glu Tyr Lys Cys Lys Val Ser Asn Lys Ala Leu Pro Ala Pro Ile
            340                 345                 350

Glu Lys Thr Ile Ser Lys Ala Lys Gly Gln Pro Arg Glu Pro Gln Val
        355                 360                 365

Tyr Thr Leu Pro Pro Ser Arg Glu Glu Met Thr Lys Asn Gln Val Ser
        370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
            405                 410                 415

Val Leu Asp Ser Asp Gly Ser Phe Phe Leu Tyr Ser Lys Leu Thr Val
            420                 425                 430

Asp Lys Ser Arg Trp Gln Gln Gly Asn Val Phe Ser Cys Ser Val Met
        435                 440                 445

His Glu Ala Leu His Asn His Tyr Thr Gln Lys Ser Leu Ser Leu Ser
450                 455                 460

Pro Gly Lys
465

<210> SEQ ID NO 52
<211> LENGTH: 229
<212> TYPE: PRT
<213> ORGANISM: Artificial Sequence
<220> FEATURE:
<223> OTHER INFORMATION: Certolizumab, heavy chain
<220> FEATURE:
<223> OTHER INFORMATION: Certolizumab, heavy chain

<400> SEQUENCE: 52

Glu Val Gln Leu Val Glu Ser Gly Gly Gly Leu Val Gln Pro Gly Gly
1               5                   10                  15
```

```
Ser Leu Arg Leu Ser Cys Ala Ala Ser Gly Tyr Val Phe Thr Asp Tyr
            20                  25                  30

Gly Met Asn Trp Val Arg Gln Ala Pro Gly Lys Gly Leu Glu Trp Met
            35                  40                  45

Gly Trp Ile Asn Thr Tyr Ile Gly Glu Pro Ile Tyr Ala Asp Ser Val
50                      55                  60

Lys Gly Arg Phe Thr Phe Ser Leu Asp Thr Ser Lys Ser Thr Ala Tyr
65                      70                  75                  80

Leu Gln Met Asn Ser Leu Arg Ala Glu Asp Thr Ala Val Tyr Tyr Cys
            85                  90                  95

Ala Arg Gly Tyr Arg Ser Tyr Ala Met Asp Tyr Trp Gly Gln Gly Thr
            100                 105                 110

Leu Val Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
130                     135                 140

Cys Leu Val Lys Asp Tyr Phe Pro Glu Pro Val Thr Val Ser Trp Asn
145                     150                 155                 160

Ser Gly Ala Leu Thr Ser Gly Val His Thr Phe Pro Ala Val Leu Gln
            165                 170                 175

Ser Ser Gly Leu Tyr Ser Leu Ser Val Val Thr Val Pro Ser Ser
            180                 185                 190

Ser Leu Gly Thr Gln Thr Tyr Ile Cys Asn Val Asn His Lys Pro Ser
            195                 200                 205

Asn Thr Lys Val Asp Lys Lys Val Glu Pro Lys Ser Cys Asp Lys Thr
210                     215                 220

His Thr Cys Ala Ala
225

<210> SEQ ID NO 53
<211> LENGTH: 214
<212> TYPE: PRT
<213> ORGANISM: Artificial Sequence
<220> FEATURE:
<223> OTHER INFORMATION: Certolizumab, light chain
<220> FEATURE:
<223> OTHER INFORMATION: Certolizumab, light chain

<400> SEQUENCE: 53

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Gly Thr Asn
            20                  25                  30

Val Ala Trp Tyr Gln Gln Lys Pro Gly Lys Ala Pro Lys Ala Leu Ile
            35                  40                  45

Tyr Ser Ala Ser Phe Leu Tyr Ser Gly Val Pro Tyr Arg Phe Ser Gly
            50                  55                  60

Ser Gly Ser Gly Thr Asp Phe Thr Leu Thr Ile Ser Ser Leu Gln Pro
65                      70                  75                  80

Glu Asp Phe Ala Thr Tyr Tyr Cys Gln Gln Tyr Asn Ile Tyr Pro Leu
            85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125
```

```
Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
            195                 200                 205

Phe Asn Arg Gly Glu Cys
        210

<210> SEQ ID NO 54
<211> LENGTH: 457
<212> TYPE: PRT
<213> ORGANISM: Artificial Sequence
<220> FEATURE:
<223> OTHER INFORMATION: Golimumab, heavy chain
<220> FEATURE:
<223> OTHER INFORMATION: Golimumab, heavy chain

<400> SEQUENCE: 54

Gln Val Gln Leu Val Glu Ser Gly Gly Val Val Gln Pro Gly Arg
1               5                   10                  15

Ser Leu Arg Leu Ser Cys Ala Ala Ser Gly Phe Ile Phe Ser Ser Tyr
            20                  25                  30

Ala Met His Trp Val Arg Gln Ala Pro Gly Asn Gly Leu Glu Trp Val
        35                  40                  45

Ala Phe Met Ser Tyr Asp Gly Ser Asn Lys Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Gly Ile Ala Ala Gly Gly Asn Tyr Tyr Tyr Tyr Gly
            100                 105                 110

Met Asp Val Ile Ser Ser Gln Gly Thr Thr Val Thr Val Ser Ser Ala
        115                 120                 125

Ser Thr Lys Gly Pro Ser Val Phe Pro Leu Ala Pro Ser Ser Lys Ser
    130                 135                 140

Thr Ser Gly Gly Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
                165                 170                 175

Val His Thr Phe Pro Ala Val Leu Gln Ser Ser Gly Leu Tyr Ser Leu
            180                 185                 190

Ser Ser Val Val Thr Val Pro Ser Ser Ser Leu Gly Thr Gln Thr Tyr
        195                 200                 205

Ile Cys Asn Val Asn His Lys Pro Ser Asn Thr Lys Val Asp Lys Lys
    210                 215                 220

Val Glu Pro Lys Ser Cys Asp Lys Thr His Thr Cys Pro Pro Cys Pro
225                 230                 235                 240

Ala Pro Glu Leu Leu Gly Gly Pro Ser Val Phe Leu Phe Pro Pro Lys
                245                 250                 255
```

```
Pro Lys Asp Thr Leu Met Ile Ser Arg Thr Pro Glu Val Thr Cys Val
            260                 265                 270

Val Val Asp Val Ser His Glu Asp Pro Glu Val Lys Phe Asn Trp Tyr
        275                 280                 285

Val Asp Gly Val Glu Val His Asn Ala Lys Thr Lys Pro Arg Glu Glu
    290                 295                 300

Gln Tyr Asn Ser Thr Tyr Arg Val Val Ser Val Leu Thr Val Leu His
305                 310                 315                 320

Gln Asp Trp Leu Asn Gly Lys Glu Tyr Lys Cys Lys Val Ser Asn Lys
                325                 330                 335

Ala Leu Pro Ala Pro Ile Glu Lys Thr Ile Ser Lys Ala Lys Gly Gln
            340                 345                 350

Pro Arg Glu Pro Gln Val Tyr Thr Leu Pro Pro Ser Arg Asp Glu Leu
        355                 360                 365

Thr Lys Asn Gln Val Ser Leu Thr Cys Leu Val Lys Gly Phe Tyr Pro
    370                 375                 380

Ser Asp Ile Ala Val Glu Trp Glu Ser Asn Gly Gln Pro Glu Asn Asn
385                 390                 395                 400

Tyr Lys Thr Thr Pro Pro Val Leu Asp Ser Asp Gly Ser Phe Phe Leu
                405                 410                 415

Tyr Ser Lys Leu Thr Val Asp Lys Ser Arg Trp Gln Gln Gly Asn Val
            420                 425                 430

Phe Ser Cys Ser Val Met His Glu Ala Leu His Asn His Tyr Thr Gln
        435                 440                 445

Lys Ser Leu Ser Leu Ser Pro Gly Lys
    450                 455

<210> SEQ ID NO 55
<211> LENGTH: 215
<212> TYPE: PRT
<213> ORGANISM: Artificial Sequence
<220> FEATURE:
<223> OTHER INFORMATION: Golimumab, light chain
<220> FEATURE:
<223> OTHER INFORMATION: Golimumab, light chain

<400> SEQUENCE: 55

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Tyr Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Phe Thr Phe Gly Pro Gly Thr Lys Val Asp Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
130                 135                 140
```

```
Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215
```